United States Patent [19]

Poss

[11] Patent Number: 5,545,838
[45] Date of Patent: Aug. 13, 1996

[54] DIOL SULFONAMIDE AND SULFINYL RENIN INHIBITORS

[75] Inventor: Michael A. Poss, Lawrenceville, N.J.

[73] Assignee: E. R. Squibb & Sons, Inc., Princeton, N.J.

[21] Appl. No.: 826,586

[22] Filed: Jan. 27, 1992

Related U.S. Application Data

[62] Division of Ser. No. 408,157, Sep. 15, 1989, Pat. No. 5,098,924.

[51] Int. Cl.⁶ ............ C07D 233/64; C07D 277/30; C07D 209/34; C07D 209/10; C07D 211/82; C07D 237/00; C07D 403/00; C07C 309/00

[52] U.S. Cl. ............ 564/89; 546/335; 544/238; 544/224; 544/406; 548/333.5; 548/338.5; 548/204; 548/486; 548/507; 564/248; 564/84; 564/85; 564/86; 564/88; 564/95

[58] Field of Search ............ 546/335, 406; 544/238, 224; 548/333.5, 338.5, 204, 456, 507; 564/248, 84, 85, 86, 88, 89, 95

[56] References Cited

U.S. PATENT DOCUMENTS

| | | | |
|---|---|---|---|
| 4,645,759 | 2/1987 | Luly et al. | 514/18 |
| 4,657,931 | 4/1987 | Baran et al. | 514/616 |
| 4,680,284 | 7/1987 | Luly et al. | 514/18 |
| 4,725,583 | 2/1988 | Luly et al. | 514/18 |
| 4,837,204 | 6/1989 | Rosenberg et al. | 514/18 |
| 4,864,017 | 9/1989 | Thaisrivongs | 530/329 |
| 4,904,660 | 2/1990 | Nakano | 514/236.2 |

FOREIGN PATENT DOCUMENTS

| | | |
|---|---|---|
| 189203 | 7/1986 | European Pat. Off. |
| 230266 | 7/1987 | European Pat. Off. |
| 309766 | 4/1989 | European Pat. Off. |
| 331105 | 9/1989 | European Pat. Off. |
| 3830825 | 2/1989 | Germany |
| 3825242 | 2/1989 | Germany |
| 2200115 | 7/1988 | United Kingdom |
| 88/05050 | 7/1988 | WIPO |
| 88/07053 | 9/1988 | WIPO |

OTHER PUBLICATIONS

Plattner et al., J. Med. Chem. 31,2277–2288 (1988).
Bolis et al., J. Med. Chem., 30,1729–1737 (1987).
Denkwalter et al., Progress in Drug Research, vol. 10, 510–512, (1966).
Burger, A. Medicinal Chemistry, 2nd Ed. pp. 565–571, 578–581, 600–601 (1960).
Haber et al., J. Cardiovascular Pharmacology, 10 (Suppl. 7) 554–558 (1987).

*Primary Examiner*—Johann Richter
*Attorney, Agent, or Firm*—Stephen B. Davis

[57] ABSTRACT

Compounds of the formula

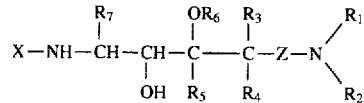

wherein Z is SO or $SO_2$ possess renin inhibition activity and are useful in treating hypertension and other diseases where the reduction of the levels of circulating angiotensin II are beneficial.

50 Claims, No Drawings

DIOL SULFONAMIDE AND SULFINYL RENIN INHIBITORS

RELATED APPLICATION

This application is a divisional of Ser. No. 408,157, filed Sep. 15, 1989, now U.S. Pat. No. 5,098,924.

BACKGROUND OF THE INVENTION

Luly et al. in U.S. Pat. No. 4,645,759 disclose renin inhibiting compounds including those of the formula

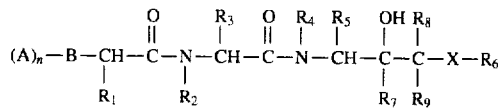

wherein $R_2$, $R_4$, $R_7$, $R_8$, and $R_9$ are hydrogen or lower alkyl, X is NH, O, S, SO, or $SO_2$, and $R_6$ is lower alkyl, cycloalkylalkyl, aryl, arylalkyl or an N-protecting group when X is NH.

Baran et al. in U.S. Pat. No. 4,657,931 disclose N-(acyl-dipeptidyl)-aminoglycol renin inhibitors including compounds of the formula

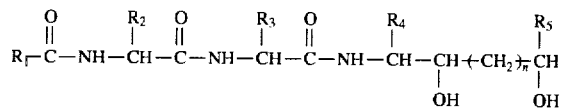

wherein $R_1$ is alkoxy or alkyl, $R_2$ is benzyl or naphthylmethyl, $R_3$ is alkyl or imidazolemethyl, $R_4$ is benzyl, $R_5$ is hydrogen or alkyl, and n is zero or one.

Luly et al. in U.S. Pat. No. 4,680,284 and European Patent Application 189,203 disclose diol renin inhibitors including those of the formula

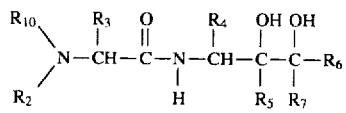

wherein $R_6$ includes hydrogen, lower alkyl, vinyl, aralkyl, and

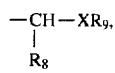

$R_8$ is hydrogen or lower alkyl, X is O, S, or NH, and $R_9$ is hydrogen, lower alkanoyl, or lower alkyl, or $XR_9$ is lower alkylsulphonyl, $N_3$ or Cl.

Luly et al. in European Patent Application 229,667 disclose renin inhibiting peptidylaminodiols including those of the formula

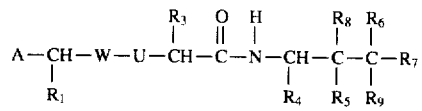

wherein W is

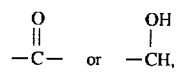

U is $CH_2$ or $NR_2$ provided that when W is

than U is $CH_2$, $R_4$ is alkyl, cycloalkylmethyl, or benzyl, $R_5$ is hydrogen, vinyl, formyl or $CH_2OH$, $R_7$ is hydrogen or alkyl, $R_8$ and $R_9$ are OH or $NH_2$, and $R_6$ is hydrogen, alkyl, vinyl, or aralkyl.

Rosenberg et. al in European Patent Application 230,266 disclose peptiaylaminodiol and triol renin inhibitors including those of the formula

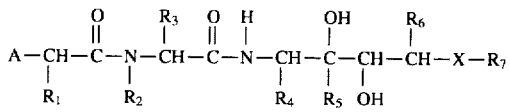

wherein $R_3$ is lower alkyl, benzyl, or heterocyclicmethyl, $R_4$ is lower alkyl, cycloalkylmethyl, or benzyl, $R_2$, $R_5$ and $R_6$ are hydrogen or lower alkyl, X is O, S, or NH, and $R_7$ is hydrogen, lower alkyl, alkanoyl alkylsulphonyl, or

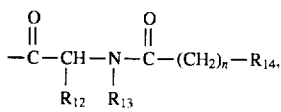

or $XR_7$ is lower alkylsulphonyl, $N_3$, or Cl.

Thaisrivongs in PCT Patent Application 87/05302A disclose renin inhibiting peptides including those of the formula

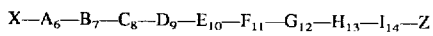

wherein $E_{10}$—$F_{11}$ is

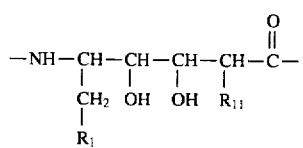

or

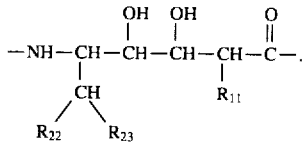

Hagenbach et al. in U.K. Patent application 2,200,115A disclose renin inhibitors of the formula

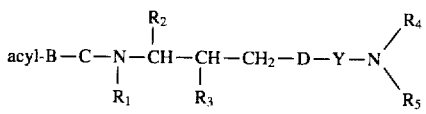

wherein Y can be $SO_2$; D can be a bond, NH, or CH—$R_1$; $R_3$ can be hydrogen, hydroxy, acyloxy, or $NH_2$; B and C are bonds or amino acids with at least one amino acid being present.

SUMMARY OF THIS INVENTION

This invention is directed to the renin inhibiting diol sulfonamides and sulfinyl compounds of formula I and salts thereof, to pharmaceutical compositions containing such active compounds, and to the method of using such compounds as well as novel intermediates and processes for preparing the compound of formula I.

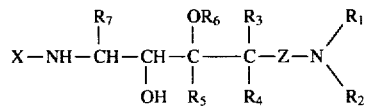

Z is SO or SO$_2$.

R$_1$ and R$_2$ are independently selected from hydrogen, alkyl of 1 to 7 carbons, alkenyl of 2 to 7 carbons, —(CH$_2$)$_m$-aryl, —(CH$_2$)$_m$-cycloalkyl, —(CH$_2$)$_m$-heterocyclo, halo substituted alkyl of 1 to 7 carbons, —(CH$_2$)$_g$—O—R$_{15}$,

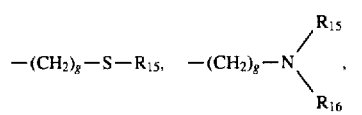

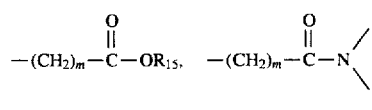

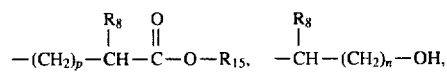

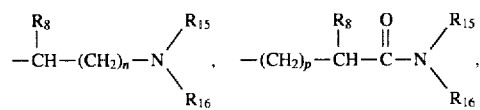

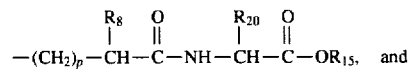

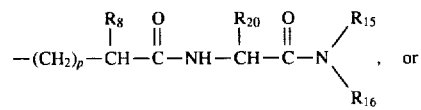

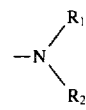

is a heterocyclic ring

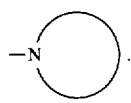

R$_3$, R$_7$, R$_8$, R$_{13}$, R$_{14}$ and R$_{20}$ are independently selected from hydrogen, alkyl of 1 to 7 carbons, halo substituted alkyl of 1 to 7 carbons, —(CH$_2$)$_m$-aryl, —(CH$_2$)$_m$-heterocyclo, —(CH$_2$)$_m$-cycloalkyl, —(CH$_2$)$_n$—O—R$_{15}$, —(CH$_2$)$_n$—S—R$_{15}$,

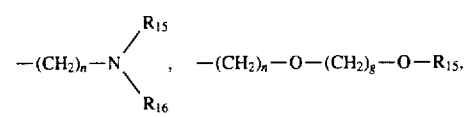

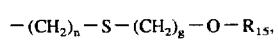

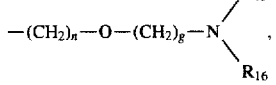

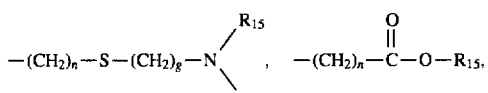

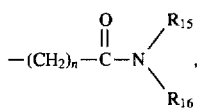

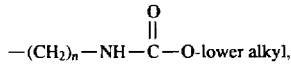

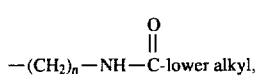

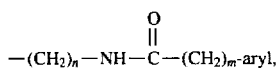

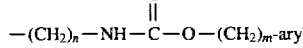

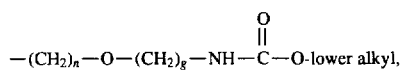

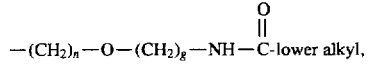

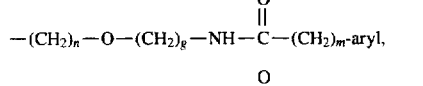

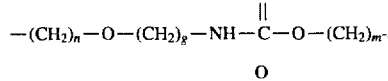

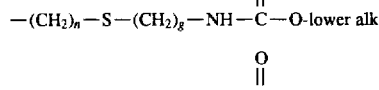

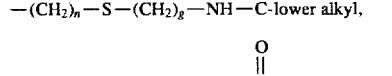

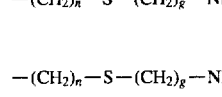

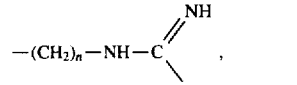

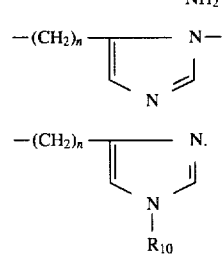

R$_4$ is hydrogen or alkyl of 1 to 7 carbons.

R$_5$ and R$_6$ are independently selected from hydrogen, alkyl of 1 to 7 carbons, halo substituted alkyl of 1 to 7 carbons, —(CH$_2$)$_m$-aryl, —(CH$_2$)$_m$-heterocyclo, and —(CH$_2$)$_m$-cycloalkyl.

R$_9$ is

—CH$_2$—O—CH$_2$—Ph   or   —CH$_2$—Ph.

R$_{10}$ is

—Ph(NO$_2$)(NO$_2$),   —C(=O)—O—CH$_2$—Ph,

—SO$_2$—Ph—CH$_3$,   —CH$_2$—Ph,   or

—CH$_2$—O—CH$_2$—Ph.

X is hydrogen,

—C(=O)—R$_{11}$,   —SO$_2$—R$_{11}$,   —CH(R$_{12}$)—R$_{21}$,

—Y—CH(R$_{13}$)—N(R$_{15}$)—W$_1$,   —Y—CH(R$_{13}$)—N(R$_{15}$)—C(=O)—CH(R$_{14}$)—N(R$_{16}$)—W$_1$,

—Y—CH(R$_{13}$)—O—W$_3$,   —Y—CH(R$_{13}$)—N(R$_{15}$)—C(=O)—CH(R$_{14}$)—CH$_2$—W$_2$,

—C(=O)—O—R$_{11}$,   —C(=O)—N(R$_{15}$)(R$_{16}$),   —SO$_2$—N(R$_{15}$)(R$_{16}$),   or

—Y—CH(R$_{13}$)—N(R$_{15}$)—C(=O)—CH(R$_{14}$)—O—W$_3$.

Y is —CH$_2$— or

—C(=O)—.

R$_{11}$ is alkyl of 1 to 7 carbons, hydroxy substituted alkyl of 1 to 7 carbons, aryl, heterocyclo, cycloalkyl, -alkylene-aryl, -alkylene-heterocyclo, -alkylene-cycloalkyl, —(CH$_2$)$_n$—C(=O)—O—R$_{15}$,   —(CH$_2$)$_n$—C(=O)—N(R$_{15}$)(R$_{16}$), -alkenyl-C(=O)—O—R$_{15}$,   or   -alkenyl-C(=O)—N(R$_{15}$)(R$_{16}$).

R$_{12}$ and R$_{21}$ are independently selected from hydrogen, alkyl of 1 to 7 carbons, hydroxy substituted alkyl of 1 to 7 carbons, aryl, heterocyclo, cycloalkyl, -alkylene-aryl, -alkylene-heterocyclo, -alkylene-cycloalkyl, —(CH$_2$)$_m$—C(=O)—O—R$_{15}$,   —(CH$_2$)$_m$—C(=O)—N(R$_{15}$)(R$_{16}$), -alkenyl-C(=O)—O—R$_{15}$,   and   -alkenyl-C(=O)—N(R$_{15}$)(R$_{16}$).

R$_{15}$ and R$_{16}$ are independently selected from hydrogen, alkyl of 1 to 7 carbons, —(CH$_2$)$_m$-cycloalkyl, —(CH$_2$)$_m$-aryl, and —(CH$_2$)$_m$-heterocyclo.

W$_1$ is hydrogen,

—C(=O)—O—(CH$_2$)$_m$—R$_{17}$,   —C(=O)—N(R$_{17}$)—(CH$_2$)$_m$—R$_{17}$ with (CH$_2$)$_{m'}$—R$_{17'}$, —C(=O)—(CH$_2$)$_m$—R$_{17}$,   —SO—R$_{18}$,   —SO$_2$—R$_{18}$,

—SO$_2$—NH$_2$,   —SO$_2$—N(R$_{18}$)(R$_{18'}$),   —SO$_2$—NH—R$_{18}$,

—(CH$_2$)$_m$—R$_{17}$,   or   —C(=O)—N(ring).

R$_{17}$ and R$_{17'}$ are independently selected from hydrogen, alkyl of 1 to 7 carbons, aryl, heterocyclo, and cycloalkyl.

W$_2$ is hydrogen, —R$_{18}$,

—C(=O)—R$_{18}$,   —C(=O)—O—R$_{18}$,   —C(=O)—NH$_2$,   —C(=O)—NH—R$_{18}$,

—C(=O)—N(R$_{18}$)(R$_{18'}$),   —SH,   —S—R$_{18}$,   —SO—R$_{18}$,

—SO$_2$—R$_{18}$,   —SO$_2$—NH$_2$,   —SO$_2$—NH—R$_{18}$,

—SO$_2$—N(R$_{18}$)(R$_{18'}$),   —S—C(=O)—R$_{18}$,   —P(=O)(CH$_2$)$_n$—R$_{17}$)((CH$_2$)$_{n'}$—R$_{17'}$),

-continued $$-\overset{O}{\underset{|}{\overset{\|}{P}}}-O-(CH_2)_n-R_{17}, \quad -\overset{O}{\underset{|}{\overset{\|}{P}}}-O-(CH_2)_n-R_{17}, \text{ or}$$
$$\overset{|}{(CH_2)_{n'}} \qquad \overset{|}{O}$$
$$\overset{|}{R_{17'}} \qquad \overset{|}{(CH_2)_{n'}}$$
$$\qquad \overset{|}{R_{17'}}$$

$$-\overset{O}{\overset{\|}{C}}-N\bigcirc .$$

$W_3$ is hydrogen, $-R_{18}$, $$-\overset{O}{\overset{\|}{C}}-R_{18}, \quad -\overset{O}{\overset{\|}{C}}-O-R_{18}, \quad -\overset{O}{\overset{\|}{C}}-NH_2, \quad -\overset{O}{\overset{\|}{C}}-NH-R_{18},$$

$$-\overset{O}{\overset{\|}{C}}-\underset{\underset{R_{18'}}{|}}{N}-R_{18}, \text{ or } -\overset{O}{\overset{\|}{C}}-N\bigcirc .$$

$R_{18}$ and $R_{18'}$ are independently selected from alkyl of 1 to 7 carbons, $-(CH_2)_m$-aryl, $-(CH_2)_m$-cycloalkyl, $-(CH_2)_m$-heterocyclo, $$-CH_2-\overset{O}{\overset{\|}{C}}-O-R_{17}, \quad -CH_2-\overset{O}{\overset{\|}{C}}-N\overset{R_{15}}{\underset{R_{16}}{\diagdown}},$$

$$-(CH_2)_n-NH-\overset{O}{\overset{\|}{C}}\text{-lower alkyl,}$$

$$-(CH_2)_n-NH-\overset{O}{\overset{\|}{C}}-O\text{-lower alkyl,}$$

$$-(CH_2)_n-NH-\overset{O}{\overset{\|}{C}}-O-(CH_2)_{n'}\text{-aryl,}$$

$$-(CH_2)_n-N\overset{R_{15}}{\underset{R_{16}}{\diagdown}}, \text{ or } -(CH_2)_n-NH-C\overset{NH}{\underset{NH_2}{\diagup}}.$$

the formula $$\bigcirc N-$$

represents a heterocyclic ring of the formula $$A\overset{(CH_2)_a}{\underset{(CH_2)_b}{\diagdown}}N-$$

wherein A is $-CH_2$, O, S, or $N-R_{19}$, a is an integer from 1 to 4 and b is an integer from 1 to 4 provided that the sum of a+b is an integer from 2 to 5 and such heterocyclic rings wherein one available carbon has a lower alkyl substituent.

$R_{19}$ is hydrogen, lower alkyl, $-(CH_2)_n$-phenyl, or $-(CH_2)_n$-cycloalkyl.

m and m' are independently selected from zero and an integer from 1 to 5.

n and n' are independently selected from an integer from 1 to 5.

p is zero or one.

g is an integer from 2 to 5.

DETAILED DESCRIPTION OF THE INVENTION

This invention in its broadest aspects relates to the compounds of formula I above, to compositions and methods of using such compounds to inhibit renin and thus produce a beneficial pharmaceutical effect, and to intermediates and processes useful in the preparation of such compounds.

The term alkyl of 1 to 7 carbons used in defining various symbols refers to straight or branched chain radicals having up to seven carbon atoms. The term lower alkyl refers to straight or branched radicals having up to four carbon atoms and is a preferred subgrouping for the term alkyl.

The term alkenyl used in defining various symbols refers to straight or branched radicals of 2 to 7 carbons containing at least one double bond. Preferred alkenyl groups are straight chain of 2 to 4 carbons containing one double bond.

The terms lower alkoxy and lower alkylthio refer to such lower alkyl groups as defined above attached to an oxygen or sulfur.

The term cycloalkyl refers to saturated rings of 4 to 7 carbon atoms with cyclopentyl and cyclohexyl being most preferred.

The term alkylene refers to a straight chain bridge of 1 to 5 carbons connected by single bonds, i.e., $-(CH_2)_n-$ wherein n is an integer of 1 to 5, such a straight chain bridge of 1 to 5 carbons wherein one or more hydrogens have been replaced by a lower alkyl group, i.e., $$-CH_2-\underset{\underset{CH_3}{|}}{CH}-CH_2-, \quad -CH_2-\underset{\underset{C_2H_5}{|}}{CH}-,$$

$$-CH_2-\underset{\underset{CH_3}{|}}{\overset{\overset{CH_3}{|}}{C}}-CH_2-CH_2-,$$

$$-CH_2-\underset{\underset{CH_3}{|}}{CH}-\underset{\underset{CH_3}{|}}{CH}-CH_2-, \text{ etc.,}$$

a hydroxy or hydroxy substituted lower alkyl group, i.e., $$-CH_2-\underset{\underset{OH}{|}}{CH}-CH_2-, \quad -CH_2-CH_2-\underset{\underset{OH}{|}}{CH}-,$$

$$-CH_2-\underset{\underset{\underset{OH}{|}}{CH_2}}{CH}-CH_2-, \quad -CH_2-\underset{\underset{\underset{CH_3}{|}}{CH-OH}}{CH}-CH_2-, \text{ etc.,}$$

amino or amino substituted lower alkyl group, i. e., $$-CH_2-\underset{\underset{NH_2}{|}}{CH}-CH_2-CH_2-, \quad -CH_2-CH_2-\underset{\underset{\underset{NH_2}{|}}{CH_2}}{CH}-,$$

$$-CH_2-\underset{\underset{\underset{CH_3}{|}}{CH-NH_2}}{CH}-CH_2-.$$

The term halogen refers to chloro, bromo, fluoro, and iodo.

The term halo substituted alkyl refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, diphenylmethyl, 1-naphthyl, 2-naphthyl, mono substituted phenyl, diphenylmethyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, diphenylmethyl, 1-naphthyl or 2-naphthyl wherein said substituents are selected from methyl, methoxy, methylthio, halogen, hydroxy and amino.

The term heterocyclo refers to fully saturated, partially saturated, or unsaturated rings of 5 or 6 atoms containing one or two O and S atoms and/or one to four N atoms provided that the total number of hetero atoms in the ring is 4 or less. The heterocyclo ring is attached by way of an available carbon atom. Preferred heterocyclo groups include 2-,3-, or 4-pyridyl, 2-pyrazinyl, 4-pyridazinyl, 4-imidazolyl, 4-thiazolyl, 2- and 3-thienyl, and 2- and 3-furyl. The term heterocyclo also includes bicyclic rings wherein the five or six membered ring containing O, S, and N atoms as defined above is fused to a benzene or pyridyl ring. A preferred bicyclic ring is 2-indolyl. The mono or bicyclic heterocyclic ring can also be additionally substituted at an available carbon atom by a lower alkyl of 1 to 4 carbons, halo substituted lower alkyl of 1 to 4 carbons, hydroxy, benzyl, or cyclohexylmethyl. Also, if the mono or bicyclic ring has an available N atom such N atom can also be substituted by an N-protecting group such as

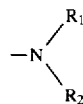,

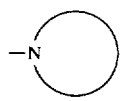

2,4-dinitrophenyl, lower alkyl, benzyl, or benzhydryl.

The products of formula I wherein X is hydrogen and $R_1$ and $R_2$ are selected from alkyl, alkylene, —(CH$_2$)$_m$-aryl, —(CH$_2$)$_m$-cycloalkyl, —(CH$_2$)$_m$-heterocyclo, and halo substituted lower alkyl or where

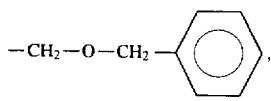

is a heterocyclic ring

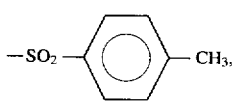

can be prepared by reacting an oxazolidinecarboxylic acid amide of the formula

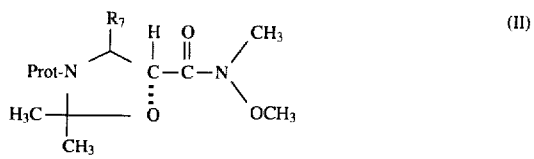

wherein Prot is an N-protecting group such as t-butoxycarbonyl with the amide of the formula

in the presence of n-butyllithium to give

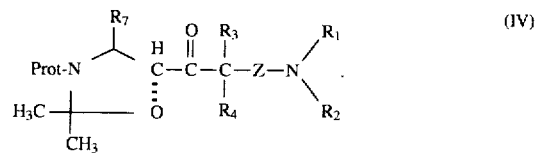

The oxazolidine ketone intermediate of formula IV is then treated with a reducing agent such as borane tert-butylamine complex to give

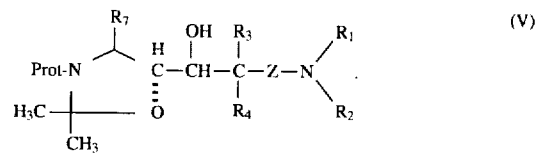

This oxazolidine alcohol is then subjected to acid hydrolysis to give the diol

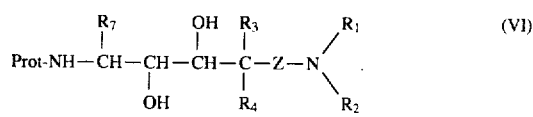

Removal of the N-protecting group from the diol of formula VI such as by treatment with HCl when Prot is t-butoxycarbonyl yields the desired products of formula I.

The products of formula I wherein X is hydrogen and one of $R_1$ and $R_2$ is hydrogen and the other is E wherein E is —(CH$_2$)$_g$—O—R$_{15}$, —(CH$_2$)$_g$—S—R$_{15}$,

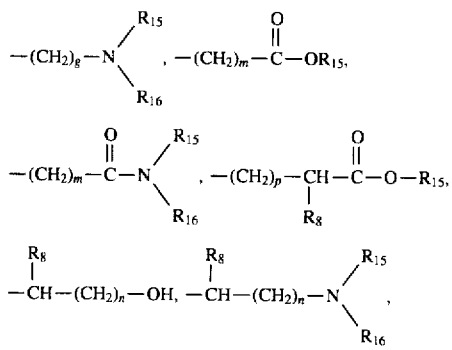

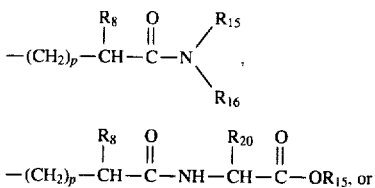

-continued $$-(CH_2)_p-\underset{\underset{R_8}{|}}{CH}-\underset{\underset{}{\overset{O}{\|}}}{C}-NH-\underset{\underset{R_{20}}{|}}{CH}-\underset{\underset{}{\overset{O}{\|}}}{C}-N\underset{R_{16}}{\overset{R_{15}}{\diagup}}$$

can be prepared by reacting the oxazolidinecarboxylic acid amide of formula II with the amide of the formula $$\underset{\underset{R_3}{|}}{\overset{R_4}{|}}HC-Z-NH-CH\left(\bigcirc\right)_2 \quad (VII)$$

to give $$\text{Prot-N}\underset{CH_3}{\overset{R_7}{\underset{|}{\diagup}}}\underset{\underset{O}{\vdots}}{\overset{H}{\overset{|}{C}}}-\overset{O}{\overset{\|}{C}}-\underset{\underset{R_4}{|}}{\overset{R_3}{|}}C-Z-NH-CH\left(\bigcirc\right)_2 \quad (VIII)$$

The intermediate of formula VIII is then treated with a reducing agent as described previously to give $$\text{Prot-N}\underset{CH_3}{\overset{R_7}{\underset{|}{\diagup}}}\underset{\underset{O}{\vdots}}{\overset{H}{\overset{|}{C}}}-\overset{OH}{\overset{|}{CH}}-\underset{\underset{R_4}{|}}{\overset{R_3}{|}}C-Z-NH-CH\left(\bigcirc\right)_2 \quad (IX)$$

This intermediate is alkylated with

Hal—E    (X)

wherein Hal is Br or I to give $$\text{Prot-N}\underset{CH_3}{\overset{R_7}{\underset{|}{\diagup}}}\underset{\underset{O}{\vdots}}{\overset{H}{\overset{|}{C}}}-\overset{OH}{\overset{|}{CH}}-\underset{\underset{R_4}{|}}{\overset{R_3}{|}}C-Z-\overset{E}{\overset{|}{N}}-CH\left(\bigcirc\right)_2 \quad (XI)$$

The oxazolidine alcohol of formula XI is then hydrogenated for example by treatment with platinum hydroxide and hydrogen gas to give $$\text{Prot- N}\underset{CH_3}{\overset{R_7}{\underset{|}{\diagup}}}\underset{\underset{O}{\vdots}}{\overset{H}{\overset{|}{C}}}-\overset{OH}{\overset{|}{CH}}-\underset{\underset{R_4}{|}}{\overset{R_3}{|}}C-Z-NH-E. \quad (XII)$$

Acid hydrolysis and removal of the N-protecting group as described previously gives the desired final products of formula I wherein X is hydrogen, $R_1$ is E, and $R_2$ is hydrogen.

The intermediate of formula XII can be alkylated with

Hal—$R_2$    (XIII)

wherein $R_2$ is other than hydrogen to give $$\text{Prot- N}\underset{CH_3}{\overset{R_7}{\underset{|}{\diagup}}}\underset{\underset{O}{\vdots}}{\overset{H}{\overset{|}{C}}}-\overset{OH}{\overset{|}{CH}}-\underset{\underset{R_4}{|}}{\overset{R_3}{|}}C-Z-N\underset{R_2}{\overset{E}{\diagup}} \quad (XIV)$$

Acid hydrolysis and removal of the N-protecting group as described previously gives the desired final products of formula I wherein X is hydrogen, $R_1$ is E, and $R_2$ is other than hydrogen.

When $R_2$ is methyl one can employ methyl iodide as the alkylation agent as described above or instead of the halide one can employ dimethyl sulfate.

It should be appreciated that certain groups within the definition of E may require a modification in the above general procedure. For example, when $R_1$ is $$-(CH_2)_p-\underset{\underset{R_8}{|}}{CH}-\overset{O}{\overset{\|}{C}}-OH$$

the bromide or iodide of formula X would be a carboxylic acid ester. This ester would then be saponified by treatment with sodium hydroxide in methanol/water as the last step in the synthesis to give the final product where $R_1$ is $$-(CH_2)_p-\underset{\underset{R_8}{|}}{CH}-\overset{O}{\overset{\|}{C}}-OH.$$

Similarly, the compounds where $R_1$ is $$-(CH_2)_p-\underset{\underset{R_8}{|}}{CH}-\overset{O}{\overset{\|}{C}}-N\underset{R_{16}}{\overset{R_{15}}{\diagup}},$$

$$-(CH_2)_p-\underset{\underset{R_8}{|}}{CH}-\overset{O}{\overset{\|}{C}}-NH-\underset{\underset{R_{20}}{|}}{CH}-\overset{O}{\overset{\|}{C}}-OR_{15}, \text{etc.},$$

are prepared by coupling the protected amine or amino acid to the compounds where $R_1$ is $$-(CH_2)_p-\underset{\underset{R_8}{|}}{CH}-\overset{O}{\overset{\|}{C}}-OH$$

to form the amide bond. This type of chemistry is well known and can involve the use of a coupling agent such as dicyclohexylcarbodiimide or conversion of the carboxylic acid to an activated form such as an acid halide, activated ester, etc.

The compounds of formula I wherein $R_1$ and $R_2$ are both hydrogen and X is hydrogen can be prepared by reacting an oxazolidinecarboxylic acid of formula V wherein $R_1$ is $$-CH_2-\underset{\underset{OCH_3}{}}{\left(\bigcirc\right)}-OCH_3$$

and $R_2$ is hydrogen with 2,3-dichloro-5,6-dicyano-1,4-benzoquinone to give $$\text{Prot- N}\underset{CH_3}{\overset{R_7}{\underset{|}{\diagup}}}\underset{\underset{O}{\vdots}}{\overset{H}{\overset{|}{C}}}-\overset{OH}{\overset{|}{CH}}-\underset{\underset{R_4}{|}}{\overset{R_3}{|}}C-Z-N=CH-\left(\bigcirc\right)\underset{OCH_3}{\overset{OCH_3}{\diagdown}}. \quad (XIV)$$

Treatment with 10% HCl and acetic acid in tetrahydrofuran gives the desired product of formula I wherein $R_1$ and $R_2$ are both hydrogen and X is hydrogen.

The compounds of formula I wherein $R_5$ is other than hydrogen can be prepared by reacting the amide of formula III with an oxazolidineketone of the formula

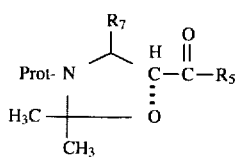

in the presence of n-butyl lithium to give

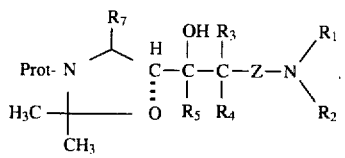

Acid hydrolysis and removal of the protecting group gives the final products of formula I wherein $R_5$ is other than hydrogen.

The products of formula I wherein X is —Y-substituent and Y is

can be prepared by coupling the acid of formula

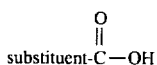

to the compound of formula I wherein X is hydrogen. This coupling reaction is preferably performed in the presence of a coupling agent such as ethyl-3-(3-dimethylamino)propyl carbodiimide or dicyclohexylcarbodiimide.

The products of formula I wherein X is —Y-substituent and Y is —CH$_2$— can be prepared by treating the corresponding products where Y is

with a reducing agent such as BH$_3$ . dimethylsulfide as the last step of the synthesis.

The products of formula I wherein X is —SO$_2$—R$_{11}$ or

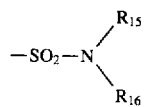

can be prepared by reacting the sulfonyl chloride of the formula

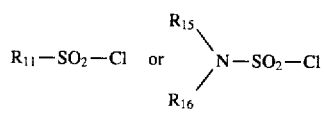

with the compound of formula I wherein X is hydrogen.

The products of formula I wherein X is

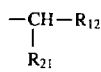

can be prepared by reacting the ketone of the formula

with the compound of formula I wherein X is hydrogen. This reaction is performed in the presence of sodium cyanoborohydride at neutral pH.

In the above reactions if any of the $R_1$, $R_2$, $R_3$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, $R_{20}$ or $R_{21}$ has a hydroxyl, amino, imidazolyl, mercaptan or guanidinyl function, then that moiety should be protected until the last step of the synthesis. Suitable protecting groups include benzyloxycarbonyl, t-butoxycarbonyl, benzyl, benzhydryl, trityl, etc., and nitro in the case of guanidinyl. The protecting group is removed by known methods following completion of the reaction.

The starting material of formula II can be prepared by reacting an N-protected amino acid of the formula

with N,O-dimethylhydroxylamine hydrochloride in the presence of a coupling agent such as 1,1'-carbonyldiimidazole to give

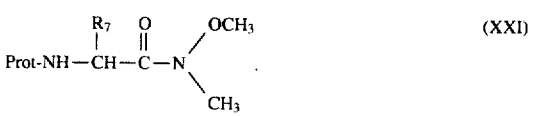

The compound of formula XXI is reduced with lithium aluminum hydride to give the aldehyde of the formula

The aldehyde of formula XXII is reacted with furan in the presence of an alkyllithium and zinc bromide to give the alcohol of the formula

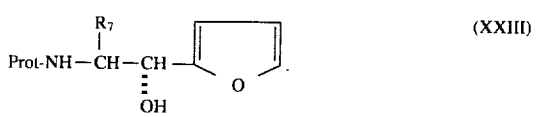

Treatment of the alcohol of formula XXIII with 2,2-dimethoxypropane in the presence of acid gives the oxazolidine of the formula

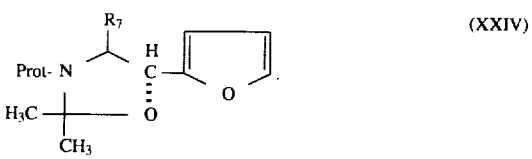

Oxidation with ruthenium tetroxide generated from a mixture of sodium metaperiodate and ruthenium trichloride gives the oxazolidine of the formula

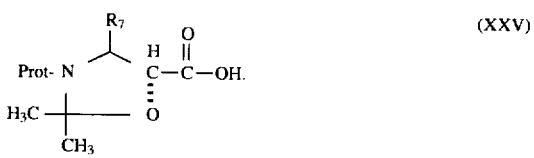

Treatment of the oxazolidine carboxylic acid of formula XXV with N,O-dimethylhydroxylamine hydrochloride in the presence of a coupling agent gives the starting material of formula II.

Preferred compounds of this invention are those of formula I wherein:

Z is $SO_2$.

$R_1$ and $R_2$ are both hydrogen;

$R_1$ is straight or branched chain alkyl of 1 to 7 carbons, alkenyl of 2 to 4 carbons having a single double bond, $$-\underset{\underset{R_8}{|}}{CH}-(CH_2)_n-OH, \quad -(CH_2)_p-\underset{\underset{R_8}{|}}{CH}-\underset{\underset{}{\overset{O}{\|}}}{C}-OH, \quad or$$

$$-(CH_2)_p-\underset{\underset{R_8}{|}}{CH}-\underset{\underset{}{\overset{O}{\|}}}{C}-O-\text{ alkali metal salt ion}$$

and $R_2$ is hydrogen or benzyl.

$R_8$ is hydrogen or straight or branched chain alkyl of 1 to 7 carbons.

$R_3$ is hydrogen or straight or branched chain alkyl of 1 to 7 carbons.

$R_4$ is hydrogen or straight or branched chain alkyl or 1 to 7 carbons.

$R_5$ is hydrogen or straight or branched chain alkyl of 1 to 7 carbons.

$R_6$ is hydrogen or straight or branched chain alkyl of 1 to 7 carbons.

$R_7$ is $-(CH_2)_n$-cycloalkyl.

X is hydrogen, straight or branched chain alkyl of 1 to 7 carbons, $$-\overset{O}{\underset{\|}{C}}-R_{11}, \quad -\overset{O}{\underset{\|}{C}}-O-R_{11}, \quad -SO_2-R_{11},$$

$$-Y-\underset{\underset{R_{13}}{|}}{CH}-NH-W_1,$$

$$-Y-\underset{\underset{R_{13}}{|}}{CH}-NH-\overset{O}{\underset{\|}{C}}-\underset{\underset{R_{14}}{|}}{CH}-NH-W_1,$$

$$-Y-\underset{\underset{R_{13}}{|}}{CH}-NH-\overset{O}{\underset{\|}{C}}-\underset{\underset{R_{14}}{|}}{CH}-CH_2-W_2,$$

$$-Y-\underset{\underset{R_{13}}{|}}{CH}-O-W_3, \quad or \quad -Y-\underset{\underset{R_{13}}{|}}{CH}-NH-SO_2-R_{18}.$$

Y is $$-\overset{O}{\underset{\|}{C}}- \quad or \quad -CH_2-.$$

$R_{11}$ is straight or branched chain alkyl of 1 to 7 carbons, aryl, heterocyclo, -alkylene-aryl, -alkylene-heterocyclo, or $$-CH=CH-\overset{O}{\underset{\|}{C}}-O-\text{ lower alkyl}.$$

$R_{13}$ is straight or branched chain alkyl of 1 to 7 carbons or $-(CH_2)_m$-heterocyclo.

$R_{14}$ is $-(CH_2)_m$-aryl or straight or branched chain alkyl of 1 to 7 carbons.

$W_1$ and $W_3$ are independently selected from hydrogen $$-\overset{O}{\underset{\|}{C}}-(CH_2)_m-R_{17}, \quad and \quad -\overset{O}{\underset{\|}{C}}-N\bigcirc$$

or $W_1$ is $-SO_2-R_{18}$.

$$-\underset{\underset{\underset{\underset{R_{17'}}{|}}{(CH_2)_{n'}}}{|}}{\overset{\overset{\overset{\overset{O}{\|}}{}}{}}{P}}-O-(CH_2)_n-R_{17}, \quad or \quad -\overset{O}{\underset{\|}{C}}-N\bigcirc.$$

$R_{17}$ and $R_{17'}$ are independently selected from straight or branched chain alkyl of 1 to 7 carbons, aryl, or heterocyclo.

$R_{18}$ is straight or branched chain alkyl of 1 to 7 carbons or $-(CH_2)_m$-aryl.

aryl is phenyl, diphenylmethyl, 1-naphthyl, 2-naphthyl, mono substituted phenyl wherein said substituent is lower alkyl of 1 to 4 carbons, lower alkoxy of 1 to 4 carbons, lower alkylthio of 1 to 4 carbons, hydroxy, amino, Cl, Br, or F, or disubstituted phenyl wherein said substituents are selected from methyl, methoxy, methylthio, Cl, Br, F, hydroxy and amino.

Within the preferred definition of $R_{11}$ heterocyclo is 2-, 3-, or 4-pyridinyl, 6-hydroxy-3-pyridinyl, 4-pyridazinyl, or 2-pyrazinyl.

Within the preferred definition of $R_{13}$ heterocyclo is

[structures of imidazole NH and thiazole N]

Within the preferred definition of $R_{17}$ heterocyclo is

[indole structure with NH]

2-, 3-, or 4-pyridyl.

Within the preferred definition of $W_1$, $W_2$, and $W_3$ $$-N\bigcirc \quad is \quad -N\diagup\hspace{-4pt}\diagdown O, \quad -N\diagup\hspace{-4pt}\diagdown NH \quad or$$

$$-N\diagup\hspace{-4pt}\diagdown N-CH_3.$$

Most preferred are the compounds of formula I wherein
Z is $SO_2$.
$R_1$ is n-butyl or $-CH_2-CH_2-CH=CH$.
$R_2$ is hydrogen.
$R_3$ is hydrogen or methyl, especially hydrogen.
$R_4$ is hydrogen.
$R_5$ is hydrogen.
$R_6$ is hydrogen.
$R_7$ is $$-CH_2-\bigcirc.$$

X is hydrogen, straight or branched chain alkyl of 1 to 7 carbons,

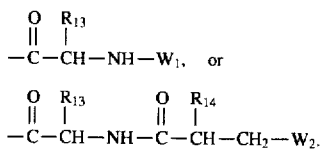

$R_{13}$ is —$CH_2CH(CH_3)_2$ or

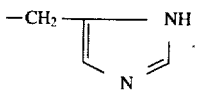

$W_1$ is

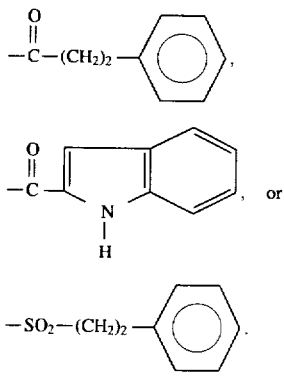

$R_{14}$ is

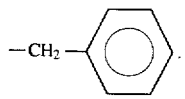

$W_2$ is —$SO_2$—C $(CH_3)_3$.

The compounds of formula I form salts with a variety of inorganic and organic acids. The non-toxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates or in aqueous medium and then lyophilizing.

Additionally, the compounds of formula I wherein $R_1$ or $R_2$ terminate in a carboxylic acid moiety form pharmaceutical salts with alkali metals such as sodium, potassium, and lithium and alkaline earth metals such as calcium and magnesium. These salts are obtained by reacting the acid form of the compound of formula I with the desired metal ion in a medium in which the salt precipitates or in an aqueous medium and then lyophilizing.

The compounds of formula I contain several asymmetric centers depending upon the definition of $R_3$, $R_4$, $R_5$, $R_7$, $R_8$, $R_{12}$, $R_{13}$, $R_{14}$, and $R_{21}$. Thus, the compounds of formula I can exist in diastereoiosmeric forms or in mixtures thereof. The above described processes can utilize racemates, enantiomers or diastereomers as starting materials. When diastereomeric products are prepared, they can be separated by conventional chromatographic or fractional crystallization methods.

The compounds of this invention including pharmaceutically acceptable salts thereof are useful cardiovascular agents. They inhibit the conversion of angiotensinogen to angiotensin I and therefore are useful in reducing or relieving angiotensin related disorders. The action of the enzyme renin on angiotensinogen produces angiotensin I which in turn is converted by the angiotensin converting enzyme (ACE) to angiotensin II. The latter is an active pressor substance which has been implicated as the causative agent in several forms of hypertension and other cardiovascular disorders in mammalian species, e.g. humans. The compounds of this invention intervene in the angiotensinogen→(renin)→angiotensin I→(ACE)→angiotensin II sequence by inhibiting renin and reducing or eliminating the formation of the pressor substance angiotensin II.

As a result of this action, the compounds of this invention possess useful antihypertensive activity and are useful in any situation where the reduction of the levels of circulating angiotensin II would be beneficial. For example, the compounds of this invention are also useful in the treatment of congestive heart failure, renin dependent hypoaldosteronism, myocardial infarction, and renal disorders such as diabetic nephropathy. These compounds may also be useful as adjuncts in the treatment of other disorders such as glaucoma and scleroderma and as a diagnostic agent in determining the presence of renin related disorders such as hypertension.

Thus, the administration of a composition containing one (or a combination) of the compounds of this invention is useful in treating the angiotensin related disorders described above. For example, the daily administration of from about 0.5 to about 100 mg/kg of body weight in a single dose or divided into two to four doses is useful in reducing blood pressure in humans. Of course, the exact dose employed will vary according to the compound selected and the method of administration, i.e., the preferred intravenous dose is below about 1 mg/kg/day and the preferred oral dose is from about 10 to about 50 mg/kg/day. In addition to oral and intravenous forms of administration, the compounds of this invention can be formulated in compositions suitable for subcutaneous, transdermal, intramuscular, or intranasal administration. Suitable oral compositions include tablets, capsules, and elixirs and suitable parenteral compositions include sterile solutions or suspensions. From about 10 to about 100 mg. of a compound of this invention is formulated with one or more physiologically acceptable vehicles, carriers, excipients, binders, preservatives, stabilizers, flavoring agents, etc. in a unit dose form as called for by accepted pharmaceutical practice.

The compounds of this invention are additionally useful when employed in combination with one or more others pharmaceutically active cardiovascular agents. Such combination may be employed as a fixed dose combination or as separate doses administered concomitantly. Examples of suitable cardiovascular agents include diuretics such as the thiazide diuretics, e.g., chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, delapril, pentopril, quinapril, ramipril, lisinopril, and salts of such compounds, a thromboxane synthetase inhibitor, a thromboxane receptor antagonist, a calcium channel blocking agent such as diltiazem, nifedipine, etc., a potassium channel activator, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), α- and β-adrenergic receptor blocking agents such as propanolol, nadolol, metoprolol, etc., antifibrillatory agents, neutral endopeptidase inhibitors, cardiotonic agents, etc. Such combination products if formulated as a fixed dose employ the compounds of this invention within the dose range described above and other pharmaceutically active agent within its approved dose range.

In addition to the above described renin inhibition activity, the compounds of this invention are also inhibitors of retroviral protease. It has been shown that retroviral protease activity is essential to the infectivity of the virus. Thus, the inhibition of such protease may provide a means of inhibiting the ability of such virus to replicate and may be useful in treating diseases caused by retrovirus including HTLV-I and HTLV-III. A suitable dose for this purpose would be from about 1 to about 500 mg/kg/day.

The following examples are illustrative of the invention. Temperatures are given in degrees centigrade.

EXAMPLE 1

[DR-(βR*,αR*,δS*)]-δ-Amino-N-butyl-β,α-dihydroxy-cyclohexanepentanesulfonamide, monohydrochloride a) N-Butylmethanesulfonamide Methanesulfonyl chloride (6.76 ml., 87.3 mmole, 1.0 eq.) was dissolved in distilled dichloromethane (44 ml., 0.5M). The solution was cooled in an ice bath and treated dropwise with n-butylamine (17.3 ml., 175 mmole, 2.0 eq.). After the addition was complete, the clear solution was stirred overnight at room temperature. The mixture was diluted with chloroform (200 ml.), dried, washed with 0.5N HCl (2×200 ml.) and saturated NaCl solution (200 ml.), dried (MgSO$_4$) and freed of solvent in vacuo leaving an oil. This was purified by distillation to give N-butylmethanesulfonamide (11.4 g., 86%,. b.p. 106°–110°/0.5 mm) which solidified on standing.

b) (4S-trans)-4-(Cyclohexylmethyl)-5-[[(methoxy)methylamino]carbonyl]-2,2-dimethyl-3-oxazolidinecarboxylic acid, 1,1-dimethylethyl ester To a solution of [(1,1-dimethylethoxy)carbonyl]-L-phenylalanine (120 g., 452 mmole) in absolute ethanol (1 l.) was added platinum oxide catalyst (5 g., Adams' catalyst). The mixture was placed on a Parr reduction apparatus at 50 lbs. pressure. The absorption of hydrogen was rapid and the hydrogen reservoir needed continued refilling. The reduction proceeded overnight and after 20 hours TLC on silica gel (eluted with 4:1 toluene:acetic acid) showed the absence of starting material with a new spot at $R_f$=0.62. The mixture was filtered through Celite and concentrated in vacuo to give 124.4 g. of (S)-α-[[(1,1-dimethylethoxy)carbonyl]amino]cyclohexanepropanoic acid as a glassy solid, colorless residue. $[\alpha]_D$=−9.5° (c=1, methanol). TLC(silica gel; 4:1, toluene:acetic acid) $R_f$=0.62.

Anal. calc'd. for $C_{14}H_{25}NO_4$: C, 61.97; H, 9.29; N, 5.16 Found: C, 61.84; H, 9.25; N, 5.12.

To a solution of (S)-α-[[(1,1-dimethylethoxy)carbonyl]amino]cyclohexanepropanoic acid (93 g., 343 mmole) in dry tetrahydrofuran (1 l.) was added a 20% molar excess of 1,1'-carbonyldiimidazole over a period of less than 10 minutes with very efficient stirring to keep the internal temperature below 30°. After stirring for 30 minutes, N,O-dimethylhydroxylamine hydrochloride (36.8 g., 377 mmole) was added, followed by triethylamine (38.2 g., 377 mmole). After stirring at room temperature for 4 hours, the reaction mixture was filtered and the resulting filtrate was concentrated in vacuo. The amber colored residue (100 g.) was dissolved in ether (900 ml.) and poured into 1N HCl (1 l.). The acidic aqueous phase was separated, further extracted with ether and the combined ethereal solutions were washed with water, saturated sodium bicarbonate, water, and brine, then dried (MgSO$_4$) to give (S)-α-[[(1,1-dimethylethoxy)carbonyl]amino]-N-methoxy-N-methylcyclohexanepropanamide as a colorless oil. $[\alpha]_D$=−12.9° (c=1, methanol). TLC (silica gel; 1:1, ethyl acetate:hexanes) $R_f$=0.58.

Anal. calc'd. for $C_{16}H_{30}N_2O_4$: C, 61.11; H, 9.62; N, 8.91 Found: C, 61.35; H, 9.54; N, 9.10.

(S)-α-[[(1,1-Dimethylethoxy)carbonyl]amino]-N-methoxy-N-methylcyclohexanepropanamide (55.3 g., 175.9 mmole, 1 eq.) was dissolved in diethyl ether (1760 ml., 0.1M) and cooled in an ice bath. A solution of lithium aluminum hydride in tetrahydrofuran (193 ml., 193 mmole, 1.1 eq., 1M in tetrahydrofuran) was added dropwise over 90 minutes. After 75 minutes, a 1N HCl solution (1 l.) was added cautiously and slowly. The cooling bath was removed and the mixture was stirred for 2 hours. The layers were separated and the aqueous layer was reextracted with ether (2×400 ml.). The combined ether layers were dried (MgSO$_4$) and freed of solvent in vacuo leaving a viscous oil (46.47 g.). This was chromatographed on silica gel (500 g., Merck) which was packed in hexane. The aldehyde was eluted with ether:hexane (1:1) to give (S)-α-[[(1,1dimethylethoxy)carbonyl]amino]cyclohexanepropanal.

n-Butyl lithium (210 ml., 525 mmole, 3.2 eq., 2.5M in hexane) was added to a solution of furan (38.1 ml., 524 mmole, 3.2 eq.) in distilled tetrahydrofuran (524 ml., 1M) at −78°. The mixture was stirred at −78° for 15 minutes. The cooling bath was then removed and stirring was continued for 45 minutes. The mixture was cooled to 0°. Zinc bromide (524 ml. of a 1M solution in tetrahydrofuran, 524 mmole, 3.2 eq.) was added by cannula. After 15 minutes, the mixture was cooled to −78° and a solution of (S)-α-[[(1,1dimethylethoxy)carbonyl]amino]cyclohexanepropanal (41.8 g., 163.7 mmole, 1.0 eq.) in tetrahydrofuran (250 mi., 0.65M) was added. The cooling bath was removed and the progress of the reaction was followed by TLC. After six hours, the reaction was quenched by the addition of aqueous saturated ammonium chloride (840 ml.) and extracted with ether (3×500 ml.). The organic extracts were dried (Na$_2$SO$_4$), filtered through MgSO$_4$ and freed of solvent in vacuo leaving a viscous oil. This was chromatographed on silica gel (Merck, 1500 g.) eluting with ether:hexane (3:5 followed by 1:1) to give [R-(R*,S*)-β-[[(1,1-dimethylethoxy)carbonyl]amino]-α-(2-furanyl)cyclohexanepropanol as a very viscous oil. TLC (silica gel; 1:1 ether:hexane) $R_f$=0.32.

[R-(R*,S*)]-β-[[(1,1-Dimethylethoxy)carbonyl]amino]-α-(2-furanyl)cyclohexanepropanol (41.63 g., 128.9 mmole, 1 eq.) was dissolved in distilled dichloromethane (1 l., 0.129M) under an argon atmosphere. 2,2-Dimethoxypropane (158.5 ml., 1289 mmole, 10 eq.) was added. The solution was cooled in an ice bath and pyridinium toluene-4-sulfonate (3.24 g., 12.89 mmole, 0.1 eq.) was added. The cooling bath was removed and the mixture was stirred at room temperature for 24 hours. Additional 2,2-dimethoxypropane (50 ml., 407 mmole, 3.2 eq.) and pyridinium toluene-4-sulfonate (1.5 g., 6.0 mmole, 0.05 eq.) were added and stirring at room temperature was continued for 20 hours. Solid sodium bicarbonate was added and the solvent was removed in vacuo. The residue was dissolved in ether (1 l.) and washed with saturated sodium bicarbonate solution (300 ml.) and saturated sodium chloride solution (300 ml.), dried (MgSO$_4$) and freed of solvent in vacuo leaving a yellow oil (47.04 g.). This was chromatographed on silica gel (Merck, 1300 g.) eluting with ether:hexane (1:9) to give (4S-trans)-4-(cyclohexylmethyl)-5-(2-furanyl)-2,2-dimethyl-3 -oxazolidinecarboxylic acid, 1,1-dimethylethyl ester as a colorless oil which crystallized on standing (36.66 g., 78.3%), m.p. 52°–56°. $[\alpha]_D=-46.9°$ (c=1.6, methanol). TLC (silica gel, 1:3, ether:hexane) $R_f=0.58$.

(4S-trans)-4-(Cyclohexylmethyl)-5-(2-furanyl)-2,2 -dimethyl-3-oxazolidinecarboxylic acid, 1,1dimethylethyl ester (36.66 g., 101 mmole, 1.0 eq.) was dissolved in tetrachloromethane (200 ml., 0.5M), acetonitrile (200 ml., 0.5M) and water (300 ml., 0.33M). While stirring vigorously with a mechanical stirrer and cooling in a cold water bath, sodium metaperiodate (88.6 g., 414 mmole, 4.1 eq.) and ruthenium trichloride .3 $H_2O$ (900 mg., 3.4 mmole, 0.03 eq.) were added. The mixture was stirred rapidly at room temperature. After 7.5 hours, additional acetonitrile (200 ml.), tetrachloromethane (200 ml.), water (300 ml.) and sodium metaperiodate (21.4 g., 100 mmole, 1.0 eq.) were added and stirring was continued for 16 hours. The solid was removed by filtration and washed with dichloromethane (500 ml.). The layers were separated and the aqueous layer was reextracted with dichloromethane (2×300 ml.). The combined organic layers were dried ($MgSO_4$) and freed of solvent in vacuo leaving an olive-green solid. This was chromatographed on silica gel (Merck, 1300 g.) eluting with 1–2% methanol and 0.2% acetic acid in dichloromethane to give 27.59 g. of a pale yellow solid. A small sample was recrystallized from 1.3% ethyl acetate in hexane (75 ml.) to give an analytical sample of crystalline (4S-trans)-4 -(cyclohexylmethyl)-2,2-dimethyl-3,5-oxazolidinedicarboxylic acid, 3-(1,1-dimethylethyl)ester; m.p. 147°–151°; $[\alpha]_D=-16.9°$ (c=1.0, methanol). TLC (silica gel; 4% methanol in dichloromethane containing 0.2% acetic acid) $R_f=0.35$.

Anal. calc'd. for $C_{18}H_{31}NO_5$: C, 63.32; H, 9.15; N, 4.10 Found: C, 63.33; H, 9.09; N, 4.33.

1,1'-Carbonyldiimidazole (1.40 g., 8.6 mmole, 1.2 eq.) was added to a solution of (4S-trans)-4 -(cyclohexylmethyl)-2,2-dimethyl-3,5-oxazolidinedicarboxylic acid, 3-(1,1-dimethylethyl)ester (2.45 g., 7.18 mmole, 1.0 eq.) in tetrahydrofuran (48 ml., 0.15M) at room temperature. The reaction was stirred for 30 minutes, N,O-Dimethylhydroxylamine hydrochloride (980 mg., 10.0 mmole, 1.4 eq.) and triethylamine (1.5 ml., 10.8 mmole, 1.5 eq.) were then added and the reaction was stirred overnight at room temperature. The mixture was then poured into 1N HCl (60 ml.) and extracted with ether (2×100 ml.). The organic extracts were washed with aqueous saturated sodium bicarbonate (60 ml.), dried ($MgSO_4$), filtered, and freed of solvent in vacuo. The product was chromatographed on silica gel (Merck, 150 g.) eluting with ether:hexane (1:3) to give 1.945 g. of (4S-trans)-4-(cyclohexylmethyl)-5-[[(methoxy)methylamino]carbonyl]-2,2-dimethyl-3-oxazolidinecarboxylic acid, 1,1-dimethylethyl ester; m.p. 75°–77°; $[\alpha]_D=+5.7°$ (c=0.9, methanol).

c) (4S-trans)-5-[[(Butylamino)sulfonyl]acetyl]-4 -(cyclohexylmethyl)-2,2-dimethyl-3-oxazolidinecarboxylic acid, 1,1-dimethylethyl ester The product from part (a) (737 mg., 4.88 mmole, 2.5 eq.) was dissolved in distilled tetrahydrofuran (24.4 ml., 0.2M) under an argon atmosphere. The solution was cooled to –40° to –45° and a 2.5M solution of n-butyl lithium in hexane (3.9 ml., 9.75 mmole, 5 eq.) was added dropwise. The mixture was stirred at –40° for 30 minutes. The product from part (b) (750 mg., 1.95 mmole, 1 eq.) was added as a solid. The mixture was stirred at –40° for 75 minutes and then quenched with saturated $NH_4Cl$ solution (5 ml.). The mixture was allowed to warm to room temperature and then made strongly acidic with 1N HCl. The product was extracted into chloroform (2×50 ml.), dried ($MgSO_4$), and freed of solvent in vacuo. The remaining material was chromatographed on silica gel (Merck, 70 g.), eluting with ether:hexane (1:2) to give 589 mg. of (4S-trans)-5-[[(butylamino)sulfonyl]acetyl]-4-(cyclohexylmethyl) -2,2-dimethyl-3-oxazolidinecarboxylic acid, 1,1-dimethylethyl ester as a waxy solid; m.p. 70°–73°; $[\alpha]_D=+33.3°$ (c=0.6, methanol). TLC (silica gel; ether:hexane, 2:1) $R_f=0.66$.

d) [4S-[4α,5β(S*)]]-and [4S-[4α,5β(R*)]]-5-[2 -[(Butylamino)sulfonyl]-1-hydroxyethyl]-4-(cyclohexylmethyl) -2,2-dimethyl-3-oxazolidinecarboxylic acid, 1,1-dimethylethyl ester The product from part (c) (585 mg., 1.23 mmole, 1 eq.) was dissolved in anhydrous ethyl ether (2.5 ml., 0.5M) and cooled in an ice bath. Borane tert-butylamine complex (118 mg., 1.36 mmole, 1.1 eq.) was added. The ice bath was removed, and the mixture was stirred overnight at room temperature. Ether (20 ml.) and 1N HCl (20 ml.) were added and the mixture was stirred for 10 minutes. The layers were separated and the aqueous layer was reextracted with ether (2×20 ml.). The combined organic layers were dried ($MgSO_4$) and freed of solvent in vacuo leaving 571 mg. of solid. This was combined with material from a previous run and chromatographed on silica gel (Merck, 60 g. packed in hexane). [4S-[4α,5β(S*)]]-5-[2-[(Butylamino)sulfonyl]-1-hydroxyethyl]-4-(cyclohexylmethyl) -2,2-dimethyl-3-oxazolidinecarboxylic acid, 1,1-dimethylethyl ester, was eluted with ether:hexane (2:5) as a white solid (416 mg., 67.2%); m.p 116°–119°; $[\alpha]_D=+4.9°$ (c=1.0, methanol). [4S-[4α,5β(R*)]] was eluted with ether:hexane (1:1) as an oil; $[\alpha]_D=-3.33°$ (c=0.5, methanol). TLC (silica gel, ether:hexane, 2:1) $R_f=0.48$ (isomer A) and $R_f=0.33$ (isomer B).

e) [βR-(βR*,αR*,δS*)]-N-Butyl-δ-[[(1,1-dimethylethoxy)carbonyl]amino]-β,α-dihydroxycyclohexanepentanesulfonamide The [4S-[4α,5β(S*)]] isomer product from part (d) (390 mg., 0.818 mmole, 1 eq.) was dissolved in distilled tetrahydrofuran (5.1 ml., 0.16M) and treated with aqueous 10% HCl (3.4 ml., 0.24M) and glacial acetic acid (1.7 ml., 0.48M). The mixture was stirred at room temperature for 6.5 hours and then diluted with ether (30 ml.). The aqueous layer was reextracted with ether (2×25 ml.). The combined organic layers were dried ($MgSO_4$) and freed of solvent in vacuo to give [βR-(βR*,αR*,δS*)]-N-butyl-δ-[[(1,1-dimethylethoxy)carbonyl]amino]-β,α-dihydroxycyclohexanepentanesulfonamide as a foam (288 mg., 81%); $[\alpha]_D=-16.8°$ (c=0.65, chloroform). TLC (silica gel; 5% methanol in dichloromethane containing 0.2% $NH_4OH$) $R_f=0.36$.

f) [βR-(βR*,αR*,δS*)]-δ-Amino-N-butyl-β,α-dihydroxycyclohexanepentanesulfonamide, monohydrochloride The product from part (e) (285 mg., 0.65 mmole, 1 eq.) was cooled in an ice bath and treated with a cold 4N HCl solution in dioxane (4 ml., 16 mmole, 25 eq.). The mixture was stirred cold for 5 hours and dried in vacuo. The residue was chromatographed on silica gel (Merck, 15 g.), eluting with 8% methanol in dichloromethane containing 0.2% $NH_4OH$. This material was recovered and partially dissolved in 2% methanol in chloroform (10 ml.). The soluble material was filtered through a fluoropore membrane and dried in vacuo. The residue was dissolved in methanol (5 ml.), treated with a slight excess of 1N HCl solution, and freed of solvent in vacuo. The residue was dissolved in water (20 ml.), passed through a polycarbonate membrane and lyophilized to give 119 mg. of [βR-(βR*,αR*,δS*)]-δ-amino -N-butyl-β,α-dihydroxycyclohexanepentanesulfonamide, monohydrochloride as a white solid; m.p. 178°–185°; [β]$_D$=–0.87° (c=0.7, methanol). TLC (silica gel; 20% methanol in dichloromethane containing 1% NH$_4$OH) R$_f$=0.31.

Anal. calc'd. for C$_{15}$H$_{32}$N$_2$O$_4$S . 1.15 HCl: C, 47.61; H, 8.83; N, 7.40; S, 8.47; Cl, 10.77 Found: C, 47.71; H, 9.05; N, 7.34; S, 8.49; Cl, 10.69.

EXAMPLE 2

[βS-(βR*,αS*,δR*)]-δ-Amino-N-butyl,β,α-dihydroxy-cyclohexanepentanesulfonamide, monohydrochloride a) [βS-(βR*,αS,δR*)]-N-Butyl-δ-[[(1,1-dimethylethoxy)carbonyl]amino]-β,α-dihydroxycyclohexanepentanesulfonamide The [4S-[4α,5β(R*)]] isomer product from Example 1(d) (150 mg., 0.315 mmole, 1 eq.) was dissolved in distilled tetrahydrofuran (2.55 ml., 0.12M). Aqueous 10% HCl solution (1.7 ml., 0.18M) and glacial acetic acid (0.85 ml., 0.36M) were added. The mixture was stirred at room temperature for 6 hours, then diluted with ether. The layers were separated. The aqueous layer was reextracted with ether (2×15 ml.). The combined organic layers were washed with water (2×12 ml.) and saturated sodium bicarbonate solution (15 ml.), dried (MgSO$_4$), and freed of solvent in vacuo to give 93 mg. of [βS-(βR*,αS*,δR*)]-N-butyl-δ-[[(1,1-dimethylethoxy)carbonyl]amino]-β,α-dihydroxycyclohexanepentanesulfonamide as a foam; [α]$_D$=–26.4° (c=0.55, chloroform). TLC (silica gel; 10% methanol in dichloromethane containing 0.2% NH$_4$OH) R$_f$=0.53.

b) [βS-(βR*,αS*,δR*)]-δ-Amino-N-butyl-β,α-dihydroxycyclohexanepentanesulfonamide, monohydrochloride The product from part (a) (90 mg., 0.206 mmole, 1 eq.) was cooled in an ice bath and treated with cold 4N HCl in dioxane (3 ml., 12 mmole, 58 eq.). The mixture was stirred at 0° for 6 hours and dried in vacuo leaving 82 mg. of material. This was combined with 44 mg. of deprotected amine obtained by lyophilizing the aqueous layer and water washes in part (a) and the mixture was chromatographed on silica gel (Merck, 8 g.) eluting with 10% methanol in dichloromethane containing 0.2% NH$_4$OH. The resulting foam (91 mg.) was recovered, dissolved in methanol (5 ml.) and treated with 1N HCl solution (0.27 ml., 0.27 mmole, 1 eq.). The solvent was removed in vacuo. The residue was dissolved in water (20 ml.), filtered through a polycarbonate membrane, and lyophilized to give 80 mg. of [βS-(βR*,αS*, δR*)]-δ-amino-N-butyl-β,α-dihydroxycyclohexanepentanesulfonamide, monohydrochloride; m.p. 136°–142°; [α]$_D$=–12.5° (c=0.6, methanol). TLC (silica gel; 20% methanol in dichloromethane containing 1% NH$_4$OH) R$_f$=0.26.

Anal. calc'd. for C$_{15}$H$_{32}$N$_2$O$_4$S . 1.15 HCl . 0.1 H$_2$O: C, 47.38; H, 8.84; N, 7.37; S, 8.43; Cl, 10.72 Found: C, 47.43; H, 9.06; N, 7.25; S, 8.23; Cl, 10.66.

EXAMPLE 3

[1S-(1R*,2S*,3R*)]-(1-Oxo-3-phenylpropyl)-N-[4 -[(butylamino)sulfonyl]1-(cyclohexylmethyl)-2,3-dihydroxybutyl]-L-histidinamide, monohydrochloride a) N-(1-Oxo-3-phenylpropyl)-3-[(phenylmethoxy)methyl]-L-histidine A solution of N-[(1,1-dimethylethoxy)carbonyl]-3-[(phenylmethoxy)methyl]-L-histidine, methyl ester (25 g., 58.8 mmole) [prepared according to the procedure of Brown et al., J. Chem. Soc. Perkins Trans, Vol. 1, p 1553 (1982)] in acetic acid (150 ml.) containing HCl gas (1.7M) was stirred at 25° for two hours, after which it was concentrated to dryness. The gummy residue was crystallized from isopropanol to give 19 g. of 3-[(phenylmethoxy)methyl]-L-histidine, methyl ester as a white crystalline solid; m.p. 167°–168°.

A mixture of 3-[(phenylmethoxy)methyl]-L-histidine, methyl ester (18.5 g., 51 mmole), hydrocinnamic acid (7.7 g., 51 mmole), triethylamine (18 ml., 128 mmole), 1-hydroxybenzotriazole hydrate (6.9 g., 51 mmole) and 1-(3-dimethylamino -propyl)-3-ethyl carbodiimide hydrochloride (9.8 g., 51 mmole) in dimethylformamide (100 ml.) was stirred at 25° for 20 hours, after which it was diluted with pH 4 buffer (500 ml., Mallinckrodt "Buffar" solution). The mixture was then extracted with ethyl acetate and the extract was washed with water, dried (MgSO$_4$), and concentrated to give 18.7 g. of N-(1-oxo-3-phenylpropyl) -3-[(phenylmethoxy)methyl]-L-histidine, methyl ester as a clear oil.

A mixture of N-(1-oxo-3-phenylpropyl)-3 -[(phenylmethoxy)methyl]-L-histidine, methyl ester (17.2 g., 40.8 mmole) and aqueous sodium hydroxide solution (52 ml. of 1.0N solution, 52 mmole) in methanol (42 ml.) was stirred at 25° for 6 hours, after which it was diluted with water (500 ml.) and washed with ethyl acetate. The aqueous phase was neutralized by the addition of 1.0N hydrochloric acid (52 ml., 52 mmole, resulting pH of 5) and the mixture was extracted with ethyl acetate (5 times). Both the extracts and the aqueous wash were concentrated in vacuo. Each of the concentrates was stirred with hot isopropanol (500 ml. each) and filtered while hot. The filtrates were combined and partially concentrated until crystals formed. The crystals were collected and dried to give 6.5 g. of N-(1-oxo-3-phenylpropyl)-3-[(phenylmethoxy)methyl]-L-histidine as a white powder; m.p. 163°–165°.

b) [1S-(1R*,2S*,3R*)]-(1-Oxo-3-phenylpropyl)-N -[4-[(butylamino)sulfonyl]-1-(cyclohexylmethyl)-2,3-dihydroxybutyl]-3-[(phenylmethoxy)methyl]-L-histidinamide The product from part (a) (49.4 mg., 0.12 mmole, 1 eq.), [βS-(βR*,αS*,δR*)]-δ-amino-N-butyl -β,α-dihydroxycyclohexanepentanesulfonamide, monohydrochloride (46.1 mg., 0.12 mmole, 1 eq.) [product from Example 2], and 1-hydroxybenzotriazole (16.4 mg., 0.12 mmole, 1 eq.) were dissolved in distilled tetrahydrofuran (1.6 ml., 0.1M). The solution was cooled in an ice bath and 4-methylmorpholine (17 µl., 0.139 mmole, 1.15 eq.) was added. After 15 minutes, 1,3-dicyclohexylcarbodiimide (25 mg., 0.12 mmole, 1 eq.) was added. The mixture was stirred at 5° for 18 hours, then at room temperature for 6 hours and finally at 10°–15° for 16 hours. The mixture was then cooled to 0° and diluted with chloroform (5 ml.). After stirring for 45 minutes, a small amount of solid was removed by filtration. The filtrate was further diluted with chloroform, washed with aqueous sodium bicarbonate solution and aqueous saturated sodium chloride solution, dried (MgSO$_4$) and freed of solvent in vacuo. The remaining material was preabsorbed on silica gel (about 1 g.) and freed of solvent. This was applied to the top of a column packed with silica gel (Merck, 10 g.). The dicyclohexylurea was eluted with 20% acetone in chloroform. The desired product was then eluted with 5% methanol in chloroform containing 0.2% NH$_4$OH to give 73 mg. of [1S-(1R*,2S*,3R*)]-N -[4-[(butylamino)sulfonyl]-1-(cyclohexylmethyl) -2,3-dihydroxybutyl]-3-[(phenylmethoxy)methyl]-L-histidinamide. TLC (silica gel; 10% methanol in dichloromethane containing 0.2% NH₄OH) $R_f$=0.42.

c) [1S-(1R*,2S*,3R*)]-(1-Oxo-3-phenylpropyl)-N -[4, [(butylamino)sulfonyl]-1-(cyclohexylmethyl) -2,3-dihydroxybutyl]-L-histidinamide, monohydrochloride The product from part (b) (71 mg., 0.098 mmole, 1 eq.) was dissolved in methanol (2.0 ml., 0.05M), water (0.3 ml., 0.33M) and 1N HCl (100 μl., 1 eq.). 20% Palladium hydroxide on carbon (20 mg., 20% by weight) was added and the mixture was placed under a hydrogen atmosphere for 4 days. During this time, additional 20% palladium hydroxide on carbon (10 mg.) was added. The reaction was diluted with methanol, the catalyst was removed by filtration through regenerated cellulose, and the solvent was removed in vacuo leaving 62.7 mg. This was chromatographed on silica gel (Merck, 6 g.) eluting with 5–7% methanol in dichloromethane containing 0.2% NH₄OH to give 39.2 mg. of L-histidinamide product. This material was dissolved in methanol (5 ml.) and treated with 1N HCl solution (65 μl., 1 eq.). The solvent was removed in vacuo. The residue was dissolved in a water (12 ml.) and ethanol (3 ml.) mixture, passed through a polycarbonate filter, and lyophilized to give 40.4 mg. of [1S-(1R*,2S*,3R*)]-(1-oxo-3-phenylpropyl)-N-[4 -[(butylamino)sulfonyl]-1-(cyclohexylmethyl)-2, 3-dihydroxybutyl]-L-histidinamide, monohydrochloride; m.p. 62°–80°; $[\alpha]_D$=–29.5° (c=0.44, methanol). TLC (silica gel; 10% methanol in dichloromethane containing 0.2% NH₄OH) $R_f$=0.26.

Anal. calc'd. for $C_{30}H_{47}N_5O_6S \cdot HCl \cdot 1.8 H_2O$: C, 53.41; H, 7.71; N, 10.38; Cl, 5.25; S, 4.75 Found: C, 53.39; H, 7.40; N, 10.32; Cl, 5.32; S, 4.62.

EXAMPLE 4

[1S-(1R*,2R*,3S*)]-(1-Oxo-3-phenylpropyl)-N-[4 -[(butylamino)sulfonyl]-1-(cyclohexylmethyl)-2,3-dihydroxybutyl]-L-histidinamide, trifluoroacetate (1:1) salt a) [1S-(1R*,2R*,3S*)]-(1-Oxo-3-phenylpropyl)-N -[4- [(butylamino)sulfonyl]-1-(cyclohexylmethyl)-2, 3-dihydroxybutyl]-3-[(phenylmethoxy)methyl]-L-histidinamide

[βR-(βR*,αR*,δS*)]-δ-Amino-N-butyl-β,αdihydroxycyclohexanepentanesulfonamide (97 mg., 0.288 mmole, 1 eq., free base of the product of Example 1), N-(1-oxo-3-phenylpropyl)-3-[(phenylmethoxy)methyl]-L-histidine (117.4 mg., 0.288 mmole, 1 eq.), and 1-hydroxybenzotriazole 39 mg., 0.288 mmole, 1 eq.) were partially dissolved in distilled tetrahydrofuran (2.8 ml., 0.1M). The mixture was cooled in an ice bath and 1,3-dicyclohexylcarbodiimide (59.4 mg., 0.288 mmole, 1 eq.) was added. The mixture was stirred at 5°–7° for 22 hours, then at room temperature for 3 hours. Additional tetrahydrofuran (2.8 ml.) was added and the mixture was stirred overnight at room temperature. The mixture was then diluted with chloroform (12 ml.) and stirred at 0° for 1 hour. A small amount of solid was removed by filtration. The filtrate was washed with saturated aqueous sodium bicarbonate and saturated aqueous sodium chloride solution, dried (MgSO₄), and freed of solvent in vacuo. The residue was chromatographed on silica gel (Merck, 20 g.). The dicyclohexylurea was eluted with 20% acetone in chloroform and the desired product was eluted with 5% methanol in chloroform containing 0.2% NH₄OH. The material obtained was further purified by rechromatography on silica gel (Merck, 10 g.) eluting with 3% methanol in dichloromethane containing 0.2% NH₄OH to give 126 mg. of [1S-(1R*,2R*,3S*)]-(1-oxo-3-phenylpropyl)-N-[4-[(butylamino)sulfonyl]-1-(cyclohexylmethyl)-2,3-dihydroxybutyl]-3-[(phenylmethoxy)methyl]-L-histidinamide. TLC (silica gel; 10% methanol in dichloromethane containing 0.2% NH₄OH) $R_f$=0.60.

b) [1S-(1R*,2R*,3S*)]-(1-Oxo-3-phenylpropyl)-N -[4- [(butylamino)sulfonyl]-1-(cyclohexylmethyl) -2,3-dihydroxybutyl]-L-histidinamide, trifluoroacetate (1:1) salt The product from part (a) (112 mg., 0.154 mmole, 1 eq.) was dissolved in methanol (3.1 ml., 0.05M), water (0.5 ml., 0.33M), and 1N HCl (154 μl., 0.154 mmole, 1 eq.). 20% Palladium hydroxide on carbon (30 mg., 25% by weight) was added and the mixture was placed under a hydrogen atmosphere for 4 days. During this time, additional 20% palladium hydroxide on carbon (20 mg.) was added. The reaction was diluted with methanol, the catalyst was removed by filtration through regenerated cellulose and the solvent was removed in vacuo leaving 97 mg. This was chromatographed on silica gel (Merck, 10 g.) eluting with 5% methanol in dichloromethane to give 80 mg. This material was further purified by preparative HPLC using a fully capped C-18 column (YMC I - 15 100A, ODS, 30×500 mm.; 15 μ spherical, 21 ml/min., UV monitoring at 220 nm.) eluting with 76.4% methanol in water containing 1% trifluoroacetic acid. The peak which eluted at 17.5 to 20.5 minutes was taken to dryness in vacuo. The residue was dissolved in 20% ethanol in water (20 ml.), passed through a polycarbonate filter, and lyophilized to give 59 mg. of [1S-(1R*,2R*,3S*)]-(1-oxo-3-phenylpropyl)-N-[4 -[(butylamino)sulfonyl]-1-(cyclohexylmethyl)-2,3-dihydroxybutyl]-L-histidinamide, trifluoroacetate (1:1) salt; m.p. 60°–110°; $[\alpha]_D$=–30.2° (c=0.58, methanol). TLC (silica gel; 10% methanol in dichloromethane containing 0.2% NH₄OH) $R_f$=0.34.

Anal. calc'd. for $C_{30}H_{47}NO_5O_6S \cdot 0.4H_2O \cdot 1.15 CF_3COOH$: C, 52.14; H, 6.63; N, 9.41; F, 8.81; S, 4.31 Found: C, 52.11; H, 6.55; N, 9.26; F, 8.85; S, 4.57.

EXAMPLE 5

[1S-[1R*(R*),2S*,3S*]]-[2-[[(1,1-Dimethylethyl)-sulfonyl]methyl]-1-oxo-3-phenylpropyl]-N-[4-[(butylamino)sulfonyl]-1-(cyclohexylmethyl)-2,3-dihydroxybutyl]-L-histidinamide, methanesulfonate (1:1) salt a) (S)-N-[2-[(1,1-Dimethylethyl)sulfonyl]-1-oxo-3-phenylpropyl]-3-[(phenylmethoxy)methyl]-L-histidine Ethanol (57 ml., 990 mmole) and dimethylaminopyridine (20.3 g., 165 mmole) were added to a solution of benzyl acrylic acid (53.8 g., 330 mmole) in tetrahydrofuran (830 ml., 0.4M). To the resulting mixture was then added a solution of dicyclohexylcarbodiimide (68.1 g., 330 mmole) in tetrahydrofuran (330 ml.) over 2 hours. The resulting mixture was stirred at 25° for 18 hours, after which it was filtered and concentrated. The residue was partitioned between 1N hydrochloric acid and ether. The organic phase was washed with saturated aqueous sodium bicarbonate solution and brine, dried (MgSO₄), and concentrated. The semisolid residue was filtered and the filtrate was distilled in vacuo to give 45.3 g. of α-methylenebenzenepropanoic acid, ethyl ester as a colorless oil, b.p. 85°–95°/2 torr.

tert-Butyl mercaptan (62.1 ml., 547 mmole) and sodium ethoxide powder (19.6 g., 287 mmole) were added to a solution of α-methylenebenzenepropanoic acid, ethyl ester (52 g., 273 mmole) in ethanol (1300 ml.). The resulting mixture was stirred at 25° for 18 hours, after which mercaptan was removed by distillation at atmospheric pressure (b.p. 65°–80°). The residue was further concentrated in vacuo; the resulting syrup was partitioned between ether and water then extracted twice more with ether. The combined ether layer was washed with water, dried (MgSO$_4$), and concentrated to give 65.2 g. of α-[[(1,1-dimethylethyl)thio]methyl]benzenepropanoic acid, ethyl ester.

A solution of potassium monopersulfate (141 g. of Oxone mixture from Alfa) in water (650 ml.) was added to a solution of α-[[(1,1-dimethylethyl)thio]methyl]benzenepropanoic acid, ethyl ester (42.8 g., 153 mmole) in ethanol (650 ml.) at 0° over one hour, during which a white precipitate formed. When the addition was complete, the mixture was stirred at 25° for 18 hours. The mixture was partially concentrated in vacuo (to remove most of the ethanol) and was then partitioned between ether and 1N hydrochloric acid. The aqueous layer was extracted again with ether and the combined ether extract was washed with saturated aqueous sodium bicarbonate solution and brine, dried (MgSO$_4$), and concentrated to give 45.6 g. of a-[[(1,1-dimethylethyl)sulfonyl]methyl]benzenepropanoic acid, ethyl ester.

A suspension of α-[[(1,1-dimethylethyl)sulfonyl]methyl]benzenepropanoic acid, ethyl ester (21.3 g., 68.1 mmole) in 6N hydrochloric acid (165 ml.) was stirred at reflux temperature for 18 hours, after which it is concentrated in vacuo. The residue was triturated with ether to give 15.7 g. of α-[[(1,1-dimethylethyl)sulfonyl]methyl]benzenepropanoic acid as a white solid; m.p. 138°–143°.

A solution of (+)-dehydroabietylamine (59 g., 208 mmole) in acetonitrile (500 ml.) was added to a solution of α-[[(1,1-dimethylethyl)sulfonyl]methyl]benzenepropanoic acid (59 g., 208 mmole) in acetonitrile (1 l.). An immediate precipitate formed. The mixture was allowed to stand for 18 hours at 25° after which the solid was collected. The bulk of the solid was dissolved in hot isopropanol (2 l.) and the resulting solution was cooled slowly to –30°. After 24 hours, the resulting crystals were collected; m.p. 160°–170°; [α]$_D$= +18.4° (c=1.4, methanol). The crystals were recrystallized from isopropanol four more times, resulting in 30.5 g. of (S)-α-[[(1,1-dimethylethyl)-sulfonyl]methyl]benzenepropanoic acid, dehydroabietylamine (1:1) salt; m.p. 181°–183°; [α]$_D$=+22.5° (c=1.6, methanol). A solution of this dehydroabietylamine salt (30.5 g., 53.5 mmole) in ethyl acetate (500 ml.) was extracted three times with aqueous potassium carbonate solution. The combined aqueous extracts were washed once with ethyl acetate, then acidified by addition of concentrated hydrochloric acid. The solution was then extracted three times with dichloromethane. The organic extract was dried (MgSO$_4$) and concentrated. The residue was triturated with ethyl acetate/hexane mixture to give 12.2 g. of (S)-α-[[(1,1-dimethylethyl)sulfonyl]methyl] benzenepropanoic acid as a white crystalline solid; m.p. 97.5°–98.5°; [α]$_D$ =+9.1° (c=1.2, dichloromethane).

N-Methylmorpholine (5.36 g., 5 ml., 53 mmole) was added to a solution containing (S)-α-[[(1,1dimethylethyl) sulfonyl]methyl]benzenepropanoic acid (5.12 g., 18 mmole), 3-[(phenylmethoxy)methyl]-L-histidine, methyl ester, dihydrochloride (6.52 g., 18 mmole), and hydroxybenzotriazole hydrate (2.75 g., 18 mmole) in dry dimethylformamide (80 ml.) cooled to 0° under argon. The resulting mixture was treated with 1-(3-dimethylaminopropyl)-3-ethylcarbodiimide hydrochloride (3.87 g., 19.8 mmole). The reaction was allowed to warm to ambient temperature overnight. After 18 hours, the dimethylformamide was removed in vacuo, then a pH 4 phosphate buffer (90 ml.) was added and the aqueous mixture was extracted with ethyl acetate (1×100 ml., 2×150 ml.). The combined organic extracts were rinsed with water (2×100 ml.), half-saturated sodium bicarbonate (100 ml.), and brine (100 ml.). The organic solution was dried (MgSO$_4$) and evaporated to 8.37 g. of product as an oil. Reextraction of the combined water, brine and sodium bicarbonate rinses afforded an additional 0.73 g. (after chromatography) of product to give a combined yield of 9.1 g. of (S) -N-[2-[(1,1-dimethylethyl)sulfonyl]-1-oxo-3-phenylpropyl]-3-[(phenylmethoxy)methyl]-L-histidine, methyl ester; [α]$_D$=+9.84° (c=1.92, methanol). TLC (silica gel; ethyl acetate:pyridine:acetic acid: water, 180:20:6:11) R$_f$=0.55.

Anal. calc'd. for C$_{29}$H$_{37}$N$_3$O$_6$S . 0.28H$_2$O: C, 62.11; H, 6.75; N, 7.49; S, 5.72 Found: C, 62.11; H, 6.58; N, 7.47; S, 5.60.

To the above methyl ester product (8.3 g., 14.9 mmole) dissolved in dry methanol (90 ml.) cooled to 0° was added 1.0N aqueous sodium hydroxide solution (19.4 ml., 19.4 mmole). The reaction was allowed to warm to ambient temperature overnight. After 16 hours, the methanol was removed in vacuo and water (100 ml.) was added. The aqueous solution was acidified to pH 5 with 1N aqueous HCl, then extracted with ethyl acetate (4×150 ml.). The combined organic extracts were rinsed with brine (2×75 ml.), dried (MgSO$_4$), and concentrated in vacuo to yield 7.57 g. of crude product. Flash chromatography on silica gel (Merck, 1000 g.) eluted with 10:1.1:0.9 ethyl acetate:acetic acid: water provided 5.0 g. of (S)-N-[2-[(1,1-dimethylethyl)sulfonyl]-1-oxo-3-phenylpropyl]-3-[(phenylmethoxy)methyl]-L-histidine; [α]$_D$ =+40.8° (c=1.2, methanol). TLC (silica gel; ethyl acetate:acetic acid:water, 8:1.1:0.9) R$_f$=0.26.

Anal. calc'd. for C$_{28}$H$_{35}$N$_3$O$_6$S . 0.43 H$_2$O: C, 61.21; H, 6.58; N, 7.65; S, 5.84 Found: C, 61.32; H, 6.40; N, 7.54; S, 5.93.

b) [1S-[1R*(R*),2S*,3S*]]-[2-[[(1,1-Dimethylethyl)sulfonyl]methyl]-1-oxo-3-phenylpropyl]-N -[4-[(butylamino) sulfonyl]-1-(cyclohexylmethyl) -2,3-dihydroxybutyl]-3-[(phenylmethoxy]methyl]-L-histidinamide The L-histidine product from part (a) (549 mg., 1.0 mmole, 1 eq.), [βR-(βR*,αR*,δS*)]-δ-amino-N-butyl-β,α-dihydroxycyclohexanepentanesulfonamide, monohydrochloride (373 mg., 1 eq., product of Example 1), and 1-hydroxybenzotriazole (135 mg., 1.0 mmole, 1 eq.) were partially dissolved in distilled tetrahydrofuran (10 ml., 0.1M), cooled to 0° and treated with 4-methylmorpholine (110 μl., 1.0 mmole, 1.0 eq.). The mixture became cloudy. After 15 minutes at 0° C., dicyclohexylcarbodiimide (206 mg., 1.0 mmole, 1.0 eq.) was added and the mixture was stirred at 5°–7° C. for 20 hours and at room temperature 20 hours. Chloroform (40 ml.) was added and after stirring at 0° C. for 40 minutes, a small amount of solid was removed by filtration. The filtrate was washed with saturated sodium bicarbonate solution and saturated sodium chloride solution, dried (MgSO$_4$) and freed of solvent in vacuo. The remaining material (1.05 g.) was chromatographed on silica gel (60 g., Merck) eluting first with 20% acetone in chloroform to remove dicyclohexylurea. The product was then eluted with 2.5% to 4% methanol in dichloromethane to give 535 mg. of [1S-[1R*(R*),2S*,3S*]]-[2-[[(1,1 -dimethylethyl)sulfonyl] methyl]-1-oxo-3-phenylpropyl]-N-[4-[(butylamino)sulfonyl]-1-(cyclohexylmethyl) -2,3-dihydroxybutyl]-3-[(phenylmethoxy)methyl]-L-histidinamide as a foam; [α]$_D$=10.0° (c=0.9, methanol). TLC (silica gel; 5% methanol in dichloromethane) R$_f$=0.26.

c) [1S-[1R*(R*),2S*,3S*]]-[2-[[(1,1-Dimethylethyl)sulfonyl]methyl]-1-oxo-3-phenylpropyl]-N-[4-[(butylamino) sulfonyl]-1-(cyclohexylmethyl)-2,3-dihydroxybutyl]-L-histidinamide, methanesulfonate (1:1)salt The L-histidinamide product from part (b) (527 mg., 0.61 mmole, 1 eq.) was dissolved in methanol (12 ml., 0.05M) and water (1.8 ml., 0.33M). This solution was then treated with 1N HCl solution (0.61 ml., 0.61 mmole, 1 eq.) and 20% palladium hydroxide on carbon (105 mg., 20% by weight). This was stirred under a hydrogen atmosphere at room temperature for 24 hours. During this time, additional 20% palladium hydroxide on carbon (30 mg.) was added. The mixture was then diluted with methanol and the catalyst was removed in vacuo. The residue was chromatographed on silica gel (Merck, 50 g.) eluting with 5% methanol in dichloromethane containing 0.2% $NH_4OH$ to give 342 mg. of the free base. This material (342 mg., 0.462 mmole, 1 eq.) was dissolved in methanol (10 ml.) and treated with methanesulfonic acid (30 μl., 0.462 mmole, 1 eq.). The solution was stirred at room temperature for 1 hour. The solvent was removed in vacuo. The residue was dissolved in water (20 ml.), passed through a polycarbonate filter, and lyophilized to give 362 mg. of white solid [1S-[1R*(R*),2S*,3S*]][-2-[[(1,1-dimethylethyl)sulfonyl]methyl]-1-oxo-3-phenylpropyl]-N-[4-[(butylamino)sulfonyl]-1-(cyclohexylmethyl)-2,3-dihydroxybutyl]-L-histidinamide, methanesulfonate (1:1) salt; 80°–110° (dec.); $[\alpha]_D$=–5.0° (c=0.58, methanol). TLC (silica gel; 8% methanol in dichloromethane containing 0.2% $NH_4OH$) $R_f$=0.27.

Anal. calc'd. for $C_{35}H_{57}N_5O_8S_2 \cdot CH_3SO_3H \cdot 0.6 H_2O$: C, 51.06; H, 7.40; N, 8.27; S, 11.26 Found: C, 51.00; H, 7.57; N, 8.20; S, 11.60.

EXAMPLE 6

[1S-(1R*,2S*,3S*)]-N-[4-[(Butylamino)sulfonyl]-1 -(cyclohexylmethyl)-2,3-dihydroxybutyl]-3-pyridinecarboxamide Nicotinic acid (41 mg., 0.332 mmole, 1 eq.) and [βR-(βR*,αR*,δS*)]-δ-amino-N-butyl-β,α-dihydroxycyclohexanepentanesulfonamide, monohydrochloride (125 mg., 0.332 mmole, 1 eq., product from Example 1) were dissolved in dimethylformamide (1.7 ml., 0.2M). The mixture was cooled to 0° and treated with 1-hydroxybenzotriazole (44.9 mg., 0.332 mmole, 1 eq.), triethylamine (69.5 μl., 0.499 mmole, 1.5 eq.), and ethyl-3-(3-dimethylamino)propyl carbodiimide, hydrochloride (63.7 mg., 0.332 mmole, 1 eq.). The mixture was allowed to warm slowly to room temperature and stirred for 21 hours. Aqueous buffer (pH 4.0, 8 ml., Mallinckrodt) was added and the mixture stirred for 30 minutes. The precipitated solid was recovered by filtration, washed with additional buffer and water, and dried overnight in vacuo. The solid was dissolved in methanol (about 12 ml.) and preabsorbed on silica gel (about 5 g., Baker). After removal of the solvent, this was layered on top of a column of silica gel (10 g., Merck) which had been packed in dichloromethane. The product was eluted with 5% methanol in dichloromethane containing 0.2% $NH_4OH$ to give 130 mg. of crystalline solid [1S-(1R*,2S*, 3S*)]-N-[4-[(butylamino)sulfonyl]-1-(cyclohexylmethyl) -2,3-dihydroxybutyl]-3-pyridinecarboxamide; m.p. 173°–175°; $[\alpha]_D$=14.7° (c=0.9 methanol). TLC (silica gel; 10% methanol in dichloromethane containing 0.2% $NH_4OH$) $R_f$=0.45.

Anal. calc'd. for $C_{21}H_{35}N_3O_5S$: C, 57.12; H, 7.99; N, 9.52; S, 7.26 Found: C, 57.01; H, 7.99; N, 9.53; S, 7.49.

In a similar manner, nicotinic acid was reacted with the product of Example 2 to give [1S-(1R*,2S*,3R*)]-N-[4-[(butylamino)sulfonyl]-1 -(cyclohexylmethyl)-2,3-dihydroxybutyl]-3-pyridinecarboxamide; m.p. 61°–64°; $[\alpha]_D$=–19.9° (c=methanol). TLC (silica gel; chloroform:methanol:$NH_4OH$, 30:3:0.05) $R_f$=0.24.

Anal. calc'd. for $C_{21}H_{35}N_3O_5S \cdot 0.3 H_2O$: C, 56.43; H, 8.03; N, 9.40; S, 7.17 Found: C, 56.48; H, 8.04; N, 9.18; S, 6.82.

EXAMPLE 7

[1S-(1R*,2S*,3S*)]-N-[4-[(Butylamino)sulfonyl]-1 -(cyclohexylmethyl)-2,3-dihydroxybutyl]-4-pyridinecarboxamide Following the procedure of Example 6 but employing molar equivalent amounts of isonicotinic acid (41 mg., 0.332 mmole, 1 eq.) and the product of Example 1 (125 mg., 0.332 mmole, 1 eq.), 117 mg. of crystalline solid [1S-(1R*, 2S*,3S*)]-N-[4-[(butylamino)sulfonyl]-1-(cyclohexylmethyl) -2,3-dihydroxybutyl]-4-pyridinecarboxamide was obtained; m.p. 168°–186°; $[\alpha]_D$=–5.9° (c=0.66, methanol). TLC (silica gel; 5% methanol in dichloromethane containing 0.2% $NH_4OH$) $R_f$=0.22.

Anal. calc'd. for $C_{21}H_{35}N_3O_5S \cdot 0.5 H_2O$: C, 55.98; H, 8.05; N, 9.33; S, 7.12 Found: C, 56.01; H, 7.87; N, 9.41; S, 7.28.

EXAMPLE 8

[1S-(1R*,2S*,3S*)]-N-[4-[(Butylamino)sulfonyl]-1 -(cyclohexylmethyl)-2,3-dihydroxybutyl]-2-pyridinecarboxamide Following the procedure of Example 6 but employing molar equivalent amounts of picolinic acid (32.7 mg., 0.266 mmole, 1 eq.) and the product of Example 1 (100 mg., 0.266 mmole, 1 eq.), 107 mg. of solid [1S-(1R*,2S*,3S*)]-N-[4-[(butylamino)sulfonyl]-1-(cyclohexylmethyl)-2,3-dihydroxybutyl]-2-pyridinecarboxamide was obtained; m.p. 167°–170°; $[\alpha]_D$–15.5° (c=0.64, methanol). TLC (silica gel; 7% methanol in dichloromethane containing 0.2% $NH_4OH$) $R_f$=0.46.

Anal. calc'd. for $C_{21}H_{35}N_3O_5S$: C, 57.12; H, 7.99; N, 9.52; S, 7.26 Found: C, 57.08; H, 8.03; N, 9.44; S, 7.42.

EXAMPLE 9

[1S-(1R*,2S*,3S*)]-N-[4-[(Butylamino)sulfonyl]-1 -(cyclohexylmethyl)-2,3-dihydroxybutyl]-2-pyrazinecarboxamide Following the procedure of Example 6 but employing molar equivalent amounts of 2-pyrazine carboxylic acid (33.3 mg., 0.268 mmole, 1 eq.) and the product of Example 1 (100 mg., 0.268 mmole, 1 eq.), 106 mg. of solid [1S-(1R*, 2S*,3S*)]-N -[4-[(butylamino)sulfonyl]-1-(cyclohexylmethyl)-2, 3-dihydroxybutyl]-2-pyrazinecarboxamide was obtained; m.p. 178°–180°; $[\alpha]_D$=–17.4° (c=0.5, methanol) TLC (silica gel; 7% methanol in dichloromethane containing 0.2% $NH_4OH$) $R_f$=0.43.

Anal. calc'd. for $C_{20}H_{34}N_4O_5S$: C, 54.28; H, 7.74; N, 12.66; S, 7.24 Found: C, 54.44; H, 7.73; N, 12.63; S, 7.17.

EXAMPLE 10

[1S-(1R*,2S*,3S*)]-N-[4-[(Butylamino)sulfonyl]-1 -(cyclohexylmethyl)-2,3-dihydroxybutyl]-6-hydroxy -3-pyridinecarboxamide Following the procedure of Example 6 but employing molar equivalents of 6-hydroxynicotinic acid (37.3 mg., 0.268 mmole, 1 eq.) and the product of Example 1 (100 mg., 0.268 mmole, 1 eq.), 30 mg. of white solid [1S-(1R*,2S*, 3S*)]-N-[4-[(butylamino)sulfonyl]-1-(cyclohexylmethyl)-2,3-dihydroxybutyl]-6-hydroxy-3-pyridinecarboxamide was obtained; m.p. 247°–252°; [α]$_D$=–31.5° (c=0.34, methanol). TLC (silica gel; 10% methanol in dichloromethane containing 0.2% NH$_4$OH) R$_f$=0.30.

Anal. calc'd. for C$_{21}$H$_{35}$N$_3$O$_6$S: C, 55.12; H, 7.71; N, 9.18; S, 7.01 Found: C, 55.08; H, 7.76; N, 9.01; S, 6.97.

EXAMPLE 11

[1S-(1R*,2S*,3S*)]-N-[4-[(Butylamino)sulfonyl]-1 -(cyclohexylmethyl)-2,3-dihydroxybutyl]-4-pyridazinecarboxamide Following the procedure of Example 6 but employing molar equivalent amounts of 4-pyridazine carboxylic acid (33 mg., 0.268 mmole, 1 eq.) and the product of Example 1 (100 mg., 0.268 mmole, 1 eq.), 31 mg. of white solid [1S-(1R*,2S*,3S*)]-N-[4-[(butylamino)sulfonyl]-1 -(cyclohexylmethyl)-2,3-dihydroxybutyl]-4-pyridazinecarboxamide were obtained; m.p. 170°–172°; [α]$_D$= –29.1° (c=0.43, methanol). TLC (silica gel; 10% methanol in dichloromethane containing 0.2% NH$_4$OH) R$_f$=0.46.

Anal. calc'd. for C$_{20}$H$_{34}$N$_4$O$_5$S: C, 54.28; H, 7.74; N, 12.66 Found: C, 54.14; H, 7.72; N, 12.47.

EXAMPLE 12

[1S-(1R*,2S*,3S*)]-N-[4-[(Butylamino)sulfonyl]-1- (cyclohexylmethyl)-2,3 -dihydroxybutyl]benzamide Following the procedure of Example 6, but employing molar equivalent amounts of benzoic acid (32.7 mg., 0.268 mmole, 1 eq.) and the product of Example 1 (100 mg., 0.268 mmole, 1 eq.) 86.0 mg. of solid [1S-(1R*,2S*,3S*)]-N-[4-[(butylamino)sulfonyl]-1 -(cyclohexylmethyl)-2,3-dihydroxybutyl]benzamide were obtained; m.p. 153°–155°; [α]$_D$=–15.8° (c=1.49, methanol). TLC (silica gel; 7.5% methanol in dichloromethane containing 0.2% NH$_4$OH) R$_f$=0.45.

Anal. cal'd. for C$_{22}$H$_{36}$N$_2$O$_5$S . 0.37 H$_2$O: C, 59.07; H, 8.28; N, 6.26; S, 7.17 Found: C, 59.07; H, 8.32; N, 5.95; S, 7.21.

EXAMPLE 13

[1S-(1R*, 2S*, 3S*)]-N-[4-[(Butylamino)sulfonyl]-1- (cyclohexylmethyl)-2,3 -dihydroxybutyl]-3,4-dihydroxybenzamide Following the procedure of Example 6 but employing molar equivalent amounts of 3,4-dihydroxybenzoic acid (41.3 mg., 0.268 mmole, 1 eq. ) and the product of Example 1 (100 mg., 0.268 mmole, 1 eq.), 109 mg. of solid [1S-(1R*, 2S*,3S*)]-N-[4-[(butylamino)sulfonyl]-1 -(cyclohexylmethyl)-2,3-dihydroxybutyl]-3,4-dihydroxybenzamide was obtained; m.p. 162°–165° (shrinking at 152°); [α]$_D$=–21.9° (c=0.5, methanol ). TLC (silica gel; 10% methanol in dichloromethane containing 0.2% NH$_4$OH) R$_f$=0.33.

Anal. calc'd. for C$_{22}$H$_{36}$N$_2$O$_7$S . 0.25 H$_2$O: C, 55.38; H, 7.71; N, 5.87; S, 6.72 Found: C, 55.35; H, 7.94; N, 5.82; S, 6.80.

EXAMPLE 14

[1S-(1R*,2S*,3S*)]-3,4-Diamino-N- [4-[(butylamino)sulfonyl]-1 -(cyclohexylmethyl)-2,3-dihydroxybutyl]benzamide, monohydrochloride Following the procedure of Example 6 but employing molar equivalent amounts of 3,4-diaminobenzoic acid (41 mg., 0.268 mmole, 1 eq.) and the product of Example 1 (100 mg., 0.268 mmole, 1 eq.), 73 mg. of [1S-(1R*,2S*,3S*)]- 3,4-diamino-N-[4-[(butylamino)sulfonyl]-1 -(cyclohexylmethyl)-2,3-dihydroxybutyl]benzamide was obtained as a white glassy foam. This material (73 mg., 0.155 mmole, 1 eq.) was dissolved in methanol (5 ml.), treated with 1N HCl solution (0.31 ml., 0.31 mmole, 2 eq.), and then freed of solvent in vacuo. The remaining material was dissolved in water containing 5% ethanol (20 ml.), passed through a polycarbonate filter, and lyophilized to give 65 mg. of white solid [1S-(1R*,2S*,3S*)]-3,4-diamino-N-[4-[(butylamino) sulfonyl]-1 -(cyclohexylmethyl)-2,3-dihydroxybutyl]benzamide, monohydrochloride; m.p. 120°–142° (dec.); [α]$_D$=– 19.5° (c=0.4, methanol). TLC (silica gel; 10% methanol in dichloromethane containing 0.2% NH$_4$OH) R$_f$=0.43.

Anal. calc'd. for C$_{22}$H$_{38}$N$_4$O$_5$S . 0.95 HCl . 0.3 H$_2$O: C, 51.74; H, 7.81; N, 10.97; Cl, 6.60; S, 6.28 Found: C, 51.78; H, 7.87; N, 11.01; C$_{1, 6.46}$; S, 6.46.

EXAMPLE 15

[1S-[1R*(E),2S*,3S*]]-4-[[(1S,2R)-4- [(Butylamino)-sulfonyl]-1 -(cyclohexylmethyl)-2,3-dihydroxybutyl] amino]-4-oxo-2-butenoic acid, ethyl ester Fumaric acid monoethyl ester (38.6 mg., 0.268 mmole, 1 eq.) and the product of Example 1 (100 mg., 0.261 mmole, 1 eq.) were dissolved in dimethylformamide (1.4 ml., 0.2M). The mixture was cooled to 0° and treated with 1-hydroxybenzotriazole (36 mg., 0.268 mmole, 1 eq.), triethylamine (56 μl. 40.2 mmole, 1.5 eq.), and ethyl-3-(3-dimethylamino)propyl carbodiimide (51 mg., 0.268 mmole, 1 eq.). The mixture was allowed to warm slowly to room temperature and stirred for a total of 23 hours. Aqueous pH 4 buffer (8 ml., Mallinckrodt) was added and the mixture was stirred for 30 minutes. Gummy yellow material precipitated. This was extracted into ethyl acetate (2×10 ml.), washed with aqueous sodium bicarbonate solution and aqueous sodium chloride solution, dried (MgSO$_4$), and freed of solvent in vacuo. The residue (129 mg.) was chromatographed on silica gel (Merck, 12 g.) eluting with 30% acetone in hexane to give 64.2 mg. of [1S-[1R*(E),2S*,3S*]]-4-[[(1S,2R)-4-[(butylamino)-sulfonyl]-1 -(cyclohexylmethyl)-2,3-dihydroxybutyl]amino]-4-oxo-2-butenoic acid, ethyl ester as a brittle foam; [α]$_D$=–7.3° (c=0.56, chloroform). TLC (silica gel; 30% acetone in hexane) R$_f$=0.26.

Anal. calc'd. for C$_{21}$H$_{38}$N$_2$O$_7$S . 0.23H$_2$O: C, 54.04; H, 8.31; N, 6.00; S, 6.87 Found: C, 54.44; H, 8.48; N, 6.04; S, 6.47.

EXAMPLE 16

(γR, δS) -δ-Amino-N-butyl-β,γ-dihydroxy-α,α- dimethylcyclohexanepentanesulfonamide, isomer A, monohydrochloride a) N-Butyl-1-methylethanesulfonamide 2-Propanethiol (25 ml., 269 mmole, 1 eq.) was added to acetic acid (60 ml., 4.5M) and ice (approximately 30 g.) at 0°. Chlorine was then bubbled through the mixture. The reaction became bright yellow-orange, colorless, and then faintly yellow as excess chlorine was absorbed. Argon was bubbled through the reaction to remove excess chlorine and then ether (300 ml.) was added. The solution was washed with aqueous 5% sodium bisulfite (2×150 ml.) and water (200 ml.). The organic extracts were dried (MgSO$_4$) and then concentrated in vacuo to give 37.45 g. of 1-methylethanesulfonyl chloride.

N-Butylamine (16 ml., 161 mmole, 2.3 eq.) was added dropwise to a solution of 1-methylethanesulfonyl chloride (10 g., 70 mmole, 1 eq.) in dichloromethane (35 ml., 2.0M) at 0°. After the addition was complete, the ice bath was removed and the reaction was stirred overnight at room temperature. The solution was then diluted with chloroform (150 ml.) and washed with 0.5N HCl (2×125 ml.) and aqueous saturated sodium chloride (150 ml.). The organic extracts were dried ($MgSO_4$) and concentrated in vacuo. The residue was distilled to give 8.07 g. of N-butyl-1-methylethanesulfonamide as a pale yellow oil; b.p. 95°–102° at approximately 0.1 mm.

b) (4S-trans)-4-(Cyclohexylmethyl)-2,2-dimethyl-3,5-oxazolidinedicarboxylic acid, 3-(1,1-dimethylethyl) 1-methyl ester Excess diazomethane in ether was added to a solution of (4S-trans)-4-(cyclohexylmethyl)-2,2-dimethyl-3,5-oxazolidinedicarboxylic acid, 3-(1,1-dimethylethyl) ester (810 mg., 2.37 mmole, 1 eq.) [prepared as described in Example 1(b)] in dichloromethane (6 ml., 0.4M) at 0°. A few drops of acetic acid were then added to decompose the excess diazomethane. The reaction was diluted with ether and washed with aqueous saturated sodium bicarbonate and aqueous saturated sodium chloride. The organic extracts were dried ($MgSO_4$) and concentrated in vacuo. The residue was chromatographed on silica gel (Merck, 40 g.) eluting with dichloromethane to give 806 mg. of (4S-trans)-4-(cyclohexylmethyl)-2,2-dimethyl-3,5-oxazolidinedicarboxylic acid, 3-(1,1-dimethylethyl) 1-methyl ester.

c) (4S-trans)-5-[2-[(Butylamino)sulfonyl]-2-methyl-1-oxopropyl]-4-(cyclohexylmethyl)-2,2-dimethyl-3-oxazolidinecarboxylic acid, 1,1-dimethylethyl ester N-Butyllithium (2.46 ml., 6.15 mmole, 3 eq., 2.5M in hexane) was added to N-butyl-1-methyl-ethanesulfonamide (552 mg., 3.08 mmole, 1 eq.) in tetrahydrofuran (6.15 ml., 0.5M) at −40°. After 10 minutes, the reaction was warmed to −20° for 30 minutes and then cooled to −78°. (4S-trans)-4-(Cyclohexylmethyl)-2,2-dimethyl-3,5 -oxazolidinedicarboxylic acid, 3-(1,1-dimethylethyl) 1-methyl ester (729 mg., 2.05 mmole, 1 eq.) in tetrahydrofuran (4 ml., 0.5M) was then added and the reaction was stirred for a total of 3 hours at −78°. The mixture was quenched with aqueous saturated $NH_4Cl$, warmed to room temperature, and extracted with ether. The organic extracts were dried ($Na_2SO_4$), filtered through $MgSO_4$ and concentrated. The residue was chromatographed on silica gel (70 g., Merck) eluting with ether:hexane (1:4) to give 300 mg. of (4S-trans)-5-[2-[(butylamino)sulfonyl]-2-methyl-1-oxopropyl]-4 -(cyclohexylmethyl)-2,2-dimethyl-3-oxazolidinecarboxylic acid, 1,1-dimethylethyl ester; $[\alpha]_D=+11.7°$ (c=1.0, methanol).

d) (4S-trans)-5-[2-[(Butylamino)sulfonyl]-1-hydroxy-2-methylpropyl]-4 -(cyclohexylmethyl)-2,2-dimethyl-3-oxazolidinecarboxylic acid, 1,1-dimethylethyl ester, isomer A and isomer B Sodium borohydride (24.8 mg., 0.656 mmole, 1.1 eq.) in absolute ethanol (2.48 ml., 0.26M) was added to the 1,1-dimethylethyl ester product from part (c) (300 mg., 0.597 mmole, 1 eq.) in absolute ethanol (2.0 ml., 0.3M) at 0°. After 20 minutes, the reaction was concentrated and the product dissolved in ether and 1N HCl. The product was then extracted with ether. The organic extracts were dried ($Na_2SO_4$), filtered through $MgSO_4$, and concentrated. The residue was chromatographed on silica gel (Merck, 10 g.) eluting with ether:hexane (1:3) followed by (2:3) to give (4S-trans)-5-[2-[(butylamino)sulfonyl]-1-hydroxy-2 -methylpropyl]-4-(cyclohexylmethyl)-2,2-dimethyl-3-oxazolidinecarboxylic acid, 1,1-dimethylethyl ester, isomer B (61 mg.) and isomer A (172 mg.); $[\alpha]_D=-19.0°$ (c=1.0, methanol).

e) (γR,δS)-δ-Amino-N-butyl-β,γ-dihydroxy-α,α-dimethylcyclohexanepentanesulfonamide, isomer A, monohydrochloride 10% HCl (1.21 ml., 0.25M) and acetic acid (0.61 ml., 0.5M) were added to a solution of the isomer A product from part (d) (153 mg., 0.303 mmole, 1 eq.) in tetrahydrofuran (1.82 ml., 0.17M) and stirred at room temperature for a total of 3 days. The solution was then diluted with water (5 ml.) and ether (10 ml.). After separation of the layers, the organic phase was extracted twice with water. The aqueous washes were then combined and lyophilized. The product was chromatographed on silica gel (Merck, 10 g.) eluting with chloroform:methanol:$NH_4OH$ (30:2.5:0.05) to give 68.4 mg. of isomer A product as the free base. This material (68.4 mg., 0.188 mmole, 1 eq.) was dissolved in methanol (10 ml.) and treated with 1N HCl (0.188 ml., 0.188 mmole, 1 eq.). After 30 minutes at room temperature, the solution was concentrated. The residue was dissolved in water (10 ml.), filtered through a polycarbonate filter, and lyophilized to give 67 mg. of solid, white (γR,δS)-δ-amino-N-butyl-β,γ-dihydroxy-α,α-dimethylcyclohexanepentanesulfonamide, isomer A, monohydrochloride; m.p. 74°–81°; $[\alpha]_D=-12.7°$ (c=1.0, methanol). TLC (silica gel; chloroform:methanol: $NH_4OH$, 30:2.5:0.05) $R_f=0.21$.

Anal. calc'd. for $C_{17}H_{36}N_2O_4S \cdot HCl \cdot 0.3 H_2O$: C, 50.24; H, 9.33; N, 6.89; $C_{1, 8.72}$; S, 7.89 Found: C, 50.22; H, 9.23; N, 6.78; Cl, 8.68; S, 7.83.

EXAMPLE 17

(γR,δS)-δ-Amino-N-butyl-β,γ-dihydroxy-α,α-dimethyl cyclohexanepentanesulfonamide, isomer B, monohydrochloride Aqueous 10% HCl (0.45 ml., 0.25M) and acetic acid (0.23 ml., 0.5M) were added to a solution of the isomer B product from Example 16(d) (59.3 mg., 0.118 mmole, 1 eq.) in tetrahydrofuran (0.7 ml., 0.17M) and stirred at room temperature for 3 days. The solution was then diluted with water (5 ml.) and ether (10 ml.). After separation of the layers, the organic phase was extracted twice with water. The aqueous washes were then combined and lyophilized. The product was chromatographed on silica gel (Merck, 5 g.) eluting with chloroform:methanol: $NH_4OH$ (30:2.5:0.05) to give 17.4 mg. of isomer B product as the free base. This material (17.4 mg., 0.048 mmole, 1 eq.) was dissolved in methanol (8 ml.) and treated with 1N HCl (0.05 ml., 0.05 mmole, 1 eq.). After 30 minutes at room temperature, the solution was concentrated. The residue was dissolved in water (10 ml.), filtered through a polycarbonate filter, and lyophilized to give 10.5 mg. of white (γR,δS)-δ-amino-N-butyl-β,γ-dihydroxy-α,α-dimethylcyclohexanepentanesulfonamide, isomer B, monohydrochloride; m.p. 79°–85°. TLC (silica gel; chloroform:methanol:$NH_4OH$, 30:3:0.05) $R_f=0.19$.

Anal. calc'd. for $C_{17}H_{36}N_2O_4S \cdot HCl \cdot 0.7 H_2O$: C, 49.37; H, 9.36; N, 6.77 Found: C, 49.27; H, 9.25; N, 6.95.

EXAMPLE 18

(γR,δS)-δ-Amino-N,β-dibutyl-β,γ-dihydroxycyclohexanepentanesulfonamide, isomer A a) (4S-trans)-4-(Cyclohexylmethyl)-2,2-dimethyl-5-(1-oxopentyl)-3-oxazolidinecarboxylic acid, 1,1-dimethylethyl ester (4S-trans)-4-(Cyclohexylmethyl)-5-[[(methoxy)methylamino]carbonyl]-2,2-dimethyl-3 -oxazolidenecarboxylic acid, 1,1-dimethylethyl ester [1.5 g., 3.9 mmole, 1 eq., prepared as described in Example 1(b)] was dissolved in distilled tetrahydrofuran (15.6 ml., 0.25M) under an argon atmosphere. The solution was cooled to −78° and n-butyl lithium (1.72 ml., 4.29 mmole, 1.1 eq., 2.5M in hexane) was added dropwise. The reaction was stirred for 30 minutes at −78° and then warmed to 0° and stirred for an additional 30 minutes. The mixture was quenched with aqueous saturated $NH_4Cl$ and extracted three times with ether. The ether extracts were dried ($MgSO_4$) and freed of solvent in vacuo. The residue was chromatographed on silica gel (100 g., Merck) eluting with ether:hexane (1:2) to give (4S-trans)-4-(cyclohexyl-methyl)-2,2-dimethyl-5-(1 -oxopentyl)-3-oxazolidinecarboxylic acid, 1,1-dimethylethyl ester.

b) (4S-trans)-5-[2-[(Butylamino)sulfonyl]-1-butyl-1-hydroxyethyl]-4 -(cyclohexylmethyl)-2,2-dimethyl-3-oxazolidinecarboxylic acid, 1,1-dimethylethyl ester, isomer A and isomer B n-Butyllithium (4.48 ml., 11.2 mmole, 2.8 eq., 2.5M in hexane) was added to a solution of N-butylmethanesulfonamide [846 mg., 5.6 mmole, 1.4 eq., prepared as described in Example 1(a)] in tetrahydrofuran (16 ml., 0.35M) at −40° and stirred for 10 minutes. The reaction was then warmed to 0°, stirred for 30 minutes and cooled to −40°. (4S-trans)-4-(Cyclohexylmethyl)-2,2-dimethyl-5-(1-oxopentyl)-3 -oxazolidinecarboxylic acid, 1,1-dimethylethyl ester (1.5 g., 3.93 mmole, 1 eq.) in tetrahydrofuran (4 ml., 1.0M) was then added. After 90 minutes at −40°, the reaction was quenched with aqueous saturated $NH_4Cl$, warmed to room temperature and extracted three times with ether. The organic extracts were dried ($Na_2SO_4$), filtered through $MgSO_4$, and concentrated. The residue was chromatographed on silica gel (Merck, 80 g.) eluting with hexane:acetone (10:1) to provide 237 mg. of (4S-trans)-5-[2-[butylamino)sulfonyl]-1-butyl-1-hydroxyethyl]-4 -(cyclohexylmethyl)-2,2-dimethyl-3-oxazolidinecarboxylic acid, 1,1-dimethylethyl ester, isomer A; $[\alpha]_D=+4.2°$ (c=1.0, methanol) and 101 mg. of isomer B; m.p. 138°–140°; $[\alpha]_D=+5.5°$ (c=1.0, methanol) and 1.518 g. of a mixture of isomer A and isomer B.

c) (γR,δS)-δ-Amino-N,β-dibutyl-β,γ-dihydroxycyclohexanepentanesulfonamide, isomer A Aqueous 10% HCl (1.78 ml., 0.25M) and acetic acid (0.89 ml., 0.5M) were added to a solution of the isomer A product from part (b) (237 mg., 0.446 mmole, 1 eq.) in tetrahydrofuran (2.67 ml., 0.17M) and stirred at room temperature for a total of 4 days. The reaction was then concentrated. The residue was chromatographed on silica gel (Merck, 10 g.) eluting with chloroform:methanol:$NH_4OH$ (30:2.5:0.05) to give 127 mg. of white, solid (γR,δS)-δ-amino-N,β-dibutyl-β,γ-dihydroxycyclohexanepentanesulfonamide, isomer A; m.p. 164°–165°; $[\alpha]_D=-9.3°$ (c=0.50, methanol). TLC (silica gel; chloroform:methanol:$NH_4OH$, 30:3:0.05) $R_f=0.22$.

Anal. calc'd. for $C_{19}H_{40}N_2O_4S$: , C, 58.13; H, 10.27, N, 7.14; S, 8.17 Found: C, 57.81; H, 10.37; N, 7.13; S, 7.87.

EXAMPLE 19

(γR,δS)-δ-Amino-N,β-dibutyl-β,γ-dihydroxycyclohexanepentanesulfonamide, isomer B, monohydrochloride Aqueous 10% HCl (0.76 ml., 0.25M) and acetic acid (0.38 ml., 0.5M) were added to a solution of the isomer B product from Example 18(b) (100.7 mg., 0.189 mmole, 1 eq.) in tetrahydrofuran (1.13 ml., 0.17M) and stirred at room temperature for a total of 5 days. The reaction was then concentrated in vacuo. The residue was chromatographed on silica gel (Merck, 5 g.) eluting with chloroform:methanol:$NH_4OH$ (30:2.5:0.05) to give 55 mg. of product. This material (52.4 mg., 0.134 mmole, 1 eq.) was dissolved in methanol (5 mi.) and treated with aqueous 1N HCl (0.13 ml., 0.13 mmole, 1 eq.). After 30 minutes at room temperature, the solution was concentrated in vacuo. The product was dissolved in water:ethanol (10:1, 11 ml.), passed through a polycarbonate filter, and lyophilized to give 55.7 mg. of (γR,δS)-δ-amino-N,β-dibutyl-β,γ-dihydroxycyclohexanepentanesulfonamide, isomer B, monohydrochloride; m.p. 80°–85°; $[\alpha]_D=+20.8°$ (c=0.50, methanol).

Anal. calc'd. for $C_{19}H_{40}N_2O_4S$ . HCl: C, 53.19; H, 9.63; N, 6.53; Cl, 8.26; S, 7.47 Found: C, 53.25; H, 9.58; N, 6.16; Cl, 1, 8.65; S, 7.21.

EXAMPLE 20

[1S-(1R*,2S*,3S*)]-(2-Indolylcarbonyl)-N-[4-[(butylamino)sulfonyl]-1-(cyclohexylmethyl)-2,3-dihydroxybutyl]-L-histidinamide, trifluoroacetate (1:1)salt a) N-(1H-Indol-2-ylcarbonyl)-3-[(phenylmethoxy)methyl]-L-histidine, methyl ester 3-[(Phenylmethoxy)methyl]-L-histidine, methyl ester (2.36 g., 6.5 mmole, 1 eq.) was suspended in distilled tetrahydrofuran (65 ml., 0.1M) and cooled in an ice bath. To this was added 4-methylmorpholine (1.43 ml., 13 mmole, 2 eq.), indole-2-carboxylic acid (1.048 g., 6.5 mmole, 1 eq.) and 1,3-dicyclohexylcarbodiimide (1.339 g., 6.5 mmole, 1 eq.). The mixture was allowed to warm slowly to room temperature and stirred overnight. The mixture was diluted with chloroform (200 ml.) and stirred in an ice bath for 45 minutes. The solid was removed by filtration and washed with additional chloroform. The filtrate was washed with saturated aqueous sodium bicarbonate solution and saturated aqueous sodium chloride solution, dried ($MgSO_4$), and freed of solvent in vacuo. The remaining material was chromatographed on silica gel (Merck, 160 g.) eluting first with 20% acetone in chloroform to remove dicyclohexylurea. The product was then eluted with 4% methanol in chloroform containing 0.2% $NH_4OH$ to give 2.9 g. of N-(1H-indol-2-ylcarbonyl)-3-[(phenylmethoxy)methyl]-L-histidine, methyl ester. TLC (silica gel; 10% methanol in chloroform containing 0.2% $NH_4OH$) $R_f=0.43$.

b) N-(1H-Indol-2-ylcarbonyl)-3-[(phenylmethoxy)-methyl]-L-histidine

The methyl ester product from part (a) (2.79 g., 6.49 mmole, 1 eq.) was dissolved in methanol (25 ml., 0.25M) and treated with 1N sodium hydroxide solution (7.8 ml., 7.8 mmole, 1.2 eq.). The mixture was stirred at room temperature for 3 hours. The methanol was removed in vacuo. Water (approximately 20 ml.) was added. A chloroform wash (30 ml.) removed any nonacidic material. The aqueous layer was then adjusted to pH 3–4 using 1N HCl solution. Gummy material precipitated. This was triturated with 5% methanol in ethyl acetate to give 2.142 g. of white, solid N-(1H-indol-2-ylcarbonyl)-3-[(phenylmethoxy)methyl]-L-histidine; m.p. 204°–207° (dec.); $[\alpha]_D = -0.17°$ (c=0.59, acetic acid). TLC (silica gel; ethyl acetate:pyridine:acetic acid:water, 5:1:1:1) $R_f = 0.36$.

c) [1S-(1R*,2S*,3S*)]-(2-Indolylcarbonyl)-N-[4-[(butylamino)sulfonyl]-1-(cyclohexylmethyl)-2,3-dihydroxybutyl]-3-[(phenylmethoxy)methyl]-L-histidinamide N-(1H-Indol-2-ylcarbonyl)-3-[(phenylmethoxy)methyl]-L-histidine (628 mg., 1.5 mmole, 1 eq..) and [βR-(βR*,γR*,δS*)]-δ-amino-N-butyl-β,γ-dihydroxycyclohexanepentanesulfonamide, monohydrochloride (564 mg., 1.5 mmole, 1 eq.) [product of Example 1] were partially dissolved in dimethylformamide (7.5 ml., 0.2M). The mixture was cooled to 0° and treated with 1-hydroxybenzotriazole (202.5 mg., 1.5 mmole, 1 eq.), triethylamine (315 μl., 2.25 mmole, 1.5 eq.) and ethyl-3-(3-dimethylamino)-propyl carbodiimide, hydrochloride (295 mg., 1.5 mmole, 1 eq.). The mixture was allowed to warm slowly to room temperature and stirred for a total of 22 hours. Aqueous buffer (pH 4, 38 ml., Mallinckrodt) was added and the mixture was stirred for 30 minutes. The precipitated yellow taffy was extracted into ethyl acetate (2×75 ml.). The combined extracts were washed with saturated aqueous sodium bicarbonate solution (75 ml.) and saturated aqueous sodium chloride solution (75 ml.), dried (MgSO₄) and freed of solvent in vacuo leaving a yellow foam. This was chromatographed on silica gel (Merck, 70 g.) eluting with 3% methanol in dichloromethane containing 0.2% NH₄OH to give 979 mg. of [1S(1R*,2S*,3S*)]-(2-indolylcarbonyl)-N-[4-[(butylamino)sulfonyl]-1-(cyclohexylmethyl)-2,3-dihydroxybutyl]-3-[(phenylmethoxy)methyl]-L-histidinamide. TLC (silica gel; 10% methanol in dichloromethane containing 0.2% NH₄OH) $R_f = 0.42$.

d) [1S-(1R*,2S*,3S*)]-(2-Indolylcarbonyl)-N-[4-[(butylamino)sulfonyl]-1-(cyclohexylmethyl)-2,3-dihydroxybutyl]-L-histidinamide, trifluoroacetate (1:1)salt The product from part (c) (970 mg., 1.13 mmole, 1 eq.) was suspended in methanol (26 ml., 0.05M) and treated with hydrazine (640 μl, 20.2 mmole, approximately 15 eq.) and 20% palladium hydroxide on carbon (300 mg., approximately 30% by weight) and stirred at room temperature under a hydrogen atmosphere for a total of 5 days. During this period, additional methanol (10 ml.), hydrazine (450 μl), and catalyst (230 mg.) were added three times. The catalyst was removed by filtration through regenerated cellulose and the solvent was removed in vacuo. The remaining material was purified by preparative HPLC using a fully capped C-18 column (YMC 1 - 15 100A, ODS 30×500 mm, 15μ spherical, 25 mi./min., UV monitoring at 220 nm) eluting with 72.4% methanol in water containing 1% trifluoroacetic acid. Two peaks were obtained in each of the 11 injections. The slower moving peaks (20 min., 20 sec. to 24 min., 40 sec.) were combined, taken to near dryness in vacuo and dissolved in an ethanol:water mixture (2:3) and lyophilized. The material was again dissolved in ethanol:water (3:5), passed through a polycarbonate filter, and relyophilized to give 491 mg. of solid [1S-(1R*,2S*,3S*)]-(2-indolylcarbonyl)-N-[4-[(butylamino)sulfonyl]-1-(cyclohexylmethyl)-2,3-dihydroxybutyl]-L-histidinamide, trifluoroacetate (1:1)salt; m.p. 108°–127° (dec.); $[\alpha]_D = -29.6°$ (c=0.5, methanol). TLC (silica gel; 10% methanol in dichloromethane containing 0.2% NH₄OH) $R_f = 0.38$.

Anal. calc'd. for $C_{30}H_{44}N_6O_6S \cdot 1.1\ CF_3COOH \cdot 0.4\ H_2O$: C, 51.61; H, 6.17; N, 11.21; S, 4.28; F, 8.37 Found: C, 51.60; H, 6.16; N, 11.15; S, 4.05; F, 8.59.

EXAMPLE 21

(γR,δS)-δ-Amino-N-butyl-β,γ-dihydroxy-α-methylcyclohexanepentanesulfonamide, isomer B, monohydrochloride a) N-Butylethanesulfonamide n-Butylamine (30.9 ml., 312 mmole, 2 eq.) was added dropwise to a solution of ethanesulfonyl chloride (14.7 ml., 156 mmole, 1 eq.) in dichloromethane (78 ml., 2.0M) at 0°. The ice bath was allowed to melt and the reaction was stirred at room temperature overnight. The mixture was then diluted with chloroform (300 ml.) and washed with 0.5N HCl (2×300 ml.) and aqueous saturated sodium chloride (250 ml.). The organic extracts were dried (MgSO₄), filtered, and freed of solvent in vacuo. The residue was distilled to give 22.5 g. of N-butylethanesulfonamide as an oil; b.p. 112°–114° (0.5 mm.).

b) (4S-trans)-5-[2-[(Butylamino)sulfonyl]-1-oxopropyl]-4-(cyclohexylmethyl)-2,2-dimethyl-3-oxazolidinecarboxylic acid, 1,1-dimethylethyl ester n-Butyllithium (5.9 ml., 14.8 mmole, 5 eq., 2.5M in hexane) was added to a solution of N-butylethanesulfonamide (1.22 g., 7.4 mmole, 2.5 eq.) in tetrahydrofuran (14.8 ml., 0.5M) at −40°. (4S-trans)-4-(Cyclohexylmethyl)-5-[[(methoxy)methylamino]carbonyl]-2,2-dimethyl-3-oxazolidinecarboxylic acid, 1,1-dimethylethyl ester [1.0 g., 2.6 mmole, 1 eq., prepared as set forth in Example 1(b)] in tetrahydrofuran (2.6 ml., 1.0M) was then added. After 1 hour at −40°, the reaction was quenched with aqueous saturated NH₄Cl, warmed to room temperature, and made acidic (pH=3) by addition of aqueous 10% HCl. The mixture was extracted three times with ether. The organic extracts were dried over Na₂SO₄, filtered through MgSO₄ and concentrated. The residue was chromatographed on silica gel (Merck, 100 g.) eluting with ether:hexane (1:2) to give 823 mg. of (4S-trans)-5-[2-[(butylamino)-sulfonyl]-1-oxopropyl]-4 -(cyclohexylmethyl)-2,2-dimethyl-3-oxazolidinecarboxylic acid, 1,1-dimethylethyl ester as a mixture of diastereomers; $[\alpha]_D = +65.2°$ (c=2.0, methanol).

c) (4S-trans)-5-[2-[(Butylamino)sulfonyl]-1-hydroxypropyl]-4-(cyclohexylmethyl)-2,2-dimethyl-3-oxazolidinecarboxylic acid, 1,1-dimethylethyl ester Borane-tert-butylamine complex (89.7 mg., 1.03 mmole, 1.1 eq., Aldrich) was added to the product from part (b) (458.1 mg., 0.937 mmole, 1 eq. ) in ether (1.87 ml., 0.5M)

at 0°. The ice bath was allowed to melt and the reaction was stirred at room temperature overnight. The solution was quenched by the addition of aqueous 1N HCl and extracted three times with ether. The organic extracts were dried ($Na_2SO_4$), filtered through $MgSO_4$, and concentrated. The product was chromatographed on silica gel (Merck, 25 g.) eluting with ether: hexane (1:2) followed by (1:1) to give 41 mg. of (4S-trans)-5-[2-[(butylamino)sulfonyl]-1-hydroxypropyl]-4-(cyclohexylmethyl)-2,2 -dimethyl-3-oxazolidinecarboxylic acid, 1,1-dimethylethyl ester as a mixture of isomers A and B; 78 mg. of isomer B, $[\alpha]_D=-7.78°$ (c=0.75, methanol); 202 mg. of isomer C, $[\alpha]_D=+14.6°$ (c=0.50, methanol); and 118 mg. of isomer D, $[\alpha]_D=-1.27°$ (c=1.0, methanol).

d) (γR,δS)-δ-Amino-N-butyl-β,γ-dihydroxy-α-methylcyclohexanepentanesulfonamide, isomer B, monohydrochloride Aqueous 10% HCl (0.64 ml., 0.25M) and acetic acid (0.32 ml., 0.5M) were added to a solution of the isomer B product from part (c) (78 mg., 0.159 mmole, 1 eq.) in tetrahydrofuran (0.96 ml., 0.17M) and stirred at room temperature for a total of 4 days. The reaction was then concentrated. The residue was chromatographed on silica gel (Merck, 5 g.) eluting with chloroform:methanol:$NH_4OH$ (30:3.5:0.05) to give 48.5 mg. of the desired product as the free base. This material (47.6 mg., 0.136 mmole, 1 eq.) was dissolved in methanol (10 ml.) and treated with 1N HCl (0.136 ml., 0.136 mmole, 1 eq.). After 30 minutes at room temperature, the solution was concentrated. The residue was dissolved in water (10 ml.), filtered through a polycarbonate filter, and lyophilized to give 52 mg. of white (γR,δS)-δ-amino-N-butyl-β,γ-dihydroxy-α-methylcyclohexanepentanesulfonamide, isomer B, monohydrochloride; m.p. 89°–92°; $[\alpha]_D=-2.8°$ (c=0.50, methanol). TLC (silica gel; chloroform:methanol:$NH_4OH$, 30:3.5:0.05) $R_f=0.25$.

Anal. calc'd. for $C_{16}H_{34}N_2O_4S$ . 1.15 HCl: C, 48.97; H, 9.03; N, 7.14; Cl, 10.39; S, 8.17 Found: C, 49.22; H, 9.17; N, 6.95; Cl, 10.22; S, 7.84.

EXAMPLE 22

(γR,δS)-δ-Amino-N-butyl-β,γ-dihydroxy-α-methylcyclohexanepentanesulfonamide, isomer C, monohydrochloride Aqueous 10% HCl (1.65 ml., 0.25M) and acetic acid (0.82 ml., 0.5M) were added to a solution of the isomer C product from Example 21 (c) (202 mg., 0.412 mmole, 1 eq.) in tetrahydrofuran (2.47 ml., 0.17M) and stirred at room temperature for 4 days. The reaction was then concentrated. The residue was chromatographed on silica gel (Merck, 5 g.) eluting with chloroform:methanol $NH_4OH$ (30:3.5:0.05) to give 119 mg. of the desired product as the free base. This material (119 mg., 0.341 mmole, 1 eq.) was dissolved in methanol (10 ml.) and treated with 1N HCl (0.34 ml., 0.34 mmole, 1 eq.). After 30 minutes at room temperature, the solution was concentrated. The residue was dissolved in water (10 ml.), filtered through a polycarbonate filter, and lyophilized to give 105 mg. of white (γR,δS)-δ-amino-N-butyl-β,γ-dihydroxy-α-methylcyclohexanepentanesulfonamide, isomer C, monohydrochloride; m.p. 215°–217°; $[\alpha]_D=+0.4°$ (c=0.50, methanol). TLC (silica gel; chloroform:methanol:$NH_4OH$, 30:3.5:0.05) $R_f=0.19$.

Anal. calc'd. for $C_{16}H_{34}N_2O_4S$ . 1.1 HCl: C, 49.04; H, 9.06; N, 7.15; Cl, 9.95; S, 8.18 Found: C, 49.44; H, 9.29; N, 7.00; Cl, 9.77; S, 7.78.

EXAMPLE 23

(γR,δS)-δ-Amino-N-butyl-β,γ-dihydroxy-α-methylcyclohexanepentanesulfonamide, isomer D, monohydrochloride Aqueous 10% HCl (1.15 ml., 0.25M) and acetic acid (0.58 ml., 0.5M) were added to a solution of the isomer D product from Example 21 (c) (141.4 mg., 0.288 mmole, 1 eq.) in tetrahydrofuran (1.73 ml., 0.17M) and stirred at room temperature for 4 days. The reaction was then concentrated. The residue was chromatographed on silica gel (Merck, 5 g) eluting with chloroform:methanol:$NH_4OH$ (30:3.5:0.05) to give 64.2 mg. of the desired product as the free base. This material (61.5 mg., 0.175 mmole, 1 eq.) was dissolved in methanol (10 ml.) and treated with 1N HCl (0.175 ml., 0.175 mmole, 1 eq.). After 30 minutes at room temperature, the solution was concentrated. The residue was dissolved in water (10 ml.), filtered through a polycarbonate filter, and lyophilized to give 65.6 mg. of white (γR,δS)-δ-amino-N-butyl-β,γ-dihydroxy-α-methylcyclohexanepentanesulfonamide, isomer D, monohydrochloride; m.p. 62°–70°; $[\alpha]_D=-19.8°$ (c=0.50, methanol). TLC (silica gel; chloroform:methanol:$NH_4OH$, 30:3.5:0.05) $R_f=0.19$. Anal. calc'd. for $C_{16}H_{34}N_2O_4S$ . 1.05 HCl: C, 49.20; H, 9.10; N, 7.17; Cl, 9.53; S, 8.21 Found: C, 49.21; H, 9.16; N, 7.00; Cl, 9.56; S, 7.92.

EXAMPLE 24

(γR,δS)-δ-Amino-N-butyl-β,γ-dihydroxy-α-methylcyclohexanepentanesulfonamide, mixture of isomers A and B (1:1), monohydrochloride Aqueous 10% HCl (0.30 ml., 0.25M) and acetic acid (0.15 ml., 0.5M) were added to a solution of the product obtained as a mixture of isomers A and B in Example 21 (c) (36.8 mg., 0.075 mmole, 1 eq.) in tetrahydrofuran (0.45 ml., 0.17M) and stirred at room temperature for a total of 3 days. The reaction was then concentrated. The residue was chromatographed on silica gel (Merck, 5 g.) eluting with chloroform: methanol:$NH_4OH$ (30:3.5:0.05) to give 19.7 mg. of the desired product as the free base. This material (19.7 mg., 0.056 mmole, 1 eq.) was dissolved in methanol (10 ml.) and treated with 1N HCl (0.056 ml., 0.056 mmole, 1 eq.). After 30 minutes at room temperature, the solution was concentrated. The residue was dissolved in water (10 ml.), and ethanol (1 ml.), filtered through a polycarbonate filter, and lyophilized to give 24.8 mg. of white (γR,δS)-δ-amino-N-butyl-β,γ-dihydroxy-α-methylcyclohexanepentanesulfonamide, mixture of isomers A and B (1:1), monohydrochloride; m.p. 93°–95°. TLC (silica gel; chloroform:methanol:$NH_4OH$, 30:3.5:0.05) $R_f=0.25$.

Anal. calc'd. for $C_{16}H_{34}N_2O_4S$ . 1.1 HCl: C, 48.53; H, 9.09; N, 7.07; Found: C, 48.63; H, 8.74; N, 7.02.

EXAMPLE 25

[1S-(1R*,2S*,3S*)]-[(1,1-Dimethylethoxy) carbonyl]-N-[4-[(butylamino)sulfonyl]-1 -(cyclohexylmethyl)-2,3-dihydroxybutyl]-L-histidinamide, monohydrochloride a)
N-[(1,1-Dimethylethoxy)carbonyl]-3-[(phenylmethoxy) methyl]-L-histidine

N-[(1,1-Dimethylethoxy)carbonyl]-3-[(phenylmethoxy)methyl]-L-histidine, methyl ester (18.66 g., 43.8 mmole) was dissolved in methanol (50 ml.). Aqueous sodium hydroxide (1N, 92 ml.) was added followed by water (83 ml.). After keeping the reaction at room temperature for 90 minutes, it was further diluted by the addition of water (650 ml.) and acidified to pH 4.5 using aqueous hydrochloric acid. The aqueous solution was extracted with chloroform. The chloroform solution was evaporated and the residue was crystallized from ethyl acetate to give 15.3 g. of N-[(1,1-dimethylethoxy)carbonyl]-3-[(phenylmethoxy)methyl]-L-histidine; m.p. 155°–157°.

b) [1S-(1R*,2S*,3S*)]-[(1,1-Dimethylethoxy)carbonyl]-N-[4-[(butylamino)sulfonyl]-1-(cyclohexylmethyl)-2,3-dihydroxybutyl]-3-[(phenylmethoxy)methyl]-L-histidinamide N-[(1,1-Dimethylethoxy)carbonyl]-3-[(phenylmethoxy)methyl]-L-histidine (101 mg., 0.268 mmole, 1 eq.) and [γR-(γR*,γR*,δS*)-δ-amino-N-butyl-β,γ-dihydroxycyclohexanepentanesulfonamide, monohydrochloride (100 mg., 0.268 mmole, 1 eq., product of Example 1) were dissolved in dimethylformamide under an argon atmosphere. The solution was cooled to 0° and treated with 1-hydroxybenzotriazole (36 mg., 0.268 mmole, 1 eq.), triethylamine (56 μl, 0.402 mmole, 1.5 eq.) and ethyl-3-(3-dimethylamino)-propyl carbodiimide (51 mg., 0.268 mmole, 1 eq.). The mixture was allowed to warm slowly to room temperature and stirred overnight. Aqueous buffer (pH 4, 7 ml., Mallinckrodt) was added and the mixture was stirred for 30 minutes. The product was extracted into ethyl acetate (2×10 ml.), dried (MgSO$_4$), and freed of solvent in vacuo. The remaining material was chromatographed on silica gel (Merck, 15 g.) eluting with 3% methanol in dichloromethane containing 0.2% NH$_4$OH to give 176 mg. of [1S-(1R*,2S*,3S*)]-[(1,1-dimethylethoxy)carbonyl]-N-[4-[(butylamino)sulfonyl]-1-(cylcohexylmethyl)-2,3-dihydroxybutyl]-3-[(phenylmethoxy)methyl]-L-histidinamide. TLC (silica gel; 10% methanol in dichloromethane containing 0.2% NH$_4$OH) R$_f$=0.59.

c) [1S-(1R*,2S*,3S*)]-[(1,1-Dimethylethoxy)carbonyl]-N-[4-[(butylamino)sulfonyl]-1-(cyclohexylmethyl)-2,3-dihydroxybutyl]-L-histidinamide, monohydrochloride The product from part (b) (176 mg., 0.253 mmole, 1 eq.) was dissolved in methanol (5 ml., 0.05M) and water (0.8 ml., 0.33M). This solution was then treated with 1N HCl solution (0.25 ml., 0.25 mmole, 1 eq.) and 20% palladium hydroxide on carbon (44 mg., 25% by weight). This was stirred at room temperature under hydrogen for 20 hours. The mixture was then diluted with methanol and the catalyst was removed by filtration through regenerated cellulose. The solvent was removed in vacuo and the residue was chromatographed on silica gel (15 g., Merck) eluting with 3–5% methanol in dichloromethane containing 0.2% NH$_4$OH to give 69 mg. of the desired free base as a glass. This material (69 mg., 0.12 mmole, 1 eq.) was dissolved in methanol (5 ml.) and treated with 1N HCl solution (0.12 ml., 0.12 mmole, 1 eq.) The solvent was removed in vacuo. The residue was dissolved in water containing 15% ethanol (20 ml.), passed through a polycarbonate filter, and lyophilized to give 43 mg. of a white, solid [1S-(1R*,2S*,3S*)]-[(1,1-dimethylethoxy)carbonyl]-N-[4-[(butylamino)sulfonyl]-1 -(cyclohexylmethyl)-2,3-dihydroxybutyl]-L-histidinamide, monohydrochloride; m.p. 115°–140° (shrinking at 90°); [α]$_D$=−27° (c=0.37, methanol). TLC (silica gel; 10% methanol in chloroform containing 0.2% NH$_4$OH) R$_f$=0.44.

Anal. calc'd. for: C$_{26}$H$_{47}$N$_5$O$_7$S . HCl . H$_2$O: C, 49.71; H, 8.02; N, 11.15; Cl, 5.64; S, 5.10 Found: C, 49.76; H, 7.92; N, 11.23; Cl, 5.91; S, 5.30.

EXAMPLE 26

[βR-(βR*,γR*,δS*)]-N-Butyl-β,γ-dihydroxy-δ-[(methylsulfonyl)amino]cyclohexanepentanesulfonamide N,N-Diisopropylethylamine (0.14 ml., 0.823 mmole, 2.5 eq.) was added to a solution of [βR-(βR*,γR*,δS*)]-δ-amino-N-butyl-β,γ-dihydroxycyclohexanepentanesulfonamide, monohydrochloride (122.8 mg., 0.329 mmole, 1 eq., product of Example 1) in dichloromethane (1.32 ml., 0.25M) at 0° and stirred for 15 minutes. Methanesulfonyl chloride (0.33 ml. of a 1.0M solution in dichloromethane, 0.33 mmole, 1 eq.) was then added dropwise. The ice bath was allowed to melt and the reaction was stirred at room temperature overnight. The reaction was then diluted with 0.5N HCl and extracted three times with ether. The organic extracts were filtered through MgSO$_4$ and concentrated. The residue was chromatographed on silica gel (Merck, 10 g.) eluting with choroform: methanol (30:1) to give 89.4 mg. of [βR-(βR*,γR*, δS*)]-N-butyl-β,γ-dihydroxy-δ-[(methylsulfonyl)amino]-cyclohexanepentanesulfonamide as a white foam; [α]$_D$=−6.5° (c=0.25, methanol). TLC (silica gel; chloroform:methanol, 30:1) R$_f$=0.13.

Anal. calc'd. for C$_{16}$H$_{34}$N$_2$O$_6$S$_2$: C, 46.35; H, 8.27; N, 6.76; S, 15.47 Found: C, 46.54; H, 8.39; N, 6.66; S, 15.46.

EXAMPLE 27

[βR-(βR*,γR*,δS*)]-δ-Amino-N-butyl-β,γ-dihydroxy-N-(phenylmethyl)cyclohexanesulfonamide, monohydrochloride a) [4S-[4α,5β(S*)]]-5-[2-[[(Butyl)(phenylmethy)amino]sulfonyl]-1-hydroxyethyl]-4-(cyclohexylmethyl)-2,2-dimethyl-3-oxazolidinecarboxylic acid, 1,1-dimethylethyl ester

[4S-[4α, 5β(S*)]]-5-[2-[(Butylamino)sulfonyl]-1-hydroxyethyl]-4 -(cyclohexylmethyl)-2,2-dimethyl-3-oxazolidinecarboxylic acid, 1,1-dimethylethyl ester (248 mg., 0.52 mmole, product of Example 1(d)], benzyl bromide (97.8 mg., 0.572 mmole) and freshly crushed and powdered anhydrous potassium carbonate (359 mg., 2.6 mmole) were stirred at room temperature in dimethylformamide (4 ml.) under argon for 19 hours. The reaction mixture was then diluted with diethyl ether (10 ml.) and treated with 5% aqueous potassium bisulfate (10 ml.) to a final pH of about 2.5. Water and ether (75 ml.) were added and the organic layer was separated, rinsed with brine, dried (MgSO$_4$) and concentrated in vacuo to give 311 mg. of crude product. Flash chromatography on silica gel (Merck, 16 g.) packed and eluted with hexane:ether (5:1) gave 291 mg. of [4S-[4α, 5β(S*)]]-5-[2 -[[(butyl)(phenylmethyl)amino]sulfonyl]-1-hydroxyethyl]-4-(cyclohexylmethyl)-2,2 -dimethyl-3-oxazolidinecarboxylic acid, 1,1-dimethylethyl ester as an oil. TLC (silica gel; hexane:ether, 3:1) R$_f$=0.26.

b) [βR-(βR*,γR*,δS*)]-δ-Amino-N-butyl-β,γ-
dihydroxy-N-(phenylmethyl)
cyclohexanepentanesulfonamide,
monohydrochloride The product from part (a) (62.4 mg., 0.11 mmole) was treated with a mixture of tetrahydrofuran (0.9 ml.), 10% aqueous HCl (0.6 ml.), and acetic acid (0.3 ml.) for 2 days at room temperature and stirred in a stoppered flask. The reaction mixture was then concentrated in vacuo, evaporated with toluene and finally treated with 4N HCl (15 ml.) in dioxane for 4 hours at room temperature. The reaction mixture was concentrated in vacuo, evaporated again with toluene and lyophilized to give 50 mg. of light yellow, solid [βR-(βR*,γR*,δS*)]-δ-amino-N-butyl-β,γ-dihydroxy-N-(phenylmethyl)cyclohexanepentanesulfonamide, monohydrochloride; m.p. 55°–110°; $[\alpha]_D = -1.6°$ (c=0.272, methanol); $[\alpha]_{Hg,365} = -4.7°$ (c=0.272, methanol). TLC (silica gel; chloroform: methanol:ammonia, 30:2:0.2) $R_f = 0.16$.

Anal. calc'd. for $C_{22}H_{38}N_2O_4S \cdot HCl \cdot 0.1 H_2O$: C, 56.85; H, 8.50; N, 6.03; Cl, 7.63; S, 6.90 Found: C, 56.85; H, 8.56; N, 6.04; Cl, 7.66; S, 6.57.

EXAMPLE 28

[βS-(βR*,γS*,δR*)]-δ-Amino-N-butyl-β,γ-
dihydroxy-N-(phenylmethyl)
cyclohexanepentanesulfonamide,
monohydrochloride a) [4S-[4α,5β(R*)]]-5-[2-[[(Butyl)(phenylmethyl)
amino]sulfonyl]-1-hydroxyethyl]-4-
(cyclohexylmethyl)-2,2-dimethyl-3-
oxazolidinecarboxylic acid, 1,1-dimethylethyl ester

[4S-[4α,5β(R*)]]-5-[2-[(Butylamino)sulfonyl]-1-hydroxyethyl]-4 -(cyclohexylmethyl)-2,2-dimethyl-3-oxazolidinecarboxylic acid, 1,1-dimethylethyl ester, isomer B [268 mg., 0.562 mmole, product of Example 1(d)], benzyl bromide (106 mg., 0.618 mmole) and freshly crushed and powdered anhydrous potassium carbonate (386 mg., 2.81 mmole) were reacted according to the procedure of Example 27(a) to give 303 mg. of [4S-[4α,5β(R*)]]-5-[2-[[(butyl)(phenylmethyl)amino]-sulfonyl]-1-hydroxyethyl]-4 -(cyclohexylmethyl)-2,2-dimethyl-3-oxazolidinecarboxylic acid,1,1-dimethylethyl ester as an oil. TLC (silica gel; hexane: ether, 3:1) $R_f = 0.12$.

b) [βS-(βR*,γS*,δR*)]-δ-Amino-N-butyl-β,γ-
dihydroxy-N-(phenylmethyl)
cyclohexanepentanesulfonamide,
monohydrochloride The product from part (a) (66 mg., 0.116 mmole) was treated with a mixture of tetrahydrofuran (0.9 ml.), 10% aqueous HCl (0.6 ml.), and acetic acid (0.3 ml.) for 5 days at room temperature and stirred in a stoppered flask. The reaction mixture was then concentrated in vacuo, evaporated with toluene, and lyophilized to give 53 mg. of solid [βS-(βR*,γS*,δR*)]-δ-amino-N-butyl-β,γ-dihydroxy-N-(phenylmethyl) cyclohexanepentanesulfonamide, monohydrochloride; m.p. 60°–110°; $[\alpha]_D = 0°$ (c=0.242, methanol). $[\alpha]_{Hg}365 = -9.8°$ (c=0.242, methanol). TLC (silica gel; chloroform:methanol:ammonia, 30:2:0.1) $R_f = 0.18$.

Anal. calc'd. for $C_{22}H_{38}N_2O_4S \cdot HCl$: C, 57.07; H, 8.49; N, 6.05; Cl, 7.66; S, 6.92 Found: C, 57.07; H, 8.67; N, 6.14; Cl, 7.63; S, 6.75.

EXAMPLE 29

[βR-(βR*, γR*, δS*)]-δ-Amino-N-
[(3,4-dimethoxyphenyl)methyl]-β,γ-
dihydroxycyclohexanepentanesulfonamide,
monohydrochloride a)
N-[(3,4-Dimethoxyphenyl)methyl]methanesulfonamide 1-(Aminomethyl)-3,4-dimethoxybenzene (18 ml., 120 mmole, 2 eq.) was added to a solution of methanesulfonyl chloride (4.64 ml., 60 mmole, 1 eq.) in dichloromethane (30 ml., 2.0M) at 0°. Additional dichloromethane (90 ml., final concentration of 0.5M) was then added. The reaction was allowed to warm to room temperature and stirred 2 days. The solid which had precipitated was filtered off and washed with additional dichloromethane. The filtrate was washed with 0.5N HCl (2×200 ml.) and water (200 ml.), dried (MgSO$_4$), filtered, and concentrated to give 13.93 g. of yellow solid. This material was recrystallized from ethyl acetate:hexane (1:1, 75 ml.). The crystalline product was washed with ethyl acetate:hexane (1:1) and ether and dried to give 12.41 g. of N-[(3,4-dimethoxy)methyl]methanesulfonamide; m.p. 78°–81°.

b) (4S-trans)-5-[[[[(3,4-Dimethoxyphenyl)methyl]-
amino]sulfonyl]acetyl]-4
-(cyclohexylmethyl)-2,2-dimethyl-3-
oxazolidinecarboxylic acid, 1,1-dimethylethyl ester n-Butyllithium (9.1 ml., 22.85 mmole, 2.5M in hexane) was added dropwise to a solution of N-[(3,4-dimethoxyphenyl)methyl]methanesulfonamide (2.92 g., 11.9 mmole, 2.5 eq.) in tetrahydrofuran (33 ml., 0.35M) at –40°. After 10 minutes, the reaction was warmed to 0° and stirred for 75 minutes. The mixture was recooled to –40° and (4S-trans)-4-(cyclohexylmethyl)-5-[[(methoxy)methylamino]carbonyl]-2,2 -dimethyl-3-oxazolidinecarboxylic acid, 1,1-dimethylethyl ester [1.83 g., 4.76 mmole, 1 eq., prepared as set forth in Example 1(b)] was added in tetrahydrofuran (10 ml., 0.5M). After two hours, the reaction was warmed to 0° C. After an additional two hours, the reaction was quenched with aqueous saturated NH$_4$Cl (10 ml.) and made strongly acidic with 1N HCl. The mixture was extracted with chloroform (2×100 ml.). The organic extracts were dried (MgSO$_4$), filtered and concentrated. The residue (4.98 g.) was chromatographed on Merck silica gel (200 g.) eluting with ether:hexane (5:3) to furnish 1.6 g. of (4S-trans)-5-[[[ [(3,4 -dimethoxyphenyl)methyl]amino]sulfonyl]acetyl]-4-(cyclohexylmethyl)-2,2 -dimethyl-3-oxazolidinecarboxylic acid, 1,1-dimethylethyl ester as a foam.

c) [4S-[4α,5β(S*)]]-and
[4S-[4α,5β(R*)]]-5-[2-[[[(3,4
-Dimethoxyphenyl)methyl]amino]sulfonyl]-1-
hydroxyethyl]-4-(cyclohexylmethyl)-2,2
-dimethyl-3-oxazolidinecarboxylic acid,
1,1-dimethylethyl ester Borane-tert-butylamine complex (266 mg., 3.06 mmole, 1.1 eq.) was added to a solution of the product from part (b) (1.58 g., 2.78 mmol., 1.0 eq.) in ether (21 ml., 0.12M) at 0° C. The ice bath was allowed to melt and the reaction was stirred at room temperature overnight. The mixture was then diluted with 1N HCl (40 ml.) and extracted twice with ether. The organic extracts were dried (MgSO$_4$), filtered and concentrated to provide 1.62 g. of crude foam. The residue was chromatographed on Merck silica gel (100 g.) eluting with benzene: ether (3:1) to provide [4S-[4α,5β(S*)]]-5-[2-[[[(3,4 -dimethoxyphenyl)methyl]amino]sulfonyl]-1-hydroxyethyl]--4-(cyclohexylmethyl)-2,2 -dimethyl-3-oxazolidinecarboxylic acid, 1,1-dimethylethyl ester (1.2 g. , 75%) and the [4S- [4α,5β(R*)]]isomer (0.3 g., 20%).

d) [βR-(βR*,γR,δS)]-δ-Amino-N-[(3,4-dimethoxyphenyl)methyl]-β,γ-dihydroxycyclohexanepentanesulfonamide, monohydrochloride 10% HCl (0.72 ml., 0.25M) and acetic acid (0.36 ml., 0.5M) were added to a solution of [4S-[4α,5β(S*)]] isomer product from part (c) (102 mg., 0.179 mmole, 1 eq.) in tetrahydrofuran (1.08 ml., 0.17M) and stirred at room temperature for 4 days. The reaction was concentrated. The residue was chromatographed on silica gel (Merck, 5 g.) eluting with chloroform:methanol:$NH_4OH$ (30:4: 0.05) to give the desired product as the free base (66.8 mg.). This material (66.8 mg., 0.155 mmole, 1 eq.) was dissolved in methanol (10 ml.) and treated with 1N HCl (0.155 ml., 0.155 mmole, 1 eq.). After 30 minutes at room temperature, the solution was concentrated. The residue was dissolved in water (10 ml.) and ethanol (1 ml.), filtered through a polycarbonate filter and lyophilized to give 75.7 mg. of white [βR-(βR*,γR*,δS*)]-δ-amino-N-[(3,4 -dimethoxyphenyl)methyl]-β,γ-dihydroxycyclohexanepentanesulfonamide, monohydrochloride; m.p. 93°–100°; $[α]_D$=−1.6° (c=0.75, methanol). TLC (silica gel; chloroform:methanol:$NH_4OH$, 30:4:0.05) $R_f$=0.23.

Anal. calc'd. for $C_{20}H_{34}N_2O_6S$ . 1.1 HCl . 0.2 $H_2O$: C, 50.65; H, 7.55; N, 5.91; Cl, 8.22; S, 6.76. Found: C, 50.61; H, 7.80; N, 5.79; Cl, 8.20; S, 6.55.

EXAMPLE 30

[62 R-(βR*,γR*,δS*)]-δ-Amino-β,γ-dihydroxycyclohexanepentanesulfonamide, monoacetate salt a) [4S-[4α,5β(S*)]]-5-[2-[[[(3,4-Dimethoxyphenyl)methylene]amino]sulfonyl]-1-hydroxyethyl]-4-(cyclohexylmethyl)-2,2-dimethyl-3-oxazolidinecarboxylic acid, 1,1-dimethylethyl ester 2,3-Dichloro-5,6-dicyano-1,4-benzoquinone (130.3 mg., 0.574 mmole, 1.3 eq.) was added to a solution of [4S-[4α, 5β(S*)]]-5-[2-[[[(3,4 -dimethoxyphenyl)methyl]amino]sulfonyl]-1-hydroxyethyl]-4-(cyclohexylmethyl)-2,2-dimethyl-3 -oxazolidinecarboxylic acid, 1,1-dimethylester [252 mg., 0.441 mmole, 1 eq., prepared as described in Example 29(c)] in dichloromethane:water (18:1, 4.4 ml., 0.1M) at room temperature and stirred for one hour. Additional 2,3-dichloro-5,6-dicyano-1,4-benzoquinone (130.3 mg., 0.574 mmole, 1.3 eq.) was then added and stirring continued for an additional hour. The reaction was diluted with dichloromethane and filtered. The filtrate was washed twice with aqueous sodium bicarbonate solution, dried ($Na_2SO_4$), filtered through $MgSO_4$ and concentrated. The residue was chromatographed on silica gel (Merck, 10 g.) eluting with ether: hexane (2:3 followed by 1:1 followed by 3:1) to give 149 mg. of [4S-[4α,5β(S*)]]-5-[2-[[[(3,4 -dimethoxyphenyl)methylene]amino]sulfonyl]-1-hydroxyethyl]-4-(cyclohexylmethyl)-2,2 -dimethyl-3-oxazolidinecarboxylic acid, 1,1-dimethylethyl ester.

b) [βR-(βR*,γR*,δS*)]-δ-Amino-β,γ-dihydroxycyclohexanepentanesulfonamide, monoacetate salt 10% HCl (1.0 ml., 0.25M) and acetic acid (0.5 ml., 0.5M) were added to a solution of the product from part (a)(136 mg., 0.24 mmole, 1 eq.) in tetrahydrofuran (1.5 ml., 0.17M) and stirred at room temperature for a total of 6 days. The reaction was then concentrated. The product was chromatographed on silica gel (Merck, 5 g.) eluting with chloroform:methanol:$NH_4OH$ (30:8:0.05) to give 71.7 mg. of the desired product as the free base. This material (71.7 mg., 0.256 mmole, 1. eq.) was dissolved in methanol (10 ml.) and treated with 1N HCl (0.256 ml., 0.256 mmole, 1 eq.). After 30 minutes at room temperature, the solution was concentrated. The residue was dissolved in water (10 ml.), passed through a polycarbonate filter, and lyophilized to give 61.6 mg. of crude monohydrochloride salt product. This material was chromatographed on silica gel (Merck, 5 g.) eluting with ethyl acetate:pyridine:acetic acid: water (10:1:1:1). The product was concentrated, dissolved in water (10 ml.) and lyophilized to give 55.3 mg. of material. This was dissolved in water (10 ml.) and ethanol (1 ml.), filtered through a polycarbonate filter, and lyophilized to give 39.3 mg. of white [βR-(βR*,γR*,δS*)]-δ-amino-β,γ-dihydroxycyclohexanepentanesulfonamide, monoacetate salt; m.p. 168°–170° (shrinking at 68°); $[α]_D$=−6.8° (c=0.40, methanol). TLC (silica gel; ethyl acetate:pyridine:acetic acid:water, 10:1:1:1) $R_f$=0.25.

Anal. calc'd. for $C_{11}H_{24}N_2O_4S$ . $CH_3COOH$ . 0.4 $H_2O$: C, 44.91; H, 8.35; N, 8.06; S, 9.22 Found: C, 44.93; H, 8.15; N, 8.30; S, 9.34.

EXAMPLE 31

[βR-(βR*,γR*,δS*)]-δ-Amino-N-butyl-γ-hydroxy-β-methoxycyclohexanepentanesulfonamide a) [4S-[4α,5β(S*)]]-5-[2-[[(Butyl)(phenylmethyl)amino]sulfonyl]-1-methoxyethyl]-4-(cyclohexylmethyl)-2,2-dimethyl-3-oxazolidinecarboxylic acid, 1,1-dimethylethyl ester To a solution of [4S-[4α,5β(S*)]]-5-[2-[[(butyl)(phenylmethyl)amino]sulfonyl]-1 -hydroxyethyl]-4-(cyclohexylmethyl)-2,2-dimethyl-3-oxazolidinecarboxylic acid, 1,1-dimethylethyl ester [222 mg., 0.392 mmole, product of Example 27(a)] in dry tetrahydrofuran (7 ml.) cooled to −20° C under argon was added 60% sodium hydride dispersion in oil (14.1 mg., 0.588 mmole.). After 15 minutes, dimethyl sulfate (84 mg., 0.666 mmole) was added neat and the temperature was raised to 0° C, and then to room temperature for a period of 1 hour during which time the reaction proceeded to completion. The reaction mixture was diluted with ether (15 ml.), then stirred with 5% aqueous potassium bisulfate (5 ml.) for about 15 minutes. The organic layer was then separated and combined with further ether extracts of the aqueous solution. The total organic extract was rinsed with brine, dried ($MgSO_4$) and concentrated in vacuo to provide 278 mg. of crude product. Flash chromatography on 34 g. of Merck silica gel eluted with 5:1, hexane: ether provided 216 mg. of [4S-[4α,5β(S*)]]-5-[2 -[[(butyl)(phenylmethyl)amino]sulfonyl]-1-methoxyethyl]-4-(cyclohexylmethyl)-2,2 -dimethyl-3-oxazolidinecarboxylic acid, 1,1-dimethylethyl ester. TLC (silica gel; hexane:ether, 2:1) $R_f$=0.50.

b) [4S-[4α,5β(S*)]],5-[2-[(Butylamino)sulfonyl]-
1-methoxyethyl]-4
-(cyclohexylmethyl)-2,2-dimethyl-3-
oxazolidinecarboxylic acid, 1,1-dimethylethyl ester
and [βR-(βR*, γR*,δS*)]-N-butyl-β-[[(1,1
-dimethylethoxy)carbonyl]amino]-γ-hydroxy-β-
methoxycyclohexanepentanesulfonamide To a solution of the product from part (a) (108 mg., 0.186 mmole) in glacial acetic acid (1.4 ml.) was added 20% palladium hydroxide on carbon (150 mg.). The reaction mixture was hydrogenated for 16 hours on a Parr apparatus at 50 psi, then concentrated in vacuo and partitioned between ethyl acetate (30 ml.) and saturated aqueous sodium bicarbonate (8 ml.). The organic extract was rinsed with brine, dried (MgSO$_4$), and evaporated to 81.2 mg. of crude product. Flash chromatography on silica gel (Merck, 9 g.) eluted with 2:1, ether:hexane provided 27.5 mg. of [4S-[4α, 5β(S*)]]-5-[2 -[(butylamino)sulfonyl]-1-methoxyethyl]-4-(cyclohexylmethyl)-2,2-dimethyl-3-oxazolidinecarboxylic acid, 1,1-dimethylethyl ester; TLC (silica gel; ether:hexane 2:1) R$_f$=0.57 and 43.6 mg. of [βR-(βR*,γR*,δS*)]-N-butyl-δ-[[(1,1 -dimethylethoxy)-carbonyl]amino]-γ-hydroxy-β-methoxycyclohexanepentanesulfonamide; TLC (silica gel; ether:hexane, 2:1) R$_f$=0.14.

c)
[βR-(βR*,γR*,δS*)]-δ-Amino-N-butyl-γ-hydroxy-β-
methoxycyclohexanepentanesulfonamide A mixture of the two products from part (b) (0.346 mmole, ratio of about 1:1) was treated with a solvent mixture comprising tetrahydrofuran (2.4 ml.), 10% aqueous HCl (1.6 ml.), and acetic acid (0.8 ml.). After stirring at room temperature for 4 days in a stoppered flask, the reaction mixture was concentrated in vacuo and evaporated in the presence of toluene. The residue was taken up in chloroform-methanol and treated with solid potassium carbonate, filtered, and evaporated to provide 135 mg. of crude product. Flash chromatography on silica gel (Merck, 10 g.) eluted with chloroform:methanol: ammonia (22:2:0.1 ) provided 101 mg. of white, solid [βR-(βR*, γR*,δS*)]-δ-amino-N-butyl-γ-hydroxy-β-methoxycyclohexane pentanesulfonamide; m.p. 154°–156°; [α]$_D$=–8.5° (c=1.19, methanol). TLC (silica gel; chloroform: methanol:ammonia, 17:2: 0.1) R$_f$=0.32.

Anal. calc'd. for C$_{16}$H$_{34}$N$_2$O$_4$S . 0.28 H$_2$O: C, 54.05; H, 9. 80; N, 7.88; S, 9.02 Found: C, 54.05; H, 9. 74; N, 7.80; S, 8.86.

EXAMPLE 32

[βS-(βR*,γS*,δR*)]-δ-Amino-N-butyl-δ-
hydroxy-β-methoxycyclohexanepentanesulfonamide a) [4S,[4α,5β(R*)]]-5-[2-[[(Butyl)(phenylmethyl)
amino]sulfonyl]-1
-methoxyethyl]-4-(cyclohexylmethyl)-2,2-
dimethyl-3-oxazolidinecarboxylic acid,
1,1-dimethylethyl ester To a solution of [4S-[4α,5β(R*)]]-5-[2-[[(butyl)(phenylmethyl)amino]sulfonyl]-1 -hydroxyethyl]-4-(cyclohexylmethyl)-2,2-dimethyl-3-oxazolidinecarboxylic acid, 1,1-dimethylethyl ester [211 mg., 0.372 mmole, product of Example 28(a)] in dry tetrahydrofuran (7 ml.) cooled to –15° under argon was added 60% sodium hydride dispersion in oil (13.4 mg., 0.558 mmole). After 15 minutes, dimethyl sulfate (79.8 mg., 0.633 mmole) was added neat and the reaction was worked up according to the procedure of Example 31(a) to provide 199 mg. of [4S-[4α,5β(R*)-5-[2 -[[(butyl)-(phenylmethyl)amino]sulfonyl]-1-methoxyethyl]-4-(cyclohexylmethyl)-2,2 -dimethyl-3-oxazolidine-carboxylic acid, 1,1-dimethylethyl ester. TLC (silica gel; hexane:ether, 2:1) R$_f$=0.35.

b) [4S-[4α,5β(R*)]]-5-[2-[(Butylamino)sulfonyl]-
1-methoxyethyl]-4
-(cyclohexylmethyl)-2,2-dimethyl-3-
oxazolidinecarboxylic acid, 1,1-dimethylethyl ester
and [βS-(βR*, γS*, δR*)]-N-butyl-δ-[[(1,1
-dimethylethoxy)carbonyl]amino]-γ-hydroxy-β-
methoxycyclohexanepentanesulfonamide To a solution of the product from part(a) (168 mg., 0.289 mmole) in glacial acetic acid (1.5 ml.) was added 20% palladium hydroxide on carbon (320 mg.). The reation mixture was hydrogenated and worked up according to the procedure of Example 31 (b) to give 36 mg. of [4S-[4α, 5β(R*)]]-5-[2 -[(butylamino)sulfonyl]-1-methoxyethyl]-4-(cyclohexylmethyl)-2,2-dimethyl-3-oxazolidinecarboxylic acid, 1,1-dimethylethyl ester; TLC (silica gel; ether:hexane, 3:1) R$_f$=0.66 and 92 mg. of [βS-(βR*, γS*,δR*)]-N-butyl-δ-[[(1,1 -dimethylethoxy)carbonyl]amino]-γ-hydroxy-β-methoxycyclohexanepentanesulfonamide; TLC (silica gel; ether:hexane, 3:1) R$_f$=0.21.

c)
[βS-(βR*,γS*,δR*)]-δ-Amino-N-butyl-Δ-hydroxy-β-
methoxycyclohexanepentanesulfonamide The mixture of the two products from part (b) (0.277 mmole, ratio of about 1:3) was treated with the same solvent mixture and worked up according to the procedure of Example 31(c) to give 81 mg. of waxy solid [βS-(βR*,γS*, δR*)]-δ-amino-N-butyl-γ-hydroxy-β-methoxycyclohexanepentanesulfonamide; m.p. 72°–82°; [α]$_D$=–26.9° (c=0.92, methanol). TLC (silica gel; chloroform:methanol:ammonia; 17:2:0.1) R$_f$=0.21.

Anal. calc'd. for C$_{16}$H$_{34}$N$_2$O$_4$S . 0.13 H$_2$O: C, 54.46; H, 9.79; N, 7.94; S, 9.09 Found: C, 54.46; H, 9.79; N, 8.81; S, 8.79.

EXAMPLE 33

[βR-(βR*,γR*,δS*)]-δ-Amino-δ,γ-dihydroxy-N-
(2-hydroxyethyl)cyclohexanepentanesulfonamide,
monoacetate salt a)
[4S-[4α,5β(S*)]]-4-(Cyclohexylmethyl)-5-[2-[[[(3,4
-dimethyoxyphenyl)methyl](2-ethoxy-2-oxoethyl)
amino]sulfonyl]-1-hydroxyethyl]-2,2-dimethyl-3
-oxazolidinecarboxylic acid, 1,1-dimethylethyl ester Ethyl bromoacetate (0.18 ml., 1.66 mmole, 1.1 eq.) was added to a solution of [4S-[4α,5β(S*)]]-4-(cyclohexylmethyl)-5-[2 -[[[(3,4-dimethoxyphenyl)methyl]amino]sulfonyl]-1-hydroxyethyl]-2,2-dimethyl-3-oxazolidinecarboxylic acid, 1,1-dimethylethyl ester [858.8 mg., 1.50 mmole, 1 eq., product of Example 29(c)] and potassium carbonate (1.04 g., 7.52 mmole, 5 eq.) in dimethylformamide (12.0 ml., 0.125M). The reaction was stirred at room temperature for 90 minutes and diluted with ether. Aqueous potassium bisulfate solution was added until the pH was 2. Water was added to dissolve the salts. The mixture was extracted with ether (3×50 ml.). The organic residue was dried (Na$_2$SO$_4$), filtered through MgSO$_4$, and concentrated. The residue was chromatographed on silica gel (Merck, 60 g.) eluting with ether:hexane (1:1) to give 980 mg. of [4S-[4α,5β(S*)]-4-(cyclohexylmethyl)-5-[2 -[[[(3,4-dimethoxyphenyl)methyl] (2-ethoxy-2-oxoethyl)amino]sulfonyl]-1-hydroxyethyl]-2,2 -dimethyl-3-oxazolidinecarboxylic acid, 1,1-dimethylethyl ester; [α]$_D$=−7.4° (c=1.0, methanol).

b)
[4S-[4α,5β(S*)]-4-(Cyclohexylmethyl)-5-[2-[[[(3,4 -dimethoxyphenyl)methyl](2-hydroxyethyl)amino] sulfonyl]-1-hydroxyethyl]-2,2-dimethyl-3- oxazolidinecarboxylic acid, 1,1-dimethylethyl ester Lithium aluminum hydride (0.69 ml., 0.69 mmole, 1.5 eq., 1.0M in tetrahydrofuran) was added dropwise to a solution of the product from part (a) (301.9 mg., 0.46 mmole, 1 eq.) in ether (4.6 ml., 0.1M) at 0°. After 30 minutes, the reaction was quenched by the dropwise addition of aqueous 1N HCl. The mixture was extracted with ether (3×20 ml.). The organic extracts were dried (Na$_2$SO$_4$), filtered through MgSO$_4$, and concentrated. The residue was chromatographed on silica gel (Merck, 10 g.) eluting with ether: hexane (3:1) to provide 256 mg. of [4S-[4α, 5β(S*)] ]-4-(cyclohexylmethyl)-5-[2-[[[(3,4-dimethoxyphenyl)m ethyl](2 -hydroxyethyl)amino]sulfonyl]-1-hydroxyethyl]-2, 2-dimethyl-3-oxazolidinecarboxylic acid, 1,1-dimethylethyl ester; [α]$_D$=−5.3° (c=1.0, methanol).

c)
[4S-[4α,5β(S)*]]-4-(Cyclohexylmethyl)-5-[2-[[-(2 -hydroxyethyl)amino]sulfonyl]-1-hydroxyethyl]- 2,2-dimethyl-3-oxazolidinecarboxylic acid, 1,1-dimethylethyl ester The product from part (b) (231.3 mg., 0.38 mmole, 1 eq.) was combined with palladium hydroxide on carbon (57.8 mg., 25% by weight) in ethanol (3.76 ml., 0.1M) and stirred at room temperature under a balloon of hydrogen. Additional palladium hydroxide on carbon (2×60 mg.) was added after day 2 and day 3 of the reaction. After 5 days, the reaction was filtered through regenerated cellulose and concentrated. The residue was dissolved in ethanol (4 ml., 0.1M), treated with palladium hydroxide on carbon (120 mg., 50% by weight) and stirred under a balloon of hydrogen for one day. Additional palladium hydroxide on carbon (120 mg.) was added and the reaction continued for 4 more days until no starting material was observed. The reaction was diluted with methanol, filtered through regenerated cellulose, and concentrated. The residue was chromatographed on silica gel (Merck, 10 g.) eluting with chloroform:methanol (30:1) to give 94.2 mg. of solid [4S-[4α,5β(S*)]]-4-(cyclohexylmethyl)-5 -[2-[[(2-hydroxyethyl)amino]sulfonyl]-1-hydroxyethyl]-2,2-dimethyl-3-oxazolidinecarboxylic acid, 1,1-dimethylethyl ester; m.p. 174°–177°; [α]$_D$=+14.5° (c=1.0, chloroform: methanol, 10:1).

d) [βR-(βR*,γR*,δS*)]-δ-Amino-β,γ-dihydroxy-N- (2-hydroxyethyl)cyclohexanepentanesulfonamide, monoacetate salt Aqueous 10% HCl (0.85 ml., 0.25M) and acetic acid (0.42 ml., 0.5M) were added to a solution of the product from part (c) (94 mg., 0.21 mmole, 1 eq.) in tetrahydrofuran (1.28 ml., 0.17M) and stirred at room temperature for a total of 6 days. The reaction was concentrated. The residue was chromatographed on Merck silica gel (5 g.) eluting with ethyl acetate:pyridine:acetic acid:water (15:1:1:1) followed by (10:1:1:1) to give 82.5 mg. of crude product. This material was dissolved in water (10 ml.) and ethanol (1 ml.), filtered through a polycarbonate filter, and lyophilized to give 68 mg. of solid [βR-(βR*,γR*,δS*)]-δ-amino-β,γ-dihydroxy-N-(2 -hydroxyethyl)cyclohexanepentanesulfonamide, monoacetate salt; m.p. 60°–65°; [α]$_D$=−1.7° (c=1.0, methanol). TLC (silica gel; ethyl acetate:pyridine:acetic acid:water, 10:1:1:1) R$_f$=0.21.

Anal. calc'd. for C$_{13}$H$_{28}$N$_2$O$_5$S . CH$_3$COOH . 0.4 H$_2$O: C, 46.00; H, 8.44; N, 7.15; S, 8.18 Found: C, 46.06; H, 8.44; N, 7.21; S, 7.90.

EXAMPLE 34

[βR-(βR*,γR*,δS*)]-δ-Amino-N-butyl-β,γ-dihydroxy-N- methylcyclohexanepentanesulfonamide, monohydrochloride a)
[4S-[4α,5β(S*)]]-5-[2-[(Butyl)(methylamino)sulfonyl]- 1-hydroxyethyl]-4 -(cyclohexylmethyl)-2,2-dimethyl-3- oxazolidinecarboxylic acid, 1,1-dimethylethyl ester

[4S-[4α,5β(S*)]]-5-[2-[(Butylamino)sulfonyl]-1-hy-droxyethyl]-4 -(cyclohexylmethyl)-2,2-dimethyl-3-oxazo-lidinecarboxylic acid, 1,1-dimethylethyl ester (100 mg. 0.21 mmole, 1 eq.), prepared as described in Example 1(d), was dissolved in dimethylformamide (0.84 ml., 0.25M). Powdered potassium carbonate (145 mg., 1.05 mmole, 5 eq.) and dimethyl sulfate (99 μl., 1.05 mmole, 5 eq.) were added and the mixture was stirred under an argon atmosphere. After 24 hours, an additional amount of potassium carbonate (2.5 eq.) and dimethyl sulfate (5 eq.) were added with continued stirring at 45° for 8 hours. The mixture was quenched with an aqueous solution of 10% potassium bisulfate until acidic, extracted hexane:ether (1:1, 3×30 ml.), and washed with saturated sodium chloride solution and water. The organic phase was dried (MgSO$_4$) and freed of solvent in vacuo. The crude product was purified by flash chromatography (6 g. silica, eluted with 1:2, ether:hexane) and freed of solvent in vacuo to give 62 mg. of [4S-[4α,5β(S*)]]-5-[2-[(butyl)(m-ethylamino)sulfonyl]-1 -hydroxyethyl]-4-(cyclohexylm-ethyl)-2,2-dimethyl-3-oxazolidinecarboxylic acid, 1,1-dimethylethyl ester. TLC (silica gel; ether:hexane, 1:1) R$_f$=0.5.

b)
[βR-(βR*,γR*,δS*)]-δ-Amino-N-butyl-β,γ-dihydroxy- N-methylcyclohexanepentanesulfonamide, monohydrochloride The product from part (a) (62 mg., 0.126 mmole) was dissolved in a 3:2:1 mixture of tetrahydrofuran, 10% HCl, and glacial acetic acid (6 ml., 4 ml., 2 ml., respectively), and stirred at room temperature for 48 hours. The solvents were removed in vacuo and the product was then chromatographed (5 g. Merck silica, eluted with 5% methanol in dichloromethane, NH$_4$OH) and freed of solvent in vacuo to yield 40 mg. of a white solid. This product was dissolved in methanol and treated with 1N HCl (0.114 ml., 1 eq.) and rotary evaporated to dryness. This material was then dissolved in water (6 ml.), filtered through a polycarbonate filter, and lyophilized to give 26 mg. of solid [βR-(βR*,γR*, δS*)]-δ-Amino-N-butyl-β,γ-dihydroxy-N-methylcyclohex-anepentanesulfonamide, monohydrochloride; m.p.-103°–107° (shrinking at 100°); [α]$_D$=−2.04° (c=0.5, methanol). TLC (silica gel; 5% methanol in dichloromethane plus 0.2% NH$_4$OH) $R_f$=0.1.

Anal. calc'd. for C$_{16}$H$_{34}$N$_2$O$_4$S . HCl . 0.8H$_2$O: C, 47.88; H, 9.19; N, 6.98; Cl, 8.83; S, 7.99 Found C, 47.86; H, 9.09; N, 6.79; Cl, 8.93; S, 7.96.

In a similar manner, [βS-(βR*,γS*,δR*)]-δ-amino-N-butyl-β,γ-dihydroxy-N-methylcyclohexanepentane-sulfonamide, monohydrochloride was obtained, m.p. 70°–83° (shrinking at 60°); [α]$_D$=−6.4° (c=0.6, methanol). TLC (silica gel, 5% methanol in dichloromethane +0.2% NH$_4$OH) $R_f$=0.21.

Anal. calc'd. for C$_{16}$H$_{34}$N$_2$O$_4$S . HCl . 0.25 H$_2$O: C, 49.09; H, 9.14; N, 7.16; Cl, 9.06; S, 8.19 Found: C, 49.16; H, 9.23; N, 7.08; C$_{1.9,18}$; S, 8.01.

EXAMPLE 35

[βS-(βR*, γS*,δR*)]-δ-Amino-β,γ-dihydroxy-N-(2-hydroxyethyl)cyclohexanepentanesulfonamide, diacetate salt a) N-(Diphenylmethyl)methanesulfonamide

Aminodiphenylmethane hydrochloride (6.92 g., 31.5 mmole, 1.05 eq.) was dissolved in dichloromethane (150 ml., 0.2M) and cooled in an ice bath. Triethylamine (10.5 ml., 75 mmole, 2.5 eq.) was added and the mixture was stirred for 15 minutes. Methanesulfonyl chloride (2.32 ml., 30 mmole, 1 eq.) was added dropwise at 0°. After the addition was complete, the reaction was warmed to room temperature and stirred overnight. The mixture was washed with 0.5N HCl solution (2×100 ml.) and saturated sodium chloride solution (100 ml.), dried (Na$_2$SO$_4$ and MgSO$_4$) and freed of solvent in vacuo to give 7.66 g. of N-(diphenylmethyl)methanesulfonamide as a solid; m.p. 148°–150°. TLC (silica gel, ether:hexane, 1:1) $R_f$=0.31.

b) (4S-trans)-5-[[[(Diphenylmethyl)sulfonyl]amino]acetyl]-4-(cyclohexylmethyl)-2,2-dimethyl-3-oxazolidinecarboxylic acid, 1,1-dimethylethyl ester N-(Diphenylmethyl)methanesulfonamide (6.34 g., 19.5 mmole, 2.5 eq.) and lithium chloride (1.65 g., 39 mmole, 5 eq.) were partially dissolved in distilled tetrahydrofuran (78 ml., 0.25M) and cooled to −40°. n-Butyllithium (2.5M in hexane, 15.6 ml., 39 mmole, 5 eq.) was added slowly. The mixture was stirred at −40° for 30 minutes and then warmed to 0° for 30 minutes. After recooling to −40°, (4S-trans)-4-(cyclohexylmethyl)-5-[[(methoxy)methylamino]carbonyl]-2,2 -dimethyl-3-oxazolidinecarboxylic acid, 1,1-dimethylethyl ester [3.0 g., 7.8 mmole, 1 eq., prepared as described in Example 1(b)] was added. The reaction was stirred at −40° for 30 minutes and at 0° for 30 minutes, then quenched with 1N HCl (50 ml.). The product was extracted into ether (3×75 ml.), dried (Na$_2$SO$_4$ and MgSO$_4$), and freed of solvent in vacuo. The product was purified by chromatography on silica gel (270 g. Merck) eluting with ether:hexane (1:3) followed by (1:2) to give 4.45 g. of (4S-trans)-5-[[[(diphenylmethyl)sulfonyl]-amino]acetyl]-4 -(cyclohexylmethyl)-2,2-dimethyl-3-oxazolidinecarboxylic acid, 1,1-dimethylethyl ester; [α]$_D$=+30.3° (c=1.0, methanol). TLC (silica gel; ether:hexane, 1:1) $R_f$=0.56.

c) [4S-[4α,5β(S*)]]- and [4S-[4α,5β(R*)]]-5-[2-[[(Diphenylmethyl)sulfonyl]amino]-1-hydroxyethyl]-4-(cyclohexylmethyl)-2,2-dimethyl-3-oxazolidinecarboxylic acid, 1,1-dimethylethyl ester The product from part (b) (4.43 g., 7.576 mmole, 1 eq.) was dissolved in ether (30.3 ml., 0.25M), cooled to 0°, and treated dropwise with a 1M solution of potassium triethyl-borohydride (15.2 ml., 15.2 mmole, 2 eq.). The mixture was stirred at 0° for one hour. Lithium borohydride (41.2 mg., 1.894 mmole, 0.25 eq.) was added and the mixture was stirred at 0° for one hour and then at room temperature for one hour. Additional lithium borohydride (41.2 mg., 1.894 mmole, 0.25 eq.) was added and the reaction was left stirring overnight at room temperature. After cooling to 0°, the reaction was quenched with 1N HCl (50 ml.). The product was extracted into ether (3×50 ml.), dried (Na$_2$SO$_4$ and MgSO$_4$), and freed of solvent in vacuo. The remaining material was chromatographed on silica gel (100 g., Merck) eluting with ether:hexane (1:2.75) followed by (1:1.5) followed by (2:1) to give 886.6 mg. of isomer A as a solid foam; m.p. 58°–65°, TLC (silica gel, ether:hexane, 1:1) $R_f$=0.43; 2.55 g. of isomer B, TLC (silica gel, ether:hexane, 1:1) $R_f$=0.35; and 990 mg. of a mixture of isomer A and B.

d) [4S-[4α,5β(R*)]]-5-[2-[[(Diphenylmethyl)(2-ethoxy-2-oxoethyl)amino]sulfonyl]-1-hydroxyethyl]-4-(cyclohexylmethyl)-2,2-dimethyl-3-oxazolidinecarboxylic acid, 1,1-dimethylethyl ester To a solution of isomer B from part (c) (600 mg., 1.022 mmole, 1 eq.) in dimethylformamide (2.0 ml., 0.5M) was added powdered potassium carbonate (710 mg., 5.112 mmole, 5 eq.) and ethyl bromoacetate (227 µl., 2.044 mmole, 2 eq.). The reaction was stirred at 45°±5° overnight. The reaction was quenched with 10% aqueous potassium bisulfate and extracted with ether:hexane (1:1, 3×30 ml.). The extracts were combined, washed with water (50 ml.) and saturated sodium chloride solution, dried (MgSO$_4$), filtered, and freed of solvent in vacuo. The residue was purified by chromatography on silica gel (Merck, 60 g.) eluting with ether:hexane (1:2) to give 520 mg. of [4S-[4α,5β(R*)]]-5-[2-[[(diphenylmethyl)(2-ethoxy-2 -oxoethyl)amino]sulfonyl]-1-hydroxyethyl]-4-(cyclohexylmethyl)-2,2-dimethyl-3-oxazolidinecarboxylic acid, 1,1-dimethylethyl ester.

e) [4S-[4α,5β(R*)]]-5-[2-[[(2-Ethoxy-2-oxoethyl)-amino]sulfonyl]-1-hydroxyethyl]-4-(cyclohexylmethyl)-2,2-dimethyl-3-oxazolidinecarboxylic acid, 1,1-dimethylethyl ester 20% Palladium hydroxide on carbon catalyst (103 mg., 20% by weight) and triethylamine (84 µl., 0.764 mmole, 1 eq.) were added to a solution of the product from part (d) (514 mg., 0.764 mmole, 1 eq.) in a mixture of ethanol:tetrahydrofuran (3:1, 3.0 ml., 0.25M). The reaction was stirred under a hydrogen atmosphere at room temperature. After stirring overnight, the reaction was diluted with ethanol, filtered through regenerated cellulose, and concentrated in vacuo to give 515 mg. of crude product. This residue was purified by chromatography on silica gel (Merck, 40 g.) eluting with ether:hexane (1:2) to give 339 mg. of [4S-[4α,5β(R*)]]-5-[2-[[(2-ethoxy-2 -oxoethyl)amino]sulfonyl]-1-hydroxyethyl]-4-(cyclohexylmethyl)-2,2-dimethyl-3-oxazolidinecarboxylic acid, 1,1-dimethylethyl ester.

f) [4S-[4α,5β(R*)]]-5-[2-[[2-Hydroxyethyl)amino]sulfonyl]-1 -hydroxyethyl]-4-(cyclohexylmethyl)-2,2-dimethyl-3-oxazolidinecarboxylic acid, 1,1-dimethylethyl ester The product from part (e) (200 mg., 0.39 mmole, 1 eq.) was dissolved in anhydrous ether (3.9 ml., 0.1M). After cooling to 0°, lithium aluminum hydride (0.59 ml., 1M in tetrahydrofuran, 0.59 mmole, 1.5 eq.) was added dropwise. The reaction was stirred one hour at 0° before being quenched with 1N HCl solution. The reaction was extracted with ether. The ethereal extracts were dried (MgSO₄), filtered and freed of solvent in vacuo to give 177 mg. of a white foam. This material was purified by chromatography on silica gel (Merck, 15 g.) packed in acetone:hexane (1:4) and eluted with acetone:hexane (1:4 and 1:3) to yield 129 mg. of [4S-[4α,5β(R*)]]-5-[2-[[(2-hydroxyethyl)amino]sulfonyl]-1-hydroxyethyl]-4-(cyclohexylmethyl)-2,2-dimethyl-3-oxazolidinecarboxylic acid, 1,1-dimethylethyl ester.

g) [βS-(βR*,γS*,δR*)]-δ-Amino-β,γ-dihydroxy-N-(2-hydroxyethyl)cyclohexanepentanesulfonamide, diacetate salt The product form part (f) (126 mg., 0.271 mmole) was dissolved in a mixture of distilled tetrahydrofuran (3 ml.), 10% HCl (2 ml.) and acetic acid (1 ml.). After stirring at room temperature for 4 days, the reaction was concentrated in vacuo and chased with toluene. The residue was purified by chromatography. The product was preabsorbed on silica gel (Baker, 2 g.), applied to a silica gel column (Merck, 8 g.) and eluted with ethyl acetate:pyridine: acetic acid:water (10:1:1:0.5). The product fractions were combined, concentrated to near dryness, and chased with toluene. The residue was dissolved in water (15 ml.) and ethanol (5 ml.) and lyophilized. The compound was dissolved in water (20 ml.) and relyophilized to give 77 mg. of product. This was dissolved in water (20 ml.) and ethanol (2 ml.), filtered through a polycarbonate membrane, and lyophilized to yield 57 mg. of solid [βS-(βR*,γS*,δR*)-δ-amino-β,γ-dihydroxy-N-(2-hydroxyethyl)cyclohexanepentanesulfonamide, diacetate salt; m.p. 57°–160°; [α]$_D$=–18.2° (c=1.5, methanol: water, 1:1). TLC (silica gel, ethyl acetate: pyridine:acetic acid:water, 5:1:1:1)R$_f$=0.35.

Anal. calc'd. for C₁₃H₂₈N₂O₅S . 2CH₃COOH . 1.1H₂O: C, 43.97; H, 8.29; N, 6.03; S, 6.90 Found: C, 43.93; H, 7.97; N, 6.14; S, 7.05.

EXAMPLE 36

[2S-(2R*,3S*,4R*)]-N-[(4-Amino-5-cyclohexyl-2,3-dihydroxypentyl)sulfonyl]glycine, monolithium salt

[4S-[4α,5β(R*)]]-5-[2-[[(2-Ethoxy-2-oxoethyl)amino]sulfonyl]-1-hydroxyethyl]-4-(cyclohexylmethyl)-2,2-dimethyl-3-oxazolidinecarboxylic acid, 1,1-dimethylethyl ester [140 mg., 0.276 mmole, prepared as described in Example 35(e)] was treated with distilled tetrahydrofuran (3 ml.), 10% aqueous HCl (2 ml.), and acetic acid (1 ml.). The solution was stirred at room temperature for 5 days. The mixture was taken to dryness in vacuo. The residue was chromatographed on silica gel (8 g., Merck) eluting with ethyl acetate:pyridine:acetic acid:water (10:1:1:0.5) followed by (8:1:1:1) followed by (5:1:1:1). The product containing fractions were combined and taken to near dryness in vacuo. Water (20 ml.) was added and the solution was lyophilized to give 91 mg. of a very insoluble material. Water (5 ml.) was added to this and the suspension was treated with 1N lithium hydroxide solution (0.29 ml.). Most of the solid dissolved. The solution was washed with dichloromethane (2×10 ml.) and then lyophilized. The remaining material was passed through an LH-20 column, eluting with water. The fractions containing product were combined and lyophilized to give 91 mg. This sample was relyophilized and half of the resulting material was then purified in a column packed with HP-20 (22 ml.), eluting first with water (150 ml.) and then with 5% acetone in water. The pure product containing fractions were combined and lyophilized to give 32 mg. of white solid [2S-(2R*,3S*,4R*)]-N-[(4-amino-5-cyclohexyl-2,3-dihydroxypentyl)sulfonyl]glycine, mono-lithium salt; m.p. 220°–242° (dec.), shrinking at 130°; [α]$_D$=–8.6° (c=0.2, 10% methanol in water). TLC (silica gel, ethyl acetate:pyridine:acetic acid:water, 5:1:1:1) R$_f$=0.23.

Anal. Calc'd. for C₁₃H₂₅N₂O₆S . Li . 0.4H₂O: C, 44.41; H, 7.40; N, 7.97; S, 9.12 Found: C, 44.53; H, 7.65; N, 7.75; S, 8.99.

EXAMPLE 37

(1S,2R,3R)-N-[4-[(Butylamino)sulfonyl]-1-(cyclohexylmethyl)-2,3-dihydroxybutyl]-β-ethyl-1H-imidazole-4-propanamide, isomer 1 and isomer 2 a) α-Ethyl-1H-imidazole-4-propanoic acid

To a suspension of sodium hydride (500 mg. of 60% dispersion in oil, 12.6 mmole) in dimethylformamide (20 ml.) was added diethyl malonate (0.64 ml., 4.2 mmole). The resulting mixture was stirred for 30 minutes at 25°, after which 4-(1-chloropropyl)-1H-imidazole [760 mg., 4.2 mmole, prepared as described by Kelley et al., Jo Med. Chem., Vol. 20, p 721 (1977)] was added. The mixture was stirred for 18 hours, then poured into water (200 ml.) and extracted with ethyl acetate (3×75 ml.). The extract was dried and concentrated. The residue was flash chromatographed on silica gel (65 g.), eluting with 10:1 ethyl acetate:(pyridine 20:acetic acid 6:water 11) to give 700 mg. of [1-(1H-imidazole-4-yl)propyl]-propanedioic acid, diethyl ester.

A mixture of this diethyl ester (709 mg., 2.6 mmole), 1.0N sodium hydroxide solution (7 ml., 7 mmole), and ethanol (7 ml.) was stirred at 25° for 7 days, after which it was concentrated in vacuo. The residue was dissolved in 1N HCl (15 ml.) and applied to a column of AG-50W-X2 ion exchange resin (proton form). The column was eluted with water until the eluant had neutral pH, then with 2% aqueous NH₄OH solution. Fractions containing the desired product were combined and concentrated. The residue was crystallized from absolute ethanol to give 330 mg. of α-ethyl-1H-imidazole-4-propanoic acid; m.p. 166°–168°.

b) (1S,2R,3R)-N-[4-[(Butylamino)sulfonyl]-1-(cyclohexylmethyl)-2,3-dihydroxybutyl]-β-ethyl-1H-imidazole-4-propanamide, isomer 1 and isomer 2

A mixture of [βR-(βR*,γR*,δS*)]-δ-amino-N-butyl-β,γ-dihydroxycyclohexanepentanesulfonamide, monohydrochloride (186 mg., 0.5 mmole, product of Example 1), α-ethyl-1H-imidazole-4-propanoic acid (102 mg., 0.5 mmole), 1-(3-dimethylaminopropyl)-3-ethyl carbodiimide hydrochloride (96 mg., 0.5 mmole), 1-hydroxybenzotriazole hydrate (77 mg., 0.5 mmole) and triethylamine (0.14 ml., 1 mmole) in dimethylformamide (1.0 ml.) was stirred at 25° for 17 hours, after which it was concentrated in vacuo. The residue was flash chromatographed on silica gel, eluting with 90:10:1 chloroform:methanol:NH₄OH, to give a major fraction consisting of 2 components. This major fraction was concentrated and rechromatographed, eluting with 95:5:1 chloroform:methanol: NH₄OH to give 40 mg. samples of isomer 1 and isomer 2.

The isomer 1 sample was lyophilized from aqueous ethanol to give white solid (1S,2R,3R)-N-[4-[(butylamino) sulfonyl]-1 -(cyclohexylmethyl)-2,3-dihydroxybutyl]-α-ethyl-1H-imidazole-4-propanamide, isomer 1; m.p. 75°–100°; $[\alpha]_D = -17°$ (c=0.1, methanol). TLC (silica gel; chloroform:methanol: $NH_4OH$, 80:20:1) $R_f$=0.7.

Anal. calc'd. for $C_{23}H_{42}N_4O_5S \cdot 0.32\ H_2O$: C, 56.10; H, 8.73; N, 11.38; S, 6.51 Found: C, 56.10; H, 8.78; N, 11.20; S, 6.69.

The isomer 2 sample was also lyophilized from aqueous ethanol to give white solid (1S,2R, 3R)-N-[4-[(butylamino) sulfonyl]-1-(cyclohexylmethyl)-2,3-dihydroxybutyl]-α-ethyl-1H-imidazole-4 -propanamide, isomer 2; m.p. 60°–90°; $[\alpha]_D = -27°$ (c=0.1, methanol). TLC (silica gel; chloroform: methanol:$NH_4OH$, 80:20:1) $R_f$=0.65.

Anal. Calc'd. for $C_{23}H_{42}N_4O_5S \cdot 0.32\ H_2O$ C, 56.10; H, 8.73; N, 11.38; S, 6.51

Found: C, 56.09; H, 8.76; N, 11.21; S, 6.32.

EXAMPLE 38

[1S-(1R*,2S*,3S*)]-N-[4-[(Butylamino)sulfonyl]-1-(cyclohexylmethyl)-2,3 -dihydroxybutyl]-4-methyl-pentanamide Diisopropylethylamine (0.32 ml., 1.83 mmole) was added to a cooled (5°) dimethylformamide solution of [βR-(βR*, γR*,δS*)]-δ-amino-N-butyl-β, γ-dihydroxycyclohexanepentanesulfonamide, monohydrochloride (310 mg., 0.83 mmole, product of Example 1), 4-methylpentanoic acid (92.8 mg., 0.83 mmole) and 1-hydroxybenzotriazole hydrate (112 mg., 0.83 mmole) followed by the portionwise addition of 1-(3-dimethylaminopropyl)-3-ethylcarbodiimide hydrochloride (159 mg., 0.83 mmole). The reaction mixture was stirred at room temperature overnight, diluted with water (10 ml.), and the product was extracted with ethyl acetate (2×50 ml.). This was washed with saturated aqueous bicarbonate and brine, dried ($MgSO_4$), filtered, and concentrated. The crude product was purified by silica gel chromatography using a (7:3) hexane: ethyl acetate solvent system. The product containing fractions were combined and concentrated to yield 270 mg. of white solid [1S-(1R*,2S*,3S*)]-N-[4-[(butylamino)sulfonyl]-1 -(cyclohexylmethyl)-2,3-dihydroxybutyl]-4-methylpentanamide; m.p. 104°–105°; $[\alpha]_D = -17.5°$ (c=0.57, methanol). TLC (silica gel; methanol:chloroform, 1:9) $R_f$=0.66.

Anal. calc'd. for $C_{21}H_{42}N_2O_5S$: C, 58.03; H, 9.74; N, 6.45; S, 7.38 Found: C, 58.19; H, 10.05; N, 6.34; S, 7.40.

In a similar manner, 4-methylpentanoic acid was reacted with the product of Example 2 to give [1S-(1R*,2S*,3R*)] -N-[4-[(butylamino)sulfonyl]-1-(cyclohexylmethyl)-2,3 -dihydroxybutyl]-4-methylpentanamide, m.p. 88°–92°; $[\alpha]_D = -25.1°$ (c=0.45, methanol). TLC (silica gel, methanol:chloroform, 1:9) $R_f$=0.71.

Anal. calc'd. for $C_{21}H_{42}N_2O_5S$: C, 58.03; H, 9.74; N, 6.45; S, 7.38 Found: C, 57.76; H, 9.83; N, 6.43; S, 7.36.

EXAMPLE 39

[2S-[2R*,N(1R*,2S*,3S*)]]-N-[4-[(Butylamino)sulfonyl]-1 -(cyclohexylmethyl)-2,3-dihydroxybutyl]-2-hydroxy-4-methylpentanamide 1-(3-Dimethylaminopropyl)-3-ethylcarbodiimide hydrochloride (128.5 mg., 0.67 mmole) was added portionwise to a dimethylformamide (8 ml.) solution of [βR-(βR*,γR*, δS*)]-δ-amino-N-butyl-β,γ-dihydroxycyclohexanepentanesulfonamide, monohydrochloride (250 mg., 0.67 mmole, product of Example 1), L-α-hydroxyisocaproic acid (88.5 mg., 0.67 mmole), 1-hydroxybenzotriazole hydrate (90.6 mg., 0.67 mmole), and diisopropylethylamine (0.23 ml., 1.34 mmole). The reaction mixture was stirred under argon at room temperature overnight, diluted with water (20 ml.), and the product was extracted with ethyl acetate (2×100 ml.). This was washed with pH7 buffer and brine, dried ($MgSO_4$), filtered, and concentrated in vacuo. Crude product was chromatographed through silica gel (80 g., Merck) using a 2% methanol:dichloromethane system. The product containing fractions were combined and concentrated to yield 0.25 g. of white solid [2S-[2R*,N(1R*,2S*,3S*)]]-N-[4-[(butylamino)sulfonyl]-1 -(cyclohexylmethyl)-2,3-dihydroxybutyl]-2-hydroxy-4-methylpentanamide; m.p. 140°–145°; $[\alpha]_D = -38°$ (c=0.4, methanol). TLC (silica gel; methanol:chloroform, 1:9) $R_f$=0.46.

Anal. calc'd. for $C_{21}H_{42}N_2O_6S \cdot 0.01\ H_2O$: C, 55.95; H, 9.40; N, 6.21; S, 7.11 Found: C, 56.09; H, 9.80; N, 6.07; S, 6.88.

EXAMPLE 40

(1R*,2S*,3S*)-(1-Oxo-3-phenylpropyl)-N-[4-[(butylamino)sulfonyl]-1 -(cyclohexylmethyl)-2,3-dihydroxybutyl]-L-leucinamide a) N-(1-Oxo-3-phenylpropyl)-L-leucine

L-Leucine (7.87 g., 60 mmole, 1 eq.) was dissolved in a solution of sodium hydroxide (4.8 g., 120 mmole, 2 eq.) in water (40 ml., 1.5M). Diethyl ether (40 ml.) was added. The mixture was cooled in an ice bath and while stirring rapidly, hydrocinnamoyl chloride (10.1 g., 8.92 ml., 60 mmole) was added dropwise over a period of 30 minutes. The ice bath was removed and the mixture was stirred at room temperature for 2 hours maintaining a slightly basic pH by periodic addition of small amounts of 1N sodium hydroxide solution. The layers were separated. The ether layer was reextracted with 1N sodium hydroxide solution. The combined aqueous layers were washed once with ether and then acidified with concentrated HCl. The product was extracted into chloroform, dried ($MgSO_4$), and freed of solvent in vacuo leaving 13.36 g. of white solid. This material was recrystallized from ethyl acetate (65 ml.) to give 8.37 g. of N-(1-oxo-3-phenylpropyl)-L-leucine; m.p. 129°–130° (shrinking at 120°); $[\alpha]_D = -41.3°$ (c=1,3, methanol)

b) (1R*,2S*,3S*)-(1-Oxo-3-phenylpropyl)-N-[4-[(butylamino)sulfonyl]-1 -(cyclohexylmethyl)-2,3-dihydroxybutyl]-L-leucinamide N-(1-oxo-3-phenylpropyl)-L-leucine (56.5 mg., 0.2145 mmole, 1 eq.) and [βR-(βR*,γR*,δS*)]-δ-amino-N-butyl-β, γ-dihydroxycyclohexanepentanesulfonamide, monohydrochloride (80 mg., 0.2145 mmole, 1 eq., product of Example 1) were dissolved in dimethylformamide (1.1 ml., 0.2M). The reaction was cooled to 0° in an ice bath and 1-hydroxybenzotriazole hydrate (29 mg., 0.214 mmole, 1 eq.), triethylamine (45 μl., 0.32 mmole, 1.5 eq.) and ethyl-3-(3-dimethylamino)propyl carbodiimide hydrochloride (41.1 mg., 0.214 mmole, 1 eq.) were added. The reaction was warmed to room temperature overnight. To the reaction, pH4 buffer (6 ml., Mallinckrodt) was added. The reaction was stirred for 30 minutes, then extracted with ethyl acetate. The ethyl acetate extracts were combined, washed with saturated sodium bicarbonate solution (10 ml.) and saturated sodium chloride solution (10 ml.), dried (MgSO$_4$), filtered, and freed of solvent in vacuo to yield 124 mg. of crude product. This residue was purified by chromatography on silica gel (Merck, 13 g.) packed in chloroform eluting with acetone:chloroform (1:6 followed by 1:4). The product fractions were combined to yield 120 mg. of product. This was repurified by preparative HPLC using a fully capped C-18 column (YMC I - 15 100 A, ODS, 30×500 mm., 15μ spherical, 25 ml./minute, UV monitoring at 215 nm) eluting with 84% methanol in water containing 0.1% trifluoroacetic acid. The product fractions were combined, concentrated in vacuo, chased with toluene and dried in vacuo overnight to yield 77 mg. of white solid (1R*,2S*,3S*)-(1-oxo-3-phenylpropyl)-N-[4-[(butylamino)sulfonyl]-1 -(cyclohexylmethyl)-2,3-dihydroxybutyl]-L-leucinamide; m.p. 63°–73°; [α]$_D$=–53.6° (c=0.5, methanol). TLC (silica gel; chloroform:acetone, 2:1) R$_f$=0.60.

Anal. calc'd. for C$_{30}$H$_{51}$N$_3$O$_6$S . 3H$_2$O: C, 61.36; H, 8.86; N, 7.16; S, 5.46 Found: C, 61.45; H, 9.05; N, 6.86; S, 5.09.

EXAMPLE 41

(1R*,2S*,3S*)-[(Phenylmethoxy)carbonyl]-
N-[4-[(butylamino)sulfonyl]-1-(cyclohexylmethyl)-2,3
-dihydroxy-butyl]L-leucinamide N-[(Phenylmethoxy)carbonyl]-L-leucine (59.4 mg., 0.2238 mmole, 1 eq.) and [βR-(βR*,γR*,δS*)]-δ-amino-N-butyl-β,γ-dihydroxycyclohexanepentanesulfonamide, monohydrochloride (83.5 mg., 0.2238 mmole, 1 eq., product of Example 1) were dissolved in dimethylformamide (1.1 ml., 0.2M). The reaction was cooled to 0° in an ice bath and 1-hydroxybenzotriazole hydrate (30.2 mg., 0.2238, 1 eq.), triethylamine (47 μL, 0.336 mmoles, 1.5 eq.) and ethyl-3-(3-dimethylamino)propyl carbodiimide hydrochloride (49.2 mg., 0.2238 mmole, 1 eq.) were added. The reaction was warmed to room temperature overnight. To the reaction, pH$_4$ buffer (6 ml., Mallinckrodt) was added. The reaction was stirred for 30 minutes, then extracted with ethyl acetate. The ethyl acetate extracts were combined, washed with saturated sodium bicarbonate solution (10 ml.) and saturated sodium chloride solution (10 ml.), dried (MgSO$_4$), filtered and freed of solvent in vacuo to 123 mg. of an oil. The residue was purified by chromatography on silica gel (Merck, 12 g.) packed in chloroform and eluted with acetone:chloroform (1:6). The product fractions were combined to yield 118 mg. of material. This was rechromatographed on silica gel (Merck, 12 g.) packed in dichloromethane and eluted with 1°–2% methanol in dichloromethane. The product fractions were combined and concentrated in vacuo to yield 97 mg. of white solid (1R*,2S*,3S*)-[(phenylmethoxy)carbonyl]-N-[4-[(butylamino)sulfonyl]-1 -(cyclohexylmethyl)-2,3-dihydroxybutyl]-L-leucinamide; m.p. 50°–70°; [α]$_D$=–36° (c=0.5, methanol). TLC (silica gel; 4% methanol in dichloromethane) R$_f$=0.30.

Anal. calc'd. for C$_{29}$H$_{49}$N$_3$O$_7$S . 0.35 H$_2$O: C, 59.03; H, 8.49; N, 7.12; S, 5.43 Found: C, 59.36; H, 8.59; N, 7.01; S, 5.03.

EXAMPLE 42

(1R*,2S*,3S*)-N-[4-[(Butylamino)sulfonyl]-
1-(cyclohexylmethyl)-2,3
-dihydroxybutyl]-L-leucinamide The product from Example 41 (76 mg., 0.128 mmole, 1 eq.) was dissolved in a solution of methanol (2.6 ml., 0.05M), water (0.42 ml., 0.33M) and 1N HCl (0.13 ml., 0.13 mmole, 1 eq.) and treated with 20% palladium hydroxide on carbon catalyst (20 mg., 25% by weight, Aldrich). This was stirred under an atmosphere of hydrogen overnight. Upon completion, the reaction was diluted with methanol and filtered through regenerated cellulose to give 64 mg. of crude product. This residue was purified by chromatography on silica gel (Merck, 10 g.) packed in dichloromethane eluting with 3% methanol in dichloromethane and 0.2% NH$_4$OH. The product containing fractions were combined and concentrated in vacuo to yield 53.8 mg. of white solid (1R*,2S*,3S*)-N-[4-[(butylamino)sulfonyl]-1-(cyclohexylmethyl)-2,3 -dihydroxybutyl]-L-leucinamide; m.p. 99°–109°; [α]$_D$=–17.1° (c=0.6, methanol). TLC (silica gel; 8% methanol in dichloromethane+NH$_4$OH) R$_f$=0.39.

Anal. calc'd. for C$_{21}$H$_{43}$N$_3$O$_5$S: C, 56.09; H, 9.64; N, 9.35; S, 7.13 Found: C, 55.95; H, 9.92; N, 9.20; S, 6.83.

EXAMPLE 43

[1S-[1R*(R*),2S*,3S*]]-[2-[[(1,1-Dimethylethyl)
sulfonyl]methyl]-1-oxo-3
-phenylpropyl]-N-[4-[(butylamino)sulfonyl]-
1-(cyclohexylmethyl)-2,3-dihydroxybutyl]-L-leucinamide (S)-α-[[(1,1-Dimethylethyl)sulfonyl]methyl]benzenepropanoic acid [245 mg., 0.86 mmole, 1 eq., prepared as described in Example 5(a)], and (1R*,2S*,3S*)-N-[4-[(butylamino)sulfonyl]-1-(cyclohexylmethyl)-2,3-dihydroxybutyl]-L-leucinamide (387 mg., 0.86 mmole, product of Example 42) were dissolved in dimethylformamide (4.6 ml.). The mixture was cooled to 0° and treated with 1-hydroxybenzotriazole hydrate (116 mg., 0.86 mmole, 1 eq.) and ethyl-3-(3-dimethylamino)propyl carbodiimide hydrochloride (165 mg., 0.86 mmole, 1 eq.). The mixture was stirred at room temperature. After 6.5 hours, the reaction was cooled and triethylamine (60 μl., 0.43 mmole, 0.5 eq.) was added. After stirring overnight at room temperature, additional triethylamine (60 μl., 0.43 mmole, 0.5 eq.) was added and stirring at room temperature was continued for 2 hours. Aqueous buffer (pH4, 20 ml., Mallinckrodt) was added and the mixture was stirred for 20 minutes. The product was extracted into ethyl acetate (2×40 ml.), washed with saturated sodium bicarbonate solution (30 ml.) and saturated sodium chloride solution (30 ml.), dried (MgSO$_4$), and freed of solvent in vacuo. The remaining material was chromatographed on silica gel (60 g., Merck) eluting with 4% methanol in dichloromethane. It was then dissolved in benzene (30 ml.), filtered, and lyophilized to give 563 mg. of fluffy white solid [1S-[1R*(R*),2S*,3S*]]-[2-[[(1,1-dimethylethyl)sulfonyl]methyl]-1 -oxo-3-phenylpropyl]-N-[4-[(butylamino)sulfonyl]-1-(cyclohexylmethyl)-2, 3-dihydroxybutyl]-L-leucinamide; m.p. 87°–101°, [α]$_D$=–20.8° (c=0.6, methanol). TLC (silica gel; 4% methanol in dichloromethane) R$_f$=0.37.

Anal. calc'd. for C$_{35}$H$_{61}$N$_3$O$_8$S$_2$. 0.3H$_2$O: C, 58.27; H, 8.61; N, 5.82; S, 8.89 Found: C, 58.31; H, 9.01; N, 5.88; S, 8.72.

EXAMPLE 44

[βR-(βR*,γR*,δS*)]-N-Butyl-β,γ-dihydroxy-δ-
[(4-methylpentyl)
amino]cyclohexanepentanesulfonamide,
monoacetate salt Borane dimethylsulfide complex (10 molar, 0.9 ml., 9 mmole) was added dropwise to a tetrahydrofuran solution (3 ml.) of [1S-(1R*,2S*,3S*)]-N-[4-[(butylamino)sulfonyl]-1

-(cyclohexylmethyl)-2,3-dihydroxybutyl]-4-methylpentanamide (100 mg., 0.23 mmole, product of Example 38). The reaction mixture is stirred at 50° for one hour, quenched with 1N HCl (10 ml.), and after 30 minutes, saturated sodium bicarbonate was added (pH 8). The product was extracted with ethyl acetate (2×150 ml.) and this solution was washed with brine, dried ($Na_2SO_4$), filtered, and concentrated in vacuo. The resulting crude product was purified by chromatography through silica gel (20 g., Merck) using (2.5:0.1:100) methanol:acetic acid:chloroform. The appropriate fractions were combined and concentrated to yield 63 mg. of glassy, very hygroscopic white solid [βR-(βR*,γR*,δS*)]-N-butyl-β, γ-dihydroxy-δ-[(4-methylpentyl)amino] cyclohexanepentanesulfonamide, monoacetate salt; m.p. 68°–82°, $[\alpha]_D=+14°$ (c=0.5, methanol). TLC (silica gel, methanol:chloroform, 1:9) $R_f=0.46$.

Anal. Calc'd. for $C_{21}H_{44}N_2O_4S$ . $1.15H_2O$ . $0.9CH_3COOH$ C, 55.27; H, 10.15; N, 5.65; S, 6.47 Found: C, 55.27; H, 9.95; N, 6.05; S, 6.70.

EXAMPLE 45

(1R*,2S*,3S*)-[(2-Phenylethyl)sulfonyl]-N-[4-[(butylamino)sulfonyl]-1-(cyclohexylmethyl)-2,3-dihydroxybutyl]-L-histidinamide a) 3[(Phenylmethoxy)methyl]-L-histidine, dihydrochloride N-[(1,1-Dimethylethoxy)carbonyl]-3-[(phenylmethoxy)methyl]-L-histidine (1 g., 2.6 mmole) was cooled in an ice bath and treated with cold 4N HCl in dioxane (8 ml.). The reaction was stirred cold. After 3 hours, the reaction was concentrated in vacuo, chased with toluene, and dried to yield 1.21 g. of 3-[(phenylmethoxy)methyl]-L-histidine, dihydrochloride as a white foam.

b) [(2-Phenylethyl)sulfonyl]-3-[(phenylmethoxy)methyl]-L-histidine

3-[(Phenylmethoxy)methyl]-L-histidine (2.66 mmole, 1.0 eq.) was largely dissolved in a solution of sodium hydroxide (426 mg., 10.6 mmole, 4 eq.) in water (10 ml., 0.27M). After cooling in an ice bath, a solution of (2-phenylethyl)sulfonylchloride (545 mg., 2.66 mmole, 1 eq.) in ether (10 ml., 0.27M) was added. The reaction was stirred vigorously as 1N sodium hydroxide (2 ml.) was added to make the reaction basic. After 3 hours, additional (2-phenylethyl)sulfonylchloride (545 mg., 2.66 mmole, 1 eq.) was added. After stirring vigorously for 45 minutes, the layers were separated. The ether layer was reextracted with 1N sodium hydroxide (1×10 ml.). The aqueous layers were washed with ether, and adjusted to pH 6–7 with concentrated HCl. The solid precipitate was filtered off, and dried in vacuo to give 450 mg. of [(2-phenylethyl)sulfonyl]-3-[(phenylmethoxy)methyl]-L-histidine; m.p. 223°–233°.

c) (1R*,2S*,3S*)-[(2-Phenylethyl)sulfonyl]-N-[4-[(butylamino)sulfonyl]-1-(cyclohexylmethyl)-2,3-dihydroxybutyl]-3-[(phenylmethoxy)methyl]-L-histidinamide

[(2-Phenylethyl)sulfonyl]-3-[(phenylmethoxy)methyl]-L-histidine (196 mg., 0.44 mmole, 1 eq.) and [βR-(βR*,γR*,δS*)]-δ-amino-N-butyl-β,γ-dihydroxycyclohexanepentanesulfonamide, monohydrochloride (165 mg., 0.44 mmole, 1 eq., product of Example 1) were partially dissolved in dimethylformamide (4.4 ml., 0.1M). The reaction was cooled in an ice bath and 1-hydroxybenzotriazole hydrate (60 mg., 0.44 mmole, 1 eq.), ethyl-3-(3-dimethyl-amino) propyl carbodiimide monohydrochloride (84.5 mg., 0.44 mmole, 1 eq.) and triethylamine (93 μl., 0.66 mmole, 1.5 eq.) were added. The ice bath was removed, and the mixture was stirred overnight at room temperature. After an additional 4 hours, pH 4 buffer (20 ml., Mallinckrodt) was added and the reaction was stirred for 20 minutes. The reaction was extracted with ethyl acetate (2×40 ml.), dried ($MgSO_4$), filtered and freed of solvent in vacuo. The residue was purified by chromatography on silica gel (Merck, 30 g.) packed in dichloromethane, eluting with 2.5% methanol in dichloromethane plus 0.2% $NH_4OH$ to give 268 mg. of (1R*,2S*,3S*)-[(2-phenylethyl)sulfonyl]-N-[4-[(butylamino)sulfonyl]-1-(cyclohexylmethyl)-2,3-dihydroxybutyl]-3-[(phenylmethoxy)methyl]-L-histidinamide.

d) (1R*,2S*,3S*)-[(2-Phenylethyl)sulfonyl]-N-[4-[(butylamino)sulfonyl]-1-(cyclohexylmethyl)-2,3-dihydroxybutyl]-L-histidineamide The product from part (c) (314 mg., 0.412 mmole, 1 eq.) was dissolved in methanol (8.3 ml., 0.05M) and water (1.2 ml., 0.33M). While stirring at room temperature, 1N HCl (0.41 ml., 0.41 mmole, 1 eq.) and 20% palladium hydroxide on carbon (63 mg., 20 % by weight, Aldrich) were added. The mixture was stirred under an atmosphere of hydrogen for 24 hours. The reaction was diluted with methanol, filtered through a regenerated cellulose pad and washed with methanol. The material was purified by chromatography on silica gel (Merck, 20 g.) eluting with 3–5% methanol in dichloromethane containing 0.2% $NH_4OH$ to give 200 mg. of white solid (1R*,2S*,3S*)-[(2-phenylethyl)sulfonyl]-N-[4-(butylamino)sulfonyl]-1-(cyclohexylmethyl)-2,3-dihydroxybutyl]-L-histidinamide, m.p. 208°–210°; $[\alpha]_D=-30.3°$ (c=0.6, methanol). TLC (silica gel, 8% methanol in dichloromethane +0.2% $NH_4OH$) $R_f=0.35$.

Anal. calc'd. for $C_{29}H_{47}N_5O_7S_2$: C, 54.27; H, 7.38; N, 10.91; S, 9.99 Found: C, 54.26; H, 7.27; N, 10.66; S, 10.18.

EXAMPLES 46–63

Similarly, the following compounds were prepared:

[1S-(1R*, 2S*, 3R*)-N-[4-[(butylamino)sulfonyl]-1-(cyclohexylmethyl)-2,3-dihydroxybutyl]acetamide as a foam; $[\alpha]_D=-19.7°$ (c=0.6, methanol). TLC (silica gel, acetone:chloroform, 1:2) $R_f=0.19$ Anal calc'd. for $C_{17}H_{34}N_2O_5S$ . 0.25 $H_2O$: C, 53.31; H, 9.08; N, 7.31; S, 8.37 Found: C, 53.29; H, 9.24; N, 7.22; S, 8.26.

[1S-(1R*,2S*,3S*)-N-[4-[(butylamino)sulfonyl]-1-(cyclohexylmethyl)-2,3-dihydroxybutyl]acetamide as a white solid; m.p. 51°–54°; $[\alpha]_D=-15.4°$ (c=0.50, methanol). TLC (silica gel, chloroform: acetone, 4:1) $R_f=0.32$ Anal. calc'd. for $C_{17}H_{34}N_2O_5S$ . 0.8 $H_2O$: C, 51.96; H, 9.13; N, 7.13; S, 8.16 Found: C, 52.16; H, 8.75; N. 6.93; S, 7.77.

[1S-(1R,2S,3S*)]-(1-Oxo-3-phenylpropyl)-N-[4-[(butylamino)sulfonyl]-1-(cyclohexylmethyl)-2,3-dihydroxybutyl]-D-histidinamide, trifluoroacetate salt (1:1) as a solid lyophilizate; m.p. 70°–88° (dec.); $[\alpha]_D=-1.7°$ (c=0.6, methanol). TLC (silica gel, 10% methanol in dichloromethane plus 0.2% $NH_4OH$) $R_f=0.34$.

Anal. calc'd. for $C_{30}H_{47}N_5O_6S \cdot CF_3COOH$ C, 52.09; H, 6.83; N, 9.49; S, 4.35; F, 7.72 Found: C, 52.09; H, 6.50; N, 9.48; S, 4.11; F, 7.99.

(βR, γR,δS)-N-Butyl-δ-[[(1,1-dimethylethoxy)carbonyl]amino]-β,γ-dihydroxycyclohexanepentanesulfonamide as a tacky, semi-solid; $[α]_D=-21.8°$ (c=2.24, methanol). TLC (silica gel, dichloromethane: methanol, 20:1) $R_f=0.41$.

Anal. calc'd. for $C_{20}H_{40}N_2O_6S$: C, 55.02; H, 9.23; N, 6.42; S, 7.34 Found: C, 55.08; H, 9.48; N, 6.22; S, 7.20.

(βS, γR, δS)-N-Butyl-δ-[[(1,1-dimethylethoxy)carbonyl]amino]-β,γ-dihydroxycyclohexanepentanesulfonamide also as a tacky, semi-solid; $[α]_D=-15.1°$ (c=2.62, methanol) TLC (silica gel, dichloromethane:methanol, 20:1) $R_f=0.34$.

Anal. calc'd. for $C_{20}H_{40}N_2O_6S \cdot 0.5 H_2O$: C, 53.91; H, 9.27; N, 6.29; S, 7.19 Found: C, 54.08; H, 9.44; N, 5.97; S, 7.23.

(1S ,2R,3S )-N-[4-[(Butylamino)sulfonyl]-1-(cyclohexylmethyl)-2,3-dihydroxybutyl]-1 H-imidazole-4-propanamide as a white solid; m.p. 50°–90°; $[α]_D=-20°$ (c=0.3, methanol ). TLC (silica gel, chloroform:methanol:$NH_4OH$, 80:20:1) $R_f=0.2$.

Anal. calc'd. for $C_{21}H_{38}N_4O_5S \cdot 0.75 H_2O$: C, 53.42; H, 8.43; N, 11.87; S, 6.79 Found: C, 53.39; H, 8.23; N, 12.07; S, 6.47.

(1S, 2R,3R )-N-[4-[(Butylamino)sulfonyl]-1-(cyclohexylmethyl)-2,3 - dihydroxybutyl]-1 H-imidazole-4-propanamide as a white solid; m.p. 65°–90°; $[α]_D=-17°$ (c=0.6, methanol). TLC (silica gel, chloroform:methanol:$NH_4OH$, 80:20:1) $R_f=0.4$.

Anal. calc'd for $C_{21}H_{38}N_4O_5S$: C, 54.99; H, 8.35; N, 12.22; S, 6.99 Found: C, 54.75; H, 8.35; N, 12.31; S, 7.07.

(2S,3R,4S)-$N^2$-[(4-Amino-5-cyclohexyl-2,3-dihydroxypentyl)sulfonyl]-$N^2$ -butylglycinamide, monohydrochloride as a white solid lyophilizate m.p. 100°–125° (shrinking at 72°); $[α]_D=-1.9°$ (c=0.6, methanol). TLC (silica gel, 15% methanol in dichloromethane plus 0.2% $NH_4OH$) $R_f=0.19$.

Anal. calc'd. for $C_{17}H_{35}N_3O_5S \cdot HCl \cdot 0.9 H_2O$: C, 45.76; H, 8.54; N, 9.42; Cl, 7.95; S , 7.18 Found: C, 45.80; H, 8.63; N, 9.35; Cl, 8.05; 7.10.

(2R,3R,4S)-$N^2$-[(4-Amino-5-cyclohexyl-2,3-dihydroxypentyl)sulfonyl]-$N^2$ -butylglycinamide, monohydrochloride as a white solid; $[α]_D=-2.2°$ (c=0.5, methanol). TLC (silica gel; ethyl acetate:pyridine: acetic acid:water, 8:1:1:1) $R_f=0.36$.

Anal. calc'd. for $C_{17}H_{35}N_3O_5S \cdot HCl \cdot 0.7 H_2O$: C, 46.13; H, 8.52; N, 9.49; Cl, 8.01; S, 7.24 Found: C, 46.48; H, 8.31; N, 8.91; Cl, 7.83; S, 7.02.

(γR,δS)-δ-(Acetylamino)-N-butyl-β,γ-dihydroxy-α-methylcyclohexanepentanesulfonamide, isomer C as a solid lyophilizate; m.p. 53°–64° (shrinking at 42°); $[α]_D=-24.6°$ (c=0 5 methanol). TLC (silica gel, acetone:chloroform, 1:2) $R_f=0.44$.

Anal. calc'd. for $C_{18}H_{36}N_2O_5S$: C, 55.07; H, 9.24; N, 7.14; S, 8.17 Found: C, 55.12; H, 9.63; N, 7.08; S, 7.89.

[1R*(R*),2S*,3S*]-[2-[[(1,1-Dimethylethyl)sulfonyl]methyl]-1-oxo-3 -phenylpropyl]-N-[4-[(3-butenylamino)sulfonyl]-1-(cyclohexylmethyl)-2,3-dihydroxybutyl]-L-histidinamide, methanesulfonate salt (1:1) as a solid; m.p. 80°–121° (shrinking at 70°); $[α]_D=-3.2°$ (c=0.54, methanol). TLC (silica gel, dichloromethane:methanol:ammonia, 38:2:0.1) $R_f=0.09$.

Anal. calc'd. for $C_{35}H_{55}N_5O_8S_2 \cdot CH_4O_3S \cdot 1.5 H_2O$: C, 50.21; H, 7.26; N, 8.13; S, 11.17 Found: C, 50.21; H, 7.21; N, 7.99; S, 11.39.

[1S-(1R*,2S*,3R*)]-N-[4-[(Butylamino)sulfonyl]-1-(cyclohexylmethyl)-2,3 -dihydroxybutyl]-2-hydroxy-4-methylpentanamide as a white solid; m.p. 125°–140°; $[α]_D=-25.1°$ (c=0.45, methanol). TLC (silica gel, methanol:chloroform, 1:9) $R_f=0.5$.

Anal. calc'd. for $C_{21}H_{42}N_2O_6S \cdot 0.31 H_2O$: C, 55.28; H, 9.42; N, 6.14; S, 7.03 Found: C, 55.19; H, 9.52; N, 5.92; S, 6.78.

[N(S), γR, δS]-δ-Amino-β,γ-dihydroxy-N-[1-(hydroxymethyl)-2 -methylpropyl]cyclohexanepentanesulfonamide, isomer A, monohydrochloride as a white solid lyophilizate; m.p. 242°–247°; $[α]_D=+16.9°$ (c=0.45, methanol). TLC (silica gel, 15% methanol in dichloromethane plus $NH_4OH$) $R_f=0.24$.

Anal. calc'd. for $C_{16}H_{34}N_2O_5S \cdot HCl \cdot 0.4 H_2O$: C, 46.85; H, 8.80; N, 6.83; S, 7.82; Cl, 8.64 Found: C, 46.80; H, 8.94; N, 6.78; S, 7.88; Cl, 8.63.

[N(S),γR,δS]-δ-Amino-β,γ-dihydroxy-N-[1-(hydroxymethyl)-2-methylpropyl]cyclohexanepentanesulfonamide, isomer B, monohydrochloride as a white solid lyophilizate; m.p. 142°–147°; $[α]_D=+6.4°$ (c=0.5, methanol). TLC (silica gel, 20% methanol in dichloromethane plus $NH_4OH$) $R_f=0.32$.

Anal. calc'd. for $C_{16}H_{34}N_2O_5S \cdot HCl \cdot 0.8 H_2O \cdot 0.6 NH_4Cl$: C, 42.75; H, 8.75; N, 8.10; S, 7.13; Cl, 12.62 Found: C, 42.89; H, 8.57; N, 7.77; S, 6.93; Cl, 12.50.

[βR- (βR*, γR*, δS*)]-N-Butyl-β,γ-dihydroxy-δ-[(3-pyridinylmethyl)amino]cyclohexanepentanesulfonamide, dihydrochloride as a white solid lyophilizate; m.p. 100°–106° (shrinking at 80°); $[α]_D=+17.6°$ (c=0.5, methanol). TLC (silica gel, 10% methanol in dichloromethane plus $NH_4OH$) $R_f=0.44$.

Anal. calc'd. for $C_{21}H_{37}N_3O_4S \cdot 2 HCl \cdot 0.5 H_2O$: C, 49.50; H, 7.91; N, 8.25; S, 6. 29; Cl, 13.92 Found: C, 49.56; H, 8.25; N, 8.02; S, 6. 37; Cl, 14.11.

[βS-(βR*,γS*,δR*)]-δ-Amino-N-(4-hydroxybutyl)-β,γ-dihydroxycyclohexanepentanesulfonamide, monoacetate salt as a white lyophilizate; m.p. 51°–53°; $[α]_D=-13.6°$ (c=1.0, methanol). TLC (silica gel, ethyl acetate:pyridine:acetic acid: water, 9:1:1:1) $R_f=0.20$.

Anal. calc'd. for $C_{15}H_{32}N_2O_5S \cdot CH_3COOH \cdot 0.7 H_2O$: C, 48.03; H, 8.87; N, 6.59; S, 7.54 Found: C, 47.98; H, 8.86; N, 6.45; S, 7.49.

[βS-(βR*,γS*,δR*)]-N-Butyl-β,γ-dihydroxy-δ-[(4-methylpentyl)amino]cyclohexanepentanesulfonamide, monohydrochloride as a white solid; m.p 64°–80°; $[α]_D=+7.2°$ (c=0.32, methanol). TLC (silica gel, methanol:chloroform, 1:9) $R_f=0 52$.

Anal. calc'd. for $C_{21}H_{44}N_2O_4S \cdot HCl \cdot 1.1 H_2O$: C, 52.89; H, 9.98; N, 5.87; S, 6.72; Cl, 7.43 Found: C, 53.20; H, 9.63; N, 5.72; S, 6.26; Cl, 7.57.

[βS-(βR*,γS*,δR*)]-N-Butyl-β,γ-dihydroxy-δ-[(2-hydroxy-4 -methylpentyl)amino]cyclohexanepentane-sulfonamide, monoacetate salt as a white solid; m.p. 47°–60°; $[α]_D=+12.0°$ (c=0.3, methanol). TLC (silica gel, methanol:chloroform:acetic acid, 15:85:0.2) $R_f=0.46$.

Anal. calc'd. for $C_{21}H_{44}N_2O_5S \cdot CH_3COOH \cdot 1.75 H_2O$: C, 52.30; H, 9.83; N, 5.31; S, 6.07 Found: C, 52.27; H, 9.60; N, 5.58; S, 5.69.

EXAMPLES 64–88

The following are additional compounds within the scope of this invention represented by the formula:

$$W_2-CH_2-CH-\overset{\overset{O}{\|}}{C}-\underset{\underset{R_{15}}{|}}{N}-CH-Y-NH-CH-CH-CH-CH-Z-N\underset{R_2}{\overset{R_1}{<}}$$

with $R_{14}$ above CH, $R_{13}$ above CH, $R_7$ above CH, OH below CH, OH below CH, $R_3$ above CH.

| | | | |
|---|---|---|---|
| EXAMPLE | 64 | 65 | 66 |
| $W_2$ | $(H_3C)_3-C-SO_2-$ | $(H_3C)_3-C-SO_2-$ | $(H_3C)_3-C-SO_2-$ |
| $R_{14}$ | C₆H₅–CH₂– | C₆H₅–CH₂– | C₆H₅–CH₂– |
| $R_{15}$ | H | H | H |
| $R_{13}$ | –CH₂–(imidazolyl) | –CH₂–(imidazolyl) | –CH₂–(imidazolyl) |
| Y | CO | CH₂ | CO |
| $R_7$ | cyclohexyl-CH₂– | cyclohexyl-CH₂– | cyclohexyl-CH₂– |
| $R_3$ | H | H | H |
| Z | SO | $SO_2$ | $SO_2$ |
| $R_1$ | $-(CH_2)_3-CH_3$ | $-(CH_2)_3CH_3$ | $-CH_2-\overset{\overset{O}{\|}}{C}-N(H)(CH_3)$ |
| $R_2$ | H | H | H |
| EXAMPLE | 67 | 68 | 69 |
| $W_2$ | $(H_3C)_3-C-SO_2-$ | $(H_3C)_3-C-SO_2-$ | $(H_3C)_3-C-SO_2-$ |
| $R_{14}$ | C₆H₅–CH₂– | C₆H₅–CH₂– | C₆H₅–CH₂– |
| $R_{15}$ | H | H | H |
| $R_{13}$ | –CH₂–(imidazolyl) | –CH₂–(imidazolyl) | –CH₂–(imidazolyl) |
| Y | CO | CO | CO |
| $R_7$ | cyclohexyl-CH₂– | cyclohexyl-CH₂– | cyclohexyl-CH₂– |
| $R_3$ | H | H | H |
| Z | $SO_2$ | $SO_2$ | $SO_2$ |
| $R_1$ | $-CH_2-C(=O)-OH$ | $-(CH_2)_6-NH_2$ | $-(CH_2)_6-COOH$ |
| $R_2$ | H | H | H |
| EXAMPLE | 70 | 71 | 72 |
| $W_2$ | $(H_3C)_3-C-SO_2-$ | $(H_3C)_3-C-SO_2-$ | $(H_3C)_3-C-SO_2$ |

-continued $$W_2-CH_2-CH(R_{14})-C(=O)-N(R_{15})-CH(R_{13})-Y-NH-CH(R_7)-CH(OH)-CH(OH)-CH(R_3)-Z-N(R_1)(R_2)$$

| | | | |
|---|---|---|---|
| $R_{14}$ | C₆H₅–CH₂– | C₆H₅–CH₂– | C₆H₅–CH₂– |
| $R_{15}$ | H | H | H |
| $R_{13}$ | –CH₂–(imidazolyl, NH) | –CH₂–(thiazolyl) | –(CH₂)₃–CH₃ |
| Y | CO | CO | CO |
| $R_7$ | C₆H₅–CH₂– | C₆H₁₁–CH₂– | C₆H₁₁–CH₂– |
| $R_3$ | H | H | H |
| Z | SO₂ | SO₂ | SO₂ |
| $R_1$ | –(CH₂)₃–CH₃ | –(CH₂)₃–CH₃ | –(CH₂)₃–CH₃ |
| $R_2$ | H | H | H |
| EXAMPLE | 73 | 74 | 75 |
| $W_2$ | (H₃C)₃–C–SO₂– | (H₃C)₃–C–SO₂– | (H₃C)₃–C–SO₂– |
| $R_{14}$ | C₆H₅–CH₂– | C₆H₅–CH₂– | H₃C–(H₂C)₃– |
| $R_{15}$ | H | –CH₃ | H |
| $R_{13}$ | –CH₂–S–CH₃ | –CH₂–(imidazolyl, NH) | –CH₂–(imidazolyl, NH) |
| Y | CH₂ | CO | CO |
| $R_7$ | C₆H₁₁–CH₂– | C₆H₁₁–CH₂– | C₆H₁₁–CH₂– |
| $R_3$ | H | H | H |
| Z | SO₂ | SO₂ | SO₂ |
| $R_1$ | –(CH₂)₃–CH₃ | –(CH₂)₃–CH₃ | –(CH₂)₃–CH₃ |
| $R_2$ | H | H | H |
| EXAMPLE | 76 | 77 | 78 |
| $W_2$ | (H₃C)₃–C–SO₂– | (H₃C)₃–C–SO₂– | (H₃C)₃–C–SO₂– |
| $R_{14}$ | (3-pyridyl)–CH₂– | H₃CO–C₆H₄–CH₂– | H₃CO–C₆H₄–CH₂– |
| $R_{15}$ | H | H | –CH₃ |
| $R_{13}$ | –CH₂–(imidazolyl, NH) | –CH₂–(imidazolyl, NH) | –CH₂–(imidazolyl, NH) |
| Y | CO | CO | CO |

-continued

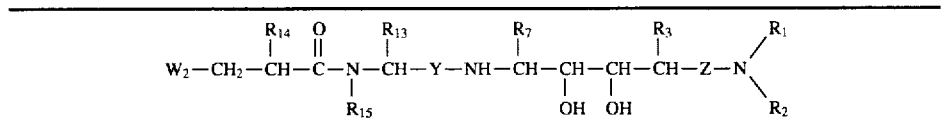

| | | | |
|---|---|---|---|
| R$_7$ |  cyclohexyl-CH$_2$— | cyclohexyl-CH$_2$— | cyclohexyl-CH$_2$— |
| R$_3$ | H | H | H |
| Z | SO$_2$ | SO$_2$ | SO$_2$ |
| R$_1$ | —(CH$_2$)$_3$—CH$_3$ | —(CH$_2$)$_3$—CH$_3$ | —(CH$_2$)$_3$—CH$_3$ |
| R$_2$ | H | H | H |
| EXAMPLE | 79 | 80 | 81 |
| W$_2$ | 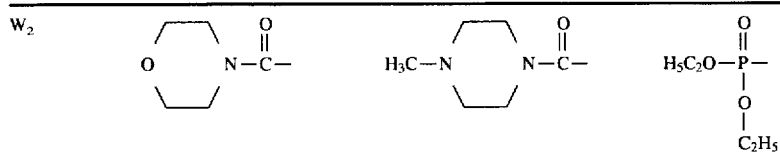 morpholine-N-C(O)— | H$_3$C—N-piperazine-N-C(O)— | H$_5$C$_2$O—P(O)(OC$_2$H$_5$)— |
| R$_{14}$ | phenyl-CH$_2$— | phenyl-CH$_2$— | phenyl-CH$_2$— |
| R$_{15}$ | H | H | H |
| R$_{13}$ | —CH$_2$-imidazolyl | —CH$_2$-imidazolyl | —CH$_2$-imidazolyl |
| Y | CO | CO | CO |
| R$_7$ | cyclohexyl-CH$_2$— | cyclohexyl-CH$_2$— | cyclohexyl-CH$_2$— |
| R$_3$ | H | H | H |
| Z | SO$_2$ | SO$_2$ | SO$_2$ |
| R$_1$ | —(CH$_2$)$_3$—CH$_3$ | —(CH$_2$)$_3$—CH$_3$ | —(CH$_2$)$_3$—CH$_3$ |
| R$_2$ | H | H | H |
| EXAMPLE | 82 | 83 | 84 |
| W$_2$ | HS— | phenyl-CH$_2$-C(O)— | (H$_3$C)$_2$—N—C(O)— |
| R$_{14}$ | phenyl-CH$_2$— | phenyl-(CH$_2$)$_2$— | phenyl-CH$_2$— |
| R$_{15}$ | H | H | H |
| R$_{13}$ | —CH$_2$-imidazolyl | —CH$_2$-imidazolyl | —CH$_2$-imidazolyl |
| Y | CO | CO | CO |
| R$_7$ | cyclohexyl-CH$_2$— | cyclohexyl-CH$_2$— | cyclohexyl-CH$_2$— |
| R$_3$ | H | H | H |
| Z | SO$_2$ | SO$_2$ | SO$_2$ |
| R$_1$ | —(CH$_2$)$_3$—CH$_3$ | —(CH$_2$)$_4$—CH$_3$ | —(CH$_2$)$_2$—CH$_3$ |

-continued $$W_2-CH_2-\underset{R_{14}}{\underset{|}{CH}}-\underset{}{\overset{O}{\underset{||}{C}}}-\underset{R_{15}}{\underset{|}{N}}-CH-Y-NH-\underset{R_7}{\underset{|}{CH}}-\underset{OH}{\underset{|}{CH}}-\underset{OH}{\underset{|}{CH}}-\underset{R_3}{\underset{|}{CH}}-Z-N\underset{R_2}{\overset{R_1}{\diagdown}}$$

| | | | |
|---|---|---|---|
| $R_2$ | H | H | H |
| EXAMPLE | 85 | 86 | 87 |
| $W_2$ | $H_3C-(H_2C)_3-\underset{H}{\underset{|}{N}}-SO_2-$ | ⌬—$CH_2-S-$ | $H_3C-\overset{O}{\underset{||}{C}}-S-$ |
| $R_{14}$ | ⌬—$CH_2-$ | ⌬—$CH_2-$ | ⌬—$CH_2-$ |
| $R_{15}$ | H | H | H |
| $R_{13}$ | $-CH_2-$[imidazole] | $-CH_2-$[imidazole] | $-CH_2-$[imidazole] |
| Y | CO | $CH_2$ | CO |
| $R_7$ | ⌬—$CH_2-$ (cyclohexyl) | ⌬—$CH_2-$ (cyclohexyl) | ⌬—$CH_2-$ (cyclohexyl) |
| $R_3$ | H | H | H |
| Z | SO | $SO_2$ | $SO_2$ |
| $R_1$ | $-(CH_2)_3-CH_3$ | $-C_2H_5$ | $-(CH_2)_3-CH_3$ |
| $R_2$ | H | H | H |

EXAMPLES 88–96

The following are additional compounds within the scope of this invention represented by the formula:

$$W_1-\underset{R_{16}}{\underset{|}{N}}-\underset{R_{14}}{\underset{|}{CH}}-\overset{O}{\underset{||}{C}}-\underset{R_{15}}{\underset{|}{N}}-\underset{R_{13}}{\underset{|}{CH}}-Y-NH-\underset{R_7}{\underset{|}{CH}}-\underset{OH}{\underset{|}{CH}}-\underset{OH}{\underset{|}{CH}}-\underset{R_3}{\underset{|}{CH}}-SO_2-N\underset{R_2}{\overset{R_1}{\diagdown}}$$

| | | | |
|---|---|---|---|
| EXAMPLE | 88 | 89 | 90 |
| $W_1$ | $(H_3C)_2-HC-SO_2-$ | $H_5C_2-O-\overset{O}{\underset{||}{C}}-$ | $H_5C_2-O-\overset{O}{\underset{||}{C}}-$ |
| $R_{16}$ | H | H | $H_3C-$ |
| $R_{14}$ | ⌬—$CH_2-$ | ⌬—$CH_2-$ | ⌬—$CH_2-$ |
| $R_{15}$ | H | H | H |
| $R_{13}$ | $-CH_2-$[imidazole] | $-CH_2-$[imidazole] | $-CH_2-$[imidazole] |
| Y | CO | CO | CO |

-continued
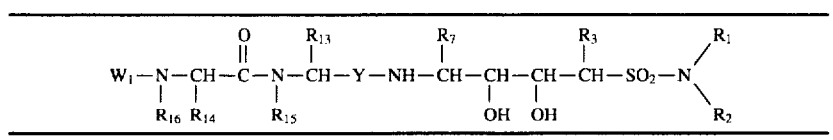
| | | | |
|---|---|---|---|
| $R_7$ | 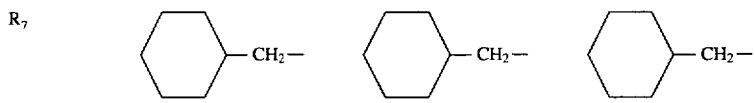 | | |
| $R_3$ | H | H | H |
| $R_1$ | $-(CH_2)_3-CH_3$ | $-(CH_2)_3-CH_3$ | $-(CH_2)_3-CH_3$ |
| $R_2$ | H | H | H |
| EXAMPLE | 91 | 92 | 93 |
| $W_1$ | 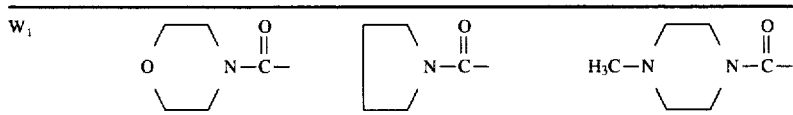 | | |
| $R_{16}$ | H | H | H |
| $R_{14}$ |  | | |
| $R_{15}$ | H | $-CH_3$ | H |
| $R_{13}$ | 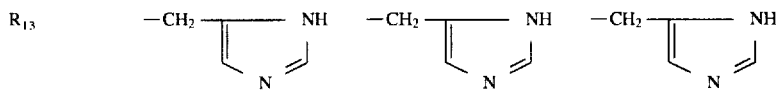 | | |
| Y | CO | CO | CO |
| $R_7$ | 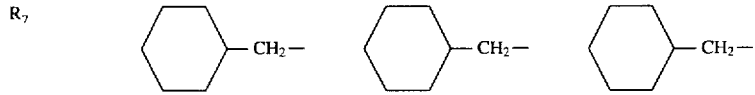 | | |
| $R_3$ | H | H | H |
| $R_1$ | $-(CH_2)_3-CH_3$ | $-(CH_2)_3-CH_3$ | $-(CH_2)_3-CH_3$ |
| $R_2$ | H | H | H |
| EXAMPLE | 94 | 95 | 96 |
| $W_1$ | 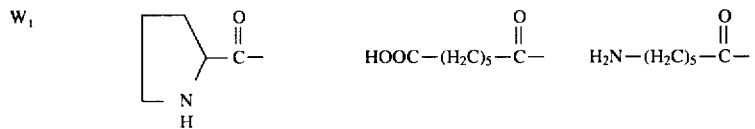 | $HOOC-(H_2C)_5-\overset{O}{\underset{\|}{C}}-$ | $H_2N-(H_2C)_5-\overset{O}{\underset{\|}{C}}-$ |
| $R_{16}$ | H | H | H |
| $R_{14}$ |  | | |
| $R_{15}$ | H | H | H |
| $R_{13}$ | 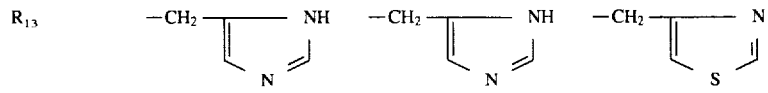 | | |
| Y | CO | CO | CO |
| $R_7$ | 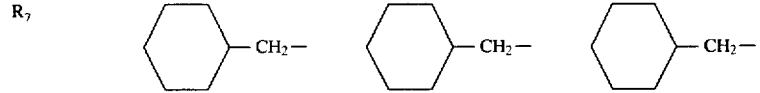 | | |
| $R_3$ | H | H | H |

-continued

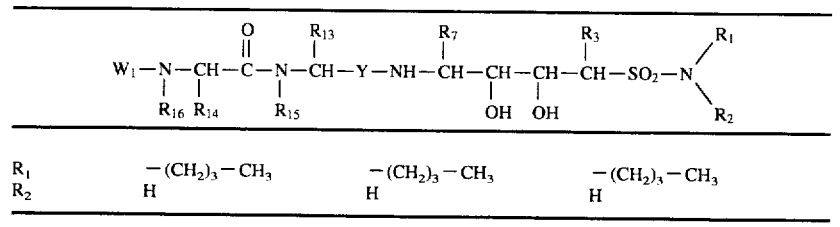

| R₁ | $-(CH_2)_3-CH_3$ | $-(CH_2)_3-CH_3$ | $-(CH_2)_3-CH_3$ |
|----|---|---|---|
| R₂ | H | H | H |

EXAMPLES 97–101

The following are additional compounds within the scope of this invention represented by the formula:

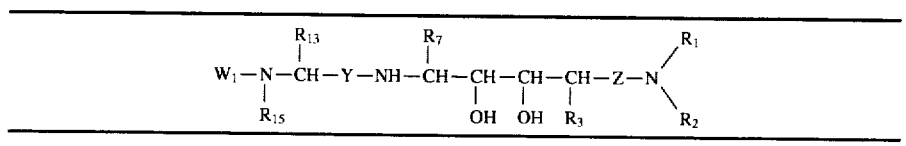

| EXAMPLE | 97 | 98 | 99 |
|---|---|---|---|
| W₁ | benzimidazol-2-yl-C(O)– | (C₆H₅–CH₂)₂–CH–C(O)– | C₆H₅–(CH₂)₂– |
| R₁₅ | H | H | –CH₃ |
| R₁₃ | –CH₂–(imidazol-4-yl)NH | –CH₂–(imidazol-4-yl)NH | –CH₂–(imidazol-4-yl)NH |
| Y | CO | CO | CO |
| R₇ | cyclohexyl–CH₂– | cyclohexyl–CH₂– | cyclohexyl–CH₂– |
| R₃ | H | H | H |
| Z | SO₂ | SO₂ | SO |
| R₁ | $-(CH_2)_3-CH_3$ | $-(CH_2)_3-CH_3$ | $-(CH_2)_3-CH_3$ |
| R₂ | H | H | H |

| EXAMPLE | 100 | 101 |
|---|---|---|
| W₁ | $(H_3C)_3-C-SO_2-$ | C₆H₅–CH₂–HN–SO₂– |
| R₁₅ | H | H |
| R₁₃ | –CH₂–(imidazol-4-yl)NH | –CH₂–(imidazol-4-yl)NH |
| Y | CH₂ | CO |
| R₇ | cyclohexyl–CH₂– | cyclohexyl–CH₂– |
| R₃ | H | –CH₃ |
| Z | SO₂ | SO₂ |
| R₁ | $-(CH_2)_3-CH_3$ | $-(CH_2)_3-CH_3$ |
| R₂ | H | H |

EXAMPLES 102–109

The following are additional compounds within the scope of this invention represented by the formula $$X-NH-\underset{\underset{R_7}{|}}{CH}-\underset{\underset{OH}{|}}{CH}-\underset{\underset{OH}{|}}{CH}-\underset{\underset{R_3}{|}}{CH}-Z-N\diagup\!\!\!\diagdown_{R_2}^{R_1}$$

| EXAMPLE | 102 | 103 | 104 |
|---|---|---|---|
| X | $H_3C-\underset{\underset{H}{|}}{N}-\underset{\underset{||}{O}}{C}-\underset{\underset{CH_3}{|}}{CH}-$ | pyridin-3-yl-$CH_2-$ | H |
| $R_7$ | cyclohexyl-$CH_2-$ | cyclohexyl-$CH_2-$ | cyclohexyl-$CH_2-$ |
| $R_3$ | H | $-CH_3$ | H |
| Z | $SO_2$ | $SO_2$ | $SO_2$ |
| $R_1$ | $-(CH_2)_3-CH_3$ | $-(CH_2)_3-CH_3$ | $-CH_2-$cyclohexyl |
| $R_2$ | H | H | H |

| EXAMPLE | 105 | 106 | 107 |
|---|---|---|---|
| X | H | H | $(H_3C)_2-CH-\underset{\underset{OH}{|}}{CH}-CH_2-$ |
| $R_7$ | cyclohexyl-$CH_2-$ | cyclopentyl-$CH_2-$ | cyclohexyl-$CH_2-$ |
| $R_3$ | H | H | H |
| Z | $SO_2$ | $SO_2$ | $SO_2$ |
| $R_1$ | $-(CH_2)_3-CH_3$ | $-(CH_2)_3-CH_3$ | $-(CH_2)_3-CH_3$ |
| $R_2$ | $-CH_2-\underset{\underset{||}{O}}{C}-NH_2$ | H | H |

| EXAMPLE | 108 | 109 |
|---|---|---|
| X | (1H-imidazol-4-yl)-$CH_2CH(OH)-CH_2-$ | (1H-imidazol-4-yl)-$CH(OH)-CH_2-CH_2-$ |
| $R_7$ | cyclohexyl-$CH_2-$ | cyclohexyl-$CH_2-$ |
| $R_3$ | H | H |
| Z | $SO_2$ | $SO_2$ |
| $R_1$ | $-(CH_2)_3-CH_3$ | $-(CH_2)_3-CH_3$ |
| $R_2$ | H | H |

EXAMPLE 110

1000 tablets each containing the following ingredients:

| | |
|---|---|
| [βR-(βR*,γR*,δS*)]-δ-Amino-N-butyl-β,γ-dihydroxycyclohexanepentanesulfonamide, monohydrochloride | 250 mg. |
| Cornstarch | 100 mg. |

77

-continued

| | |
|---|---|
| Gelatin | 20 mg. |
| Avicel (microcrystalline cellulose) | 50 mg. |
| Magnesium stearate | 5 mg. |
| | 425 mg. | are prepared from sufficient bulk quantities by mixing the active monohydrochloride salt compound of Example 1 and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 250 mg. of active ingredient.

In a similar manner, tablets containing 250 mg. of the product of any of Examples 2 to 109 can be prepared.

A similar procedure can be employed to form tablets containing 500 mg. of active ingredient.

EXAMPLE 11

An injectable solution is prepared as follows:

| | |
|---|---|
| [1S-[1R*(R*),2S*,3S*]]-[2-[[(1,1-Dimethylethyl)sulfonyl]-methyl]-1-oxo-3-phenylpropyl]-N-[4-[(butylamino)sulfonyl]-1-(cyclo-hexylmethyl)-2,3-dihydroxybutyl]-L-histidinamide, methanesulfonate (1:1) salt | 1000 g. |
| Methyl paraben | 5 g. |
| Propyl paraben | 1 g. |
| Sodium chloride | 5 g. |

The active substance, preservatives, and sodium chloride are dissolved in 3 liters of water and then the volume is brought up to 5 liters. The solution is filtered through a sterile filter and aseptically filled into presterilized vials which are closed with presterilized rubber closures. Each vial contains 5 ml. of solution in a concentration of 200 mg. of active ingredient per ml. of solution for injection.

In a similar manner, an injectable solution containing 200 mg. of active ingredient per ml. of solution can be prepared for the product of any of Examples 1 to 4 and 6 to 109.

EXAMPLE 112

1000 tablets each containing the following ingredients:

| | |
|---|---|
| (γR,δS)-δ-Amino-N-butyl-β,γ-dihydroxy-α-methylcyclohexane-pentanesulfonamide, isomer C, monohydrochloride | 500 mg. |
| Avicel | 300 mg. |
| Hydrochlorothiazide | 14.5 mg. |
| Lactose | 113 mg. |
| Cornstarch | 15.5 mg. |
| Stearic acid | 7 mg. |
| | 950 mg. | are prepared from sufficient bulk quantities by slugging the (γR,δS)-δ-amino-N-butyl-δ,γ-dihydroxy-α-methylcyclo-hexanepentanesulfonamide, isomer C, monohydrochloride, Avicel, and a portion of the stearic acid. The slugs are ground and passed through a #2 screen, then mixed with the hydrochlorothiazide, lactose, cornstarch, and remainder of the stearic acid. The mixture is compressed into 950 mg. capsule shaped tablets in a tablet press. The tablets are scored for dividing in half.

78

In a similar manner, tablets can be prepared containing 500 mg. of the product of any of Examples 1 to 21 and 23 to 109.

What is claimed is:

1. A compound of the formula:

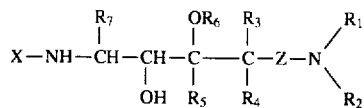

or a pharmaceutically acceptable salt thereof wherein:

Z is SO or $SO_2$;

$R_1$ and $R_2$ are independently selected from the group consisting of hydrogen, alkyl of 1 to 7 carbons, alkenyl or 2 to 7 carbons, $—(CH_2)_m$-aryl, $—(CH_2)_m$-cycloalkyl, $—(CH_2)_m$-heterocyclo, halo substituted alkyl of 1 to 7 carbons, $—(CH_2)_g—O—R_{15}$, $—(CH_2)_g—S—R_{15}$,

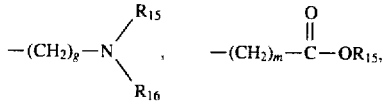

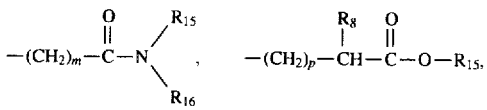

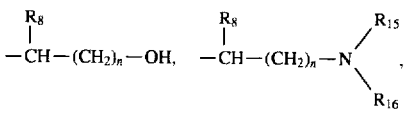

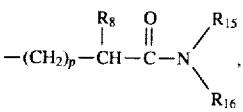

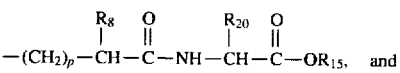

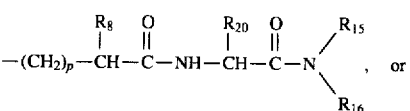

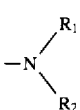

is a heterocyclic ring

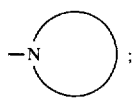

$R_3$, $R_7$, $R_8$, $R_{14}$ and $R_{20}$ are independently selected from the group consisting of hydrogen, alkyl of 1 to 7 carbons, halo substituted alkyl of 1 to 7 carbons, $—(CH_2)_m$-aryl, $—(CH_2)_m$-heterocyclo, $—(CH_2)_m$-cycloalkyl, $—(CH_2)_n—O—R_{15}$, $—(CH_2)_n—S—R_{15}$,

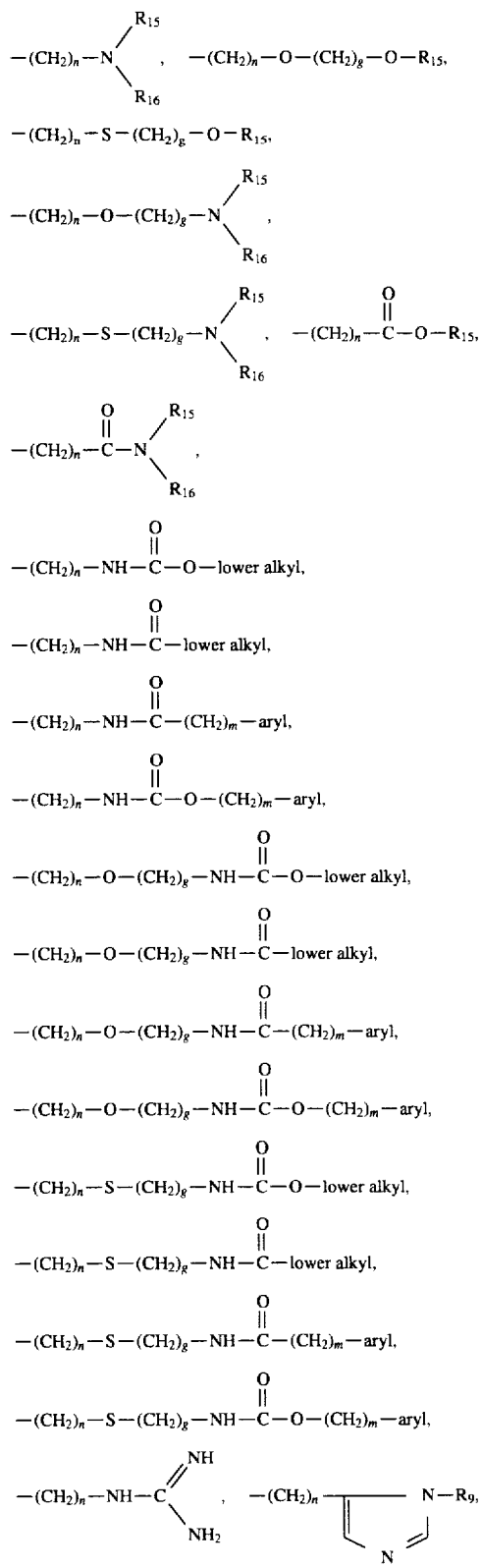
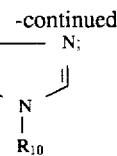
$R_4$ is hydrogen or alkyl of 1 to 7 carbons;
$R_5$ and $R_6$ are independently selected from the group consisting of hydrogen, alkyl of 1 to 7 carbons, halo substituted alkyl of 1 to 7 carbons, —$(CH_2)_m$-aryl, —$(CH_2)_m$-heterocyclo, and —$(CH_2)_m$-cycloalkyl;
$R_9$ is
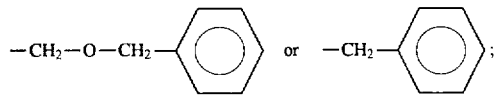
$R_{10}$ is
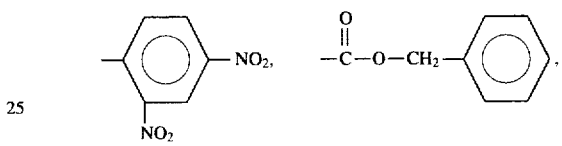
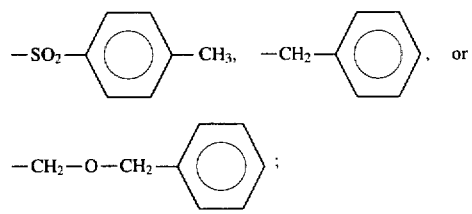
X is hydrogen,
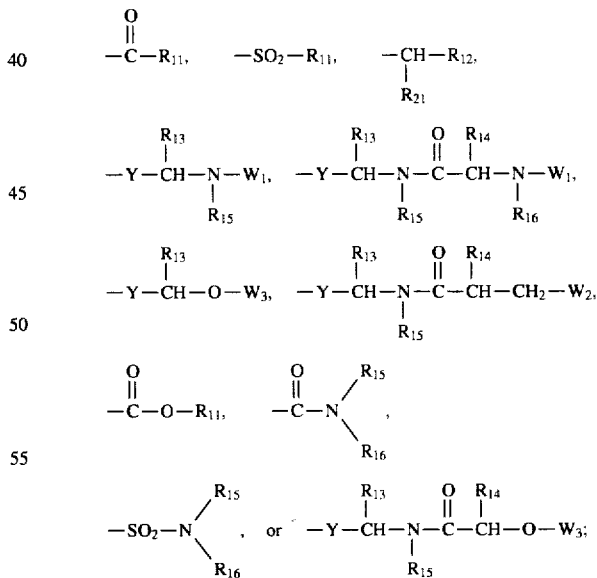
Y is —$CH_2$— or

$R_{11}$ is alkyl of 1 to 7 carbons, hydroxy substituted alkyl of 1 to 7 carbons, aryl, heterocyclo, cycloalkyl, -alkylene-aryl, -alkylene-heterocyclo, -alkylene-cycloalkyl,

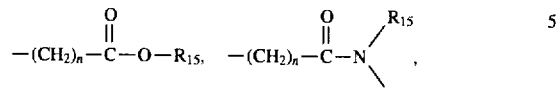

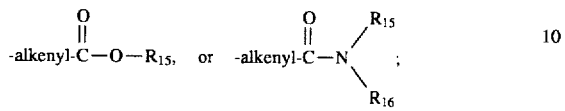

$R_{12}$ and $R_{21}$ are independently selected from the group consisting of hydrogen, alkyl of 1 to 7 carbons, hydroxy substituted alkyl of 1 to 7 carbons, aryl, heterocyclo, cycloalkyl, -alkylene-aryl, -alkylene-heterocyclo, -alkylene-cycloalkyl,

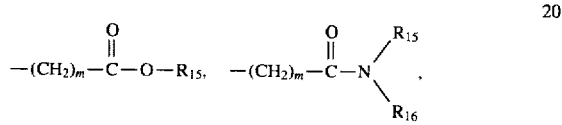

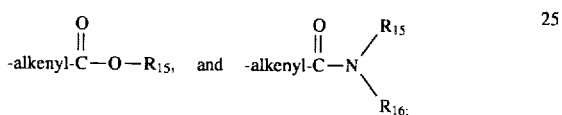

$R_{13}$ is selected from the group consisting of hydrogen, alkyl of 1 to 7 carbons, halo substituted alkyl of 1 to 7 carbons, —$(CH_2)_m$-aryl, —$(CH_2)$—cycloalkyl, —$(CH_2)_n$—O—$R_{15}$, —$(CH_2)_n$—S—$R_{15}$, —$(CH_2)_n$—O—$(CH_2)_g$—O—$R_{15}$,

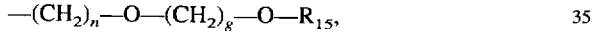

—$(CH_2)_n$—S—$(CH_2)_g$—O—$R_{15}$,

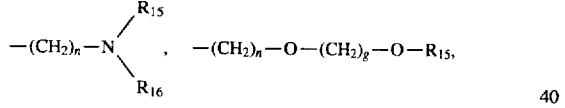

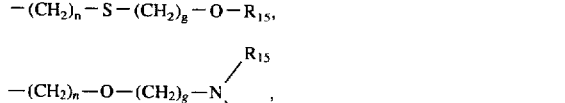

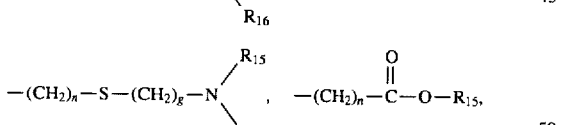

—$(CH_2)_n$—NH—C(=O)—O-lower alkyl,

—$(CH_2)_n$—NH—C(=O)-lower alkyl,

—$(CH_2)_n$—NH—C(=O)—$(CH_2)_m$-aryl,

—$(CH_2)_n$—NH—C(=O)—O—$(CH_2)_m$-aryl,

—$(CH_2)_n$—O—$(CH_2)_g$—NH—C(=O)—O-lower alkyl,

—$(CH_2)_n$—O—$(CH_2)_g$—NH—C(=O)-lower alkyl,

—$(CH_2)_n$—O—$(CH_2)_g$—NH—C(=O)—$(CH_2)_m$-aryl,

—$(CH_2)_n$—O—$(CH_2)_g$—NH—C(=O)—O—$(CH_2)_m$-aryl,

—$(CH_2)_n$—S—$(CH_2)_g$—NH—C(=O)—O-lower alkyl,

—$(CH_2)_n$—S—$(CH_2)_g$—NH—C(=O)-lower alkyl,

—$(CH_2)_n$—S—$(CH_2)_g$—NH—C(=O)—$(CH_2)_m$-aryl,

—$(CH_2)_n$—S—$(CH_2)_g$—NH—C(=O)—O—$(CH_2)_m$-aryl,

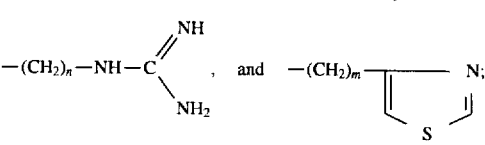

$R_{15}$ and $R_{16}$ are independently selected from the group consisting of hydrogen, alkyl of 1 to 7 carbons, —$(CH_2)_m$—cycloalkyl, —$(CH_2)_m$-aryl, and —$(CH_2)_m$-heterocyclo;

$W_1$ is hydrogen,

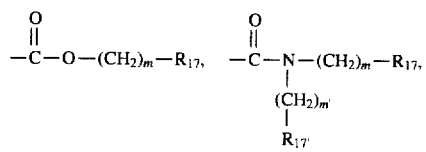

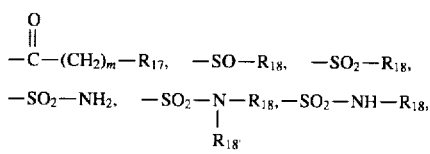

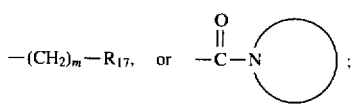

$R_{17}$ and $R_{17'}$ are independently selected from the group consisting of hydrogen, alkyl of 1 to 7 carbons, aryl, heterocyclo, and cycloalkyl;

$W_2$ is hydrogen, —$R_{18}$,

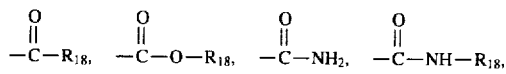

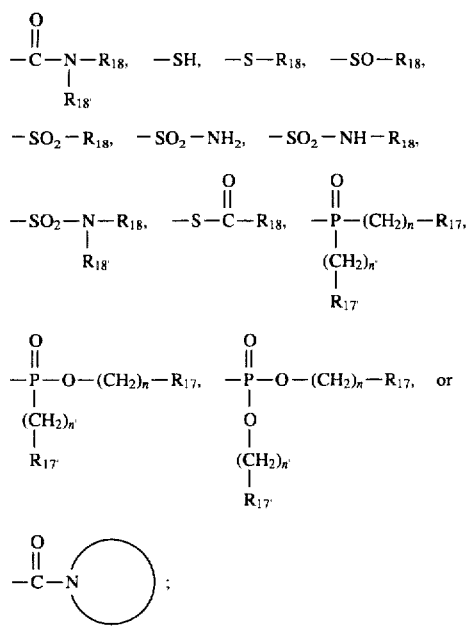

W₃ is hydrogen, —R₁₈,

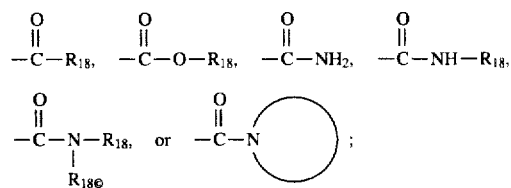

R₁₈ and R₁₈' are independently selected from the group consisting of alkyl of 1 to 7 carbons, —(CH₂)ₘ-aryl, —(CH₂)ₘ-cycloalkyl, —(CH₂)ₘ-heterocyclo,

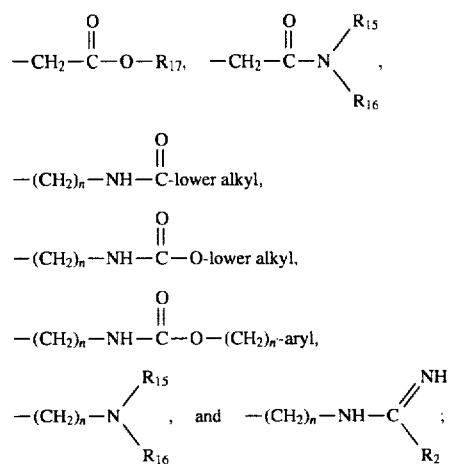

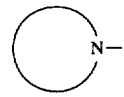

represents a heterocyclic ring of the formula

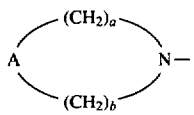

wherein A is —CH₂, O, S, or N—R₁₉, a is an integer from 1 to 4 and b is an integer from 1 to 4 provided that the sum of a+b is an integer from 2 to 5 and such heterocyclic rings wherein one available carbon has a lower alkyl substituent;

R₁₉ is hydrogen, lower alkyl, —(CH₂)ₙ-phenyl, or —(CH₂)ₙ-cycloalkyl;

m and m' are independently selected from zero and an integer from 1 to 5;

n and n' are independently selected from an integer from 1 to 5;

p is zero or one;

g is an integer from 2 to 5;

the term "alkyl of 1 to 7 carbons" refers to straight or branched chain radicals having up to seven carbon atoms;

the term "lower alkyl" refers to straight or branched chain radicals having up to four carbon atoms;

the terms "lower alkoxy" and "lower alkylthio" refer to such lower alkyl groups as defined above attached to an oxygen or sulfur;

the term "alkenyl" refers to straight or branched chain radicals of 2 to 7 carbons containing at least one double bond;

the term "cycloalkyl" refers to saturated rings of 4 to 7 carbons;

the term "alkylene" refers to straight chain bridge of 1 to 5 carbons connected by single bonds and such straight chain bridge of 1 to 5 carbons wherein one or more hydrogens have been replaced by a lower alkyl, hydroxy, amino, hydroxy substituted lower alkyl, or amino substituted lower alkyl;

the term "halo" refers to chloro, bromo, fluoro, and iodo;

the term "halo substituted alkyl" refers to such alkyl group in which one or more hydrogens have been replaced by chloro, bromo, or fluoro groups;

the term "aryl" refers to phenyl, diphenylmethyl, 1-naphthyl, 2-naphthyl, mono substituted phenyl, diphenylmethyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)₂ wherein alkyl is of 1 to 4 carbons, di or tri substituted phenyl, diphenylmethyl, 1-naphthyl or 2-naphthyl wherein said substituents are selected from methyl, methoxy, methylthio, halogen, hydroxy and amino; and the term "heterocyclo" refers to fully saturated, partially saturated, or unsaturated monocyclic rings of 5 or 6 atoms containing one or two O and S atoms and/or one to four N atoms provided that the total number of hetero atoms in the ring is 4 or less, bicyclic rings wherein the five or six membered ring containing O, S and N atoms as defined above is fused to a benzene or pyridyl ring, said monocyclic or bicyclic ring being attached by way of an available carbon atom, and substituted monocyclic and bicyclic rings as defined above wherein said substituent is on an available carbon atom and is lower alkyl of 1 to 4 carbons, halo substituted lower alkyl of 1 to 4 carbons, hydroxy, benzyl, or cyclohexylmethyl, and if said monocyclic or bicyclic ring has an available N atom such N atom can be substituted by

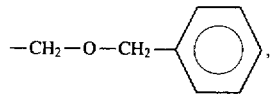

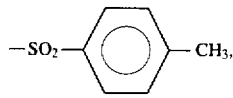

2,4-nitrophenyl, lower alkyl of 1 to 4 carbons, benzyl, or benzhydryl.

2. A compound of claim 1 wherein:

$R_1$ and $R_2$ are independently selected from the group consisting of hydrogen, alkyl of 1 to 7 carbons, alkenyl of 2 to 7 carbons, —$(CH_2)_m$-aryl, —$(CH_2)_m$-cycloalkyl, halo substituted alkyl of 1 to 7 carbons, —$(CH_2)_g$—O—$R_{15}$, —$(CH_2)_g$—S—$R_{15}$,

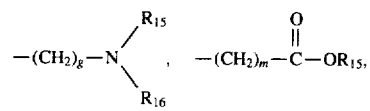

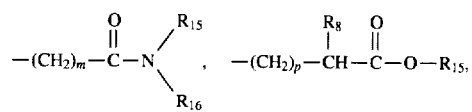

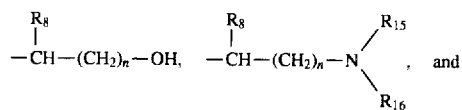

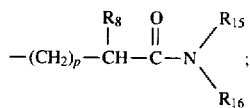

$R_3$, $R_7$, $R_8$, $R_{13}$ and $R_{14}$ are independently selected from the group consisting of hydrogen, alkyl of 1 to 7 carbons, halo substituted alkyl of 1 to 7 carbons, —$(CH_2)_m$-aryl, —$(CH_2)_m$-cycloalkyl, —$(CH_2)_n$—O—$R_{15}$, —$(CH_2)_n$—S—$R_{15}$,

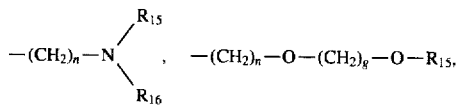

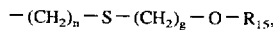

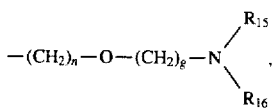

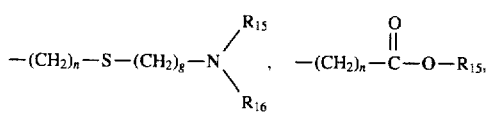

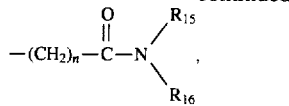

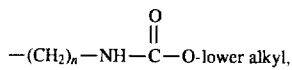

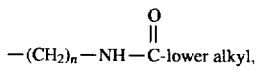

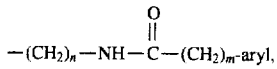

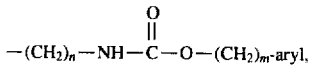

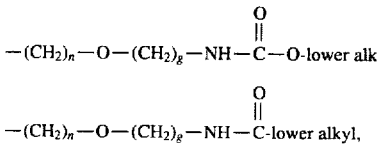

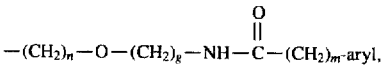

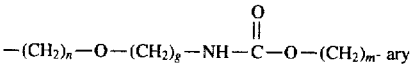

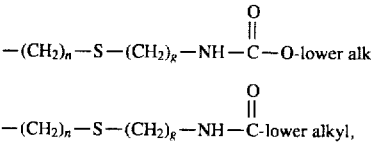

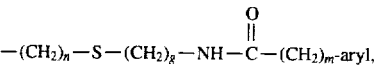

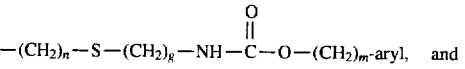

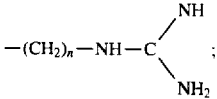

$R_4$ is hydrogen or alkyl of 1 to 7 carbons;

$R_5$ and $R_6$ are independently selected from the group consisting of hydrogen, alkyl of 1 to 7 carbons, halo substituted alkyl of 1 to 7 carbons, —$(CH_2)_m$-aryl, and —$(CH_2)_m$-cycloalkyl;

X is

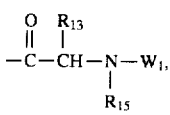

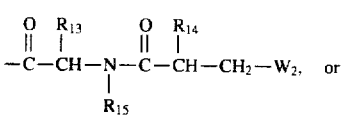

-continued

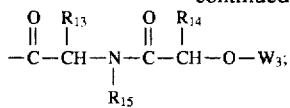

$R_{15}$ and $R_{16}$ are independently selected from the group consisting of hydrogen, alkyl of 1 to 7 carbons, —$(CH_2)_m$-cycloalkyl, and —$(CH_2)_m$-aryl;

$W_1$ is hydrogen,

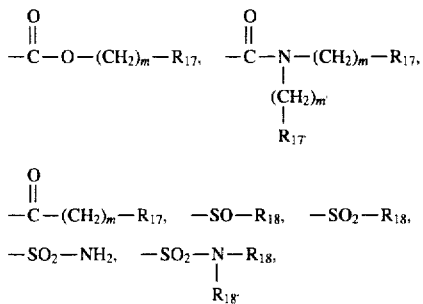

—$SO_2$—NH—$R_{18}$, or —$(CH_2)_m$—$R_{17}$, $W_2$ is hydrogen, —$R_{18}$,

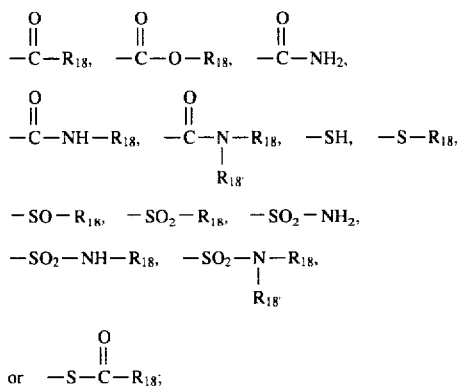

$W_3$ is hydrogen, $R_{18}$,

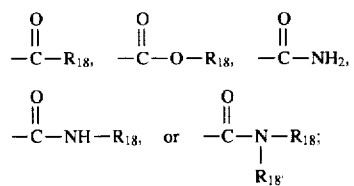

$R_{17}$ and $R_{17'}$ are independently selected from the group consisting of hydrogen, alkyl of 1 to 7 carbons, aryl, cycloalkyl, and

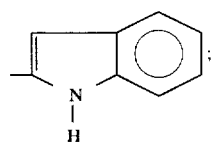

$R_{18}$ and $R_{18'}$ are independently selected from the group consisting of alkyl of 1 to 7 carbons, —$(CH_2)_m$-aryl, —$(CH_2)_m$-cycloalkyl,

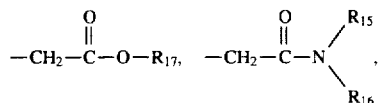

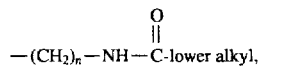

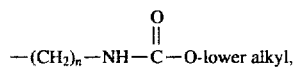

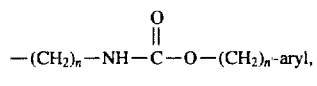

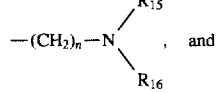

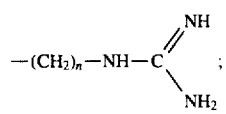

m and m' are independently selected from zero and an integer from 1 to 5;

n and n' are independently selected from an integer from 1 to 5;

p is zero or one;

g is an integer from 2 to 5;

the term "alkyl of 1 to 7 carbons" refers to straight or branched chain radicals having up to seven carbon atoms;

the term "lower alkyl" refers to straight or branched chain radicals having up to four carbon atoms;

the terms "lower alkoxy" and "lower alkylthio" refer to such lower alkyl groups as defined above attached to an oxygen or sulfur;

the term "alkenyl" refers to straight or branched chain radicals of 2 to 7 carbons containing at least one double bond;

the term "cycloalkyl" refers to saturated rings of 4 to 7 carbons;

the term "halo" refers to chloro, bromo, fluoro, and iodo;

the term "halo substituted alkyl" refers to such alkyl group in which one or more hydrogens have been replaced by chloro, bromo, or fluoro groups; and the term "aryl" refers to phenyl, diphenylmethyl, 1-naphthyl, 2-naphthyl, mono substituted phenyl, diphenylmethyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, diphenylmethyl, 1-naphthyl or 2-naphthyl wherein said substituents are selected from methyl, methoxy, methylthio, halogen, hydroxy and amino.

3. A compound of claim 2 wherein:

Z is $SO_2$.

4. A compound of claim 3 wherein:

$R_1$ and $R_2$ are both hydrogen or $R_1$ is straight or branched chain alkyl of 1 to 7 carbons, alkenyl of 2 to 4 carbons having a single double bond,

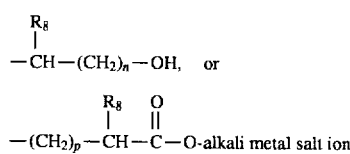

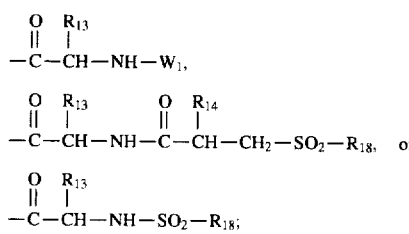

and $R_2$ is hydrogen or benzyl;

$R_3$, $R_4$, $R_5$, $R_6$, and $R_8$ are independently selected from the group consisting of hydrogen and straight or branched chain alkyl of 1 to 7 carbons;

$R_7$ is $-(CH_2)_m$-cycloalkyl;

X is

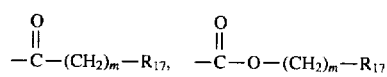

$R_{13}$ is straight or branched chain alkyl of 1 to 7 carbons;

$R_{14}$ is $(CH_2)_m$-aryl or straight or branched chain alkyl of 1 to 7 carbons;

$W_1$ is hydrogen,

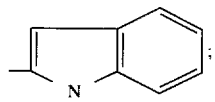

or $-SO_2-R_{18}$;

$R_{17}$ is straight or branched chain alkyl of 1 to 7 carbons, aryl, or

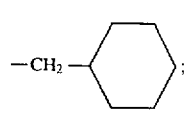

$R_{18}$ is straight or branched chain alkyl of 1 to 7 carbons or $-(CH_2)_m$-aryl; and the term "aryl" is phenyl, diphenylmethyl, 1-naphthyl, 2-naphthyl, mono substituted phenyl wherein said substituent is lower alkyl of 1 to 4 carbons, lower alkoxy of 1 to 4 carbons, lower alkylthio of 1 to 4 carbons, hydroxy, amino, Cl, Br, or F, or disubstituted phenyl wherein said substituents are selected from methyl, methoxy, methylthio, Cl, Br, F, hydroxy and amino.

5. A compound of claim 4 wherein:

$R_1$ is n-butyl;

$R_2$ is hydrogen;

$R_3$ is hydrogen;

$R_4$ is hydrogen;

$R_5$ is hydrogen;

$R_6$ is hydrogen;

$R_7$ is

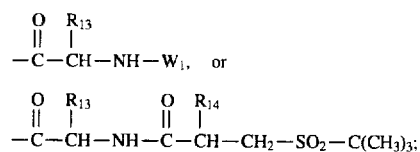

X is

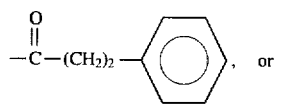

$R_{13}$ is $-CH_2CH(CH_3)_2$;

$W_1$ is hydrogen,

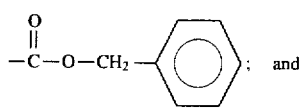

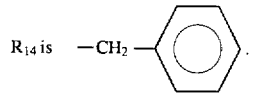

$R_{14}$ is

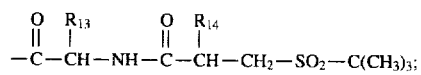

6. The compound of claim 5 wherein:

X is

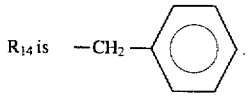

$R_{13}$ is $-CH_2CH(CH_3)_2$; and $R_{14}$ is

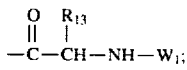

7. The compound of claim 5 wherein:

X is

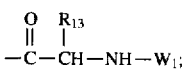

$R_{13}$ is $-CH_2CH(CH_3)_2$; and $W_1$ is hydrogen.

8. The compound of claim 5 wherein:

X is

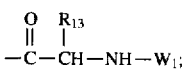

$R_{13}$ is $-CH_2CH(CH_3)_2$; and $W_1$ is

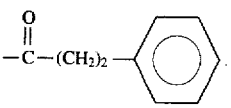

9. The compound of claim 5 wherein:

X is

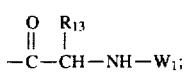

$R_{13}$ is —$CH_2CH(CH_3)_2$; and $W_1$ is

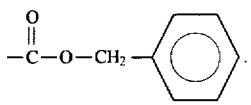

10. A compound of claim 1 wherein:

$R_1$ and $R_2$ are independently selected from the group consisting of hydrogen, alkyl of 1 to 7 carbons, alkenyl of 2 to 7 carbons, —$(CH_2)_m$-aryl, —$(CH_2)_m$-cycloalkyl, halo substituted alkyl of 1 to 7 carbons, —$(CH_2)_g$—O—$R_{15}$, —$(CH_2)_g$—S—$R_{15}$,

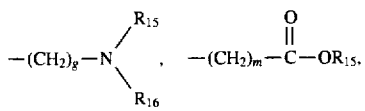

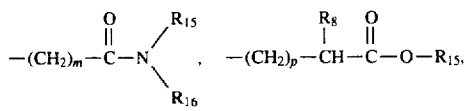

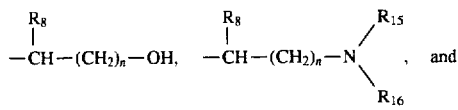

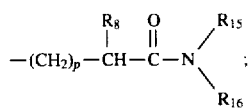

$R_3$, $R_7$, and $R_8$ are independently selected from the group consisting of hydrogen, alkyl of 1 to 7 carbons, halo substituted alkyl of 1 to 7 carbons, —$(CH_2)_m$-aryl, —$(CH_2)_m$-cycloalkyl, —$(CH_2)_n$—O—$R_{15}$, —$(CH_2)_n$—S—$R_{15}$,

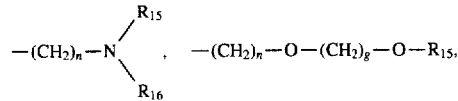

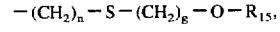

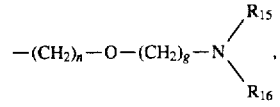

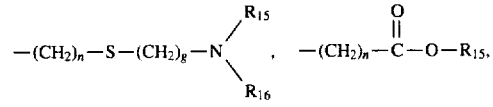

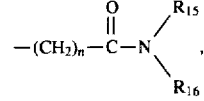

-continued

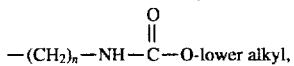

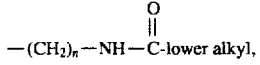

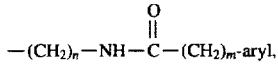

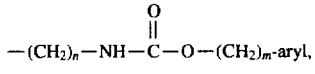

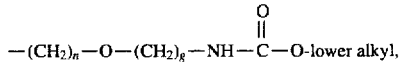

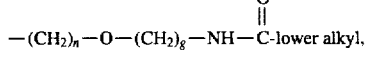

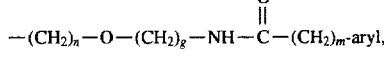

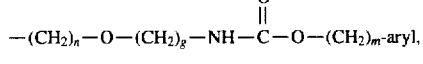

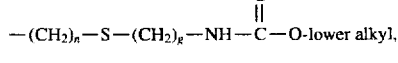

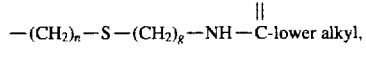

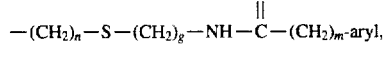

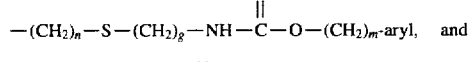     and

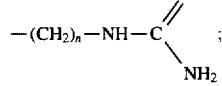

$R_4$ is hydrogen or alkyl of 1 to 7 carbons;

$R_5$ and $R_6$ are independently selected from the group consisting of hydrogen, alkyl of 1 to 7 carbons, halo substituted alkyl of 1 to 7 carbons, —$(CH_2)_m$-aryl, and —$(CH_2)_m$-cycloalkyl;

X is hydrogen or

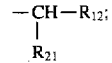

$R_{12}$ and $R_{21}$ are independently selected from the group consisting hydrogen, alkyl of 1 to 7 carbons, hydroxy substituted alkyl of 1 to 7 carbons, aryl, cycloalkyl, -alkylene-aryl, -alkylene-cycloalkyl,

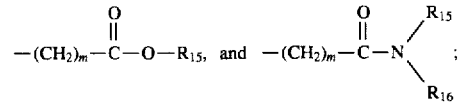

$R_{15}$ and $R_{16}$ are independently selected from the group consisting of hydrogen, alkyl of 1 to 7 carbons, —$(CH_2)_m$-cycloalkyl, and —$(CH_2)_m$-aryl;

m is zero or an integer from 1 to 5;

n is an integer from 1 to 5;

p is zero or one;

g is an integer from 2 to 5;

the term "alkyl of 1 to 7 carbons" refers to straight or branched chain radicals having up to seven carbon atoms;

the term "lower alkyl" refers to straight or branched chain radicals having up to four carbon atoms;

the terms "lower alkoxy" and "lower alkylthio" refer to such lower alkyl groups as defined above attached to an oxygen or sulfur;

the term "alkenyl" refers to straight or branched chain radicals of 2 to 7 carbons containing at least one double bond;

the term "cycloalkyl" refers to saturated rings of 4 to 7 carbons;

the term "alkylene" refers to straight chain bridge of 1 to 5 carbons connected by single bonds and such straight chain bridge of 1 to 5 carbons wherein one or more hydrogens have been replaced by a lower alkyl, hydroxy, amino, hydroxy substituted lower alkyl, or amino substituted lower alkyl;

the term "halo" refers to chloro, bromo, fluoro, and iodo;

the term "halo substituted alkyl" refers to such alkyl group in which one or more hydrogens have been replaced by chloro, bromo, or fluoro groups; and the term "aryl" refers to phenyl, diphenylmethyl, 1-naphthyl, 2-naphthyl, mono substituted phenyl, diphenylmethyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, diphenylmethyl, 1-naphthyl or 2-naphthyl wherein said substituents are selected from methyl, methoxy, methylthio, halogen, hydroxy and amino.

11. The compound of claim 10 wherein: Z is SO$_2$.

12. The compound of claim 11 wherein:

R$_1$ and R$_2$ are both hydrogen, or R$_1$ is straight or branched chain alkyl of 1 to 7 carbons,

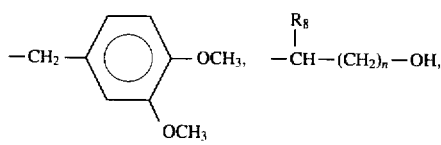

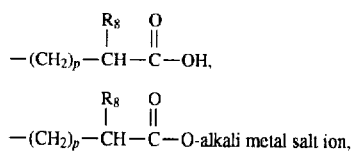

or diphenylmethyl and R$_2$ is hydrogen, or R$_1$ is straight or branched chain alkyl of 1 to 7 carbons and R$_2$ is methyl, benzyl, or

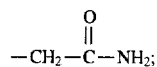

R$_3$, R$_4$, R$_5$, R$_6$, and R$_8$ are independently selected from the group consisting of hydrogen and straight or branched chain alkyl of 1 to 7 carbons;

R$_7$ is —(CH$_2$)$_m$-cycloalkyl; and

X is hydrogen.

13. A compound of claim 12 wherein:

R$_1$ is n-butyl;

R$_2$ is hydrogen;

R$_3$, R$_4$, R$_5$ and R$_6$ are all hydrogen; and

R$_7$ is

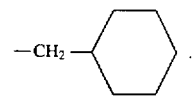

14. A compound of claim 12 wherein:

R$_1$ is n-butyl;

R$_2$ is hydrogen;

R$_3$ and R$_4$ are both methyl;

R$_5$ and R$_6$ are both hydrogen; and

R$_7$ is

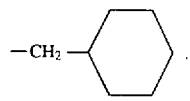

15. A compound of claim 12 wherein

R$_1$ is n-butyl;

R$_2$ is hydrogen;

R$_3$ is methyl;

R$_4$, R$_5$, and R$_6$ are all hydrogen; and

R$_7$ is

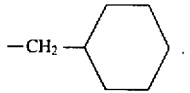

16. A compound of claim 12 wherein

R$_1$ is

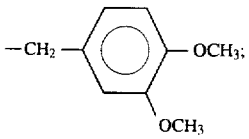

R$_2$ is hydrogen;

R$_3$, R$_4$, R$_5$ and R$_6$ are all hydrogen; and

R₇ is

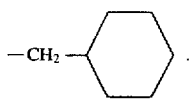

17. A compound of claim 12 wherein
R₁ is n-butyl;
R₂ is benzyl;
R₃, R₄, R₅ and R₆ are all hydrogen; and
R₇ is

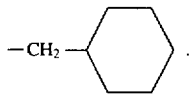

18. A compound of claim 12 wherein
R₁ and R₂ are both hydrogen;
R₃, R₄, R₅ and R₆ are all hydrogen; and
R₇ is

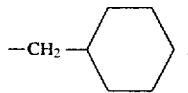

19. A compound of claim 12 wherein:
R₁ is n-butyl;
R₂ is hydrogen;
R₃, R₄ and R₅ are all hydrogen;
R₆ is methyl; and
R₇ is

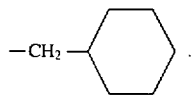

20. A compound of claim 12 wherein:
R₁ is —(CH₂)₂—OH;
R₂ is hydrogen;
R₃, R₄, R₅, and R₆ are all hydrogen; and
R₇ is

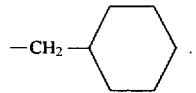

21. A compound of claim 12 wherein
R₁ is n-butyl;
R₂ is methyl;
R₃, R₄, R₅ and R₆ are all hydrogen; and
R₇ is

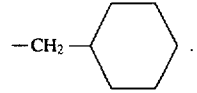

22. A compound of claim 12 wherein
R₁ is diphenylmethyl;
R₂ is hydrogen;

R₃, R₄, R₅ and R₆ are all hydrogen; and
R₇ is

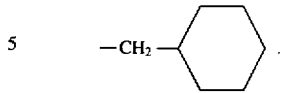

23. A compound of claim 12 wherein:
R₁ is —CH₂—COOLi;
R₂ is hydrogen;
R₃, R₄, R₅ and R₆ are all hydrogen; and
R₇ is

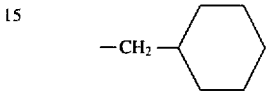

24. A compound of claim 12 wherein:
R₁ is n-butyl;
R₂ is

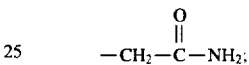

R₃, R₄, R₅ and R₆ are all hydrogen and;
R₇ is

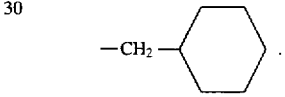

25. A compound of claim 12 wherein:
R₁ is

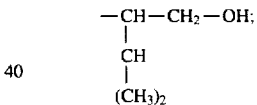

R₂ is hydrogen;
R₃, R₄, R₅ and R₆ are all hydrogen; and
R₇

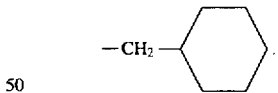

26. A compound of formula 12 wherein:
R₁ is —(CH₂)₄—OH;
R₂ is hydrogen;
R₃, R₄, R₅ and R₆ are all hydrogen; and
R₇ is

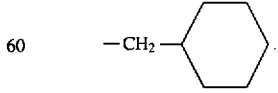

27. A compound of formula 11 wherein:
R₁ is n-butyl;
R₂ is hydrogen;
R₃, R₄, R₅, and R₆ are all hydrogen;

$R_7$ is

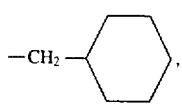

and

X is —$(CH_2)_3$—CH $(CH_3)_2$.

28. A compound of formula 11 wherein:

$R_1$ is n-butyl;

$R_2$ is hydrogen;

$R_3$, $R_4$, $R_5$ and $R_6$ are all hydrogen;

X is

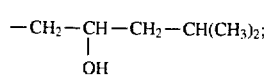

and $R_7$ is

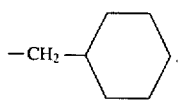

29. The compound of claim 1 wherein:

$R_1$ and $R_2$ are independently selected from the group consisting of hydrogen, alkyl of 1 to 7 carbons, alkenyl of 2 to 7 carbons, —$(CH_2)_m$-aryl, —$(CH_2)_m$-cycloalkyl, halo substituted alkyl of 1 to 7 carbons, —$(CH_2)_g$—O—$R_{15}$, —$(CH_2)_g$—S—$R_{15}$,

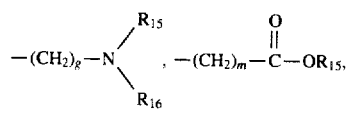

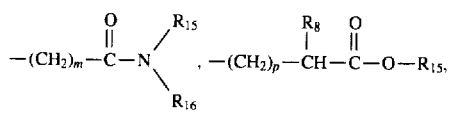

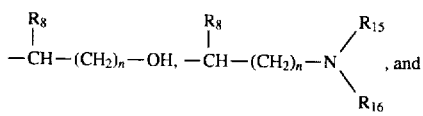

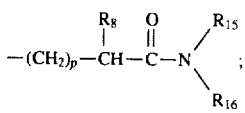

$R_3$, $R_7$ and $R_8$ are independently selected from the group consisting of hydrogen, alkyl of 1 to 7 carbons, halo substituted alkyl of 1 to 7 carbons, —$(CH_2)_m$-aryl, —$(CH_2)_m$-cycloalkyl, —$(CH_2)_n$—O—$R_{15}$, —$(CH_2)_n$—S—$R_{15}$,

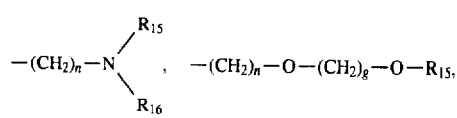

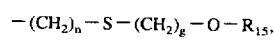

-continued

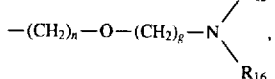

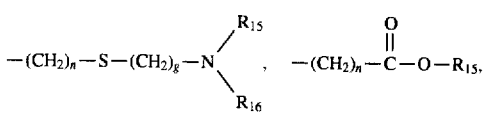

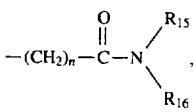

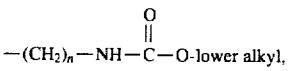

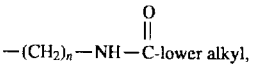

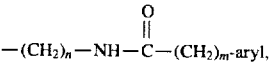

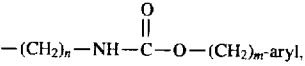

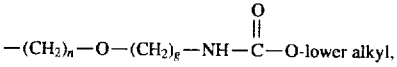

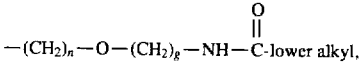

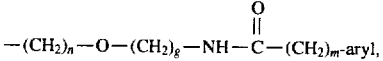

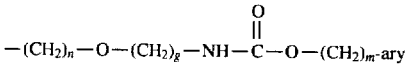

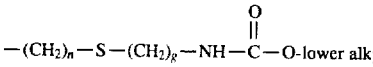

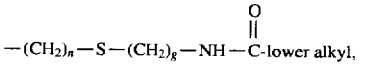

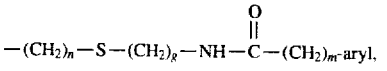

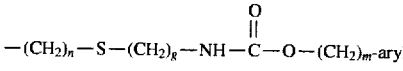

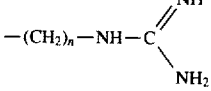

$R_4$ is hydrogen or alkyl of 1 to 7 carbons;

$R_5$ and $R_6$ are independently selected from the group consisting of hydrogen, alkyl of 1 to 7 carbons, halo substituted alkyl of 1 to 7 carbons, —$(CH_2)_m$-aryl, and —$(CH_2)_m$-cycloalkyl;

X is

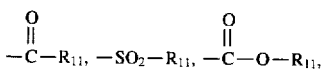

-continued

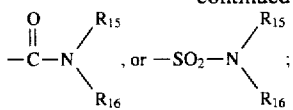

$R_{11}$ is alkyl of 1 to 7 carbons, hydroxy substituted alkyl of 1 to 7 carbons, aryl, heterocyclo, cycloalkyl, alkylene-aryl, alkyleneheterocyclo, alkylene-cycloalkyl,

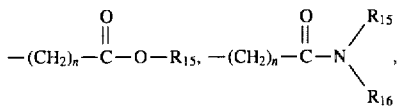

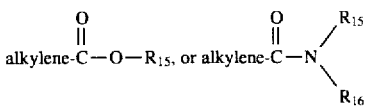

wherein heterocyclo is 2-, 3-, or 4-pyridinyl, substituted 2-, 3-, or 4-pyridinyl wherein said substituent is attached to an available carbon atom and is methyl, methoxy, or hydroxy, 4-pyridazinyl, 2-pyrazinyl, or imidazolyl;

$R_{15}$ and $R_{16}$ are independently selected from the group consisting of hydrogen, alkyl of 1 to 7 carbons, —$(CH_2)_m$-cycloalkyl, and —$(CH_2)_m$-aryl;

m is zero or an integer from 1 to 5;

n is an integer from 1 to 5;

p is zero or one;

g is an integer from 2 to 5;

the term "alkyl of 1 to 7 carbons" refers to straight or branched chain radicals having up to seven carbon atoms;

the term "lower alkyl" refers to straight or branched chain radicals having up to four carbon atoms;

the terms "lower alkoxy" and "lower alkylthio" refer to such lower alkyl groups as defined above attached to an oxygen or sulfur;

the term "alkenyl" refers to straight or branched chain radicals of 2 to 7 carbons containing at least one double bond;

the term "cycloalkyl" refers to saturated rings of 4 to 7 carbons;

the term "alkylene" refers to straight chain bridge of 1 to 5 carbons connected by single bonds and such straight chain bridge of 1 to 5 carbons wherein one or more hydrogens have been replaced by a lower alkyl, hydroxy, amino, hydroxy substituted lower alkyl, or amino substituted lower alkyl;

the term "halo" refers to chloro, bromo, fluoro, and iodo;

the term "halo substituted alkyl" refers to such alkyl group in which one or more hydrogens have been replaced by chloro, bromo, or fluoro groups; and the term "aryl" refers to phenyl, diphenylmethyl, 1-naphthyl, 2-naphthyl, mono substituted phenyl, diphenylmethyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, diphenylmethyl, 1-naphthyl or 2-naphthyl wherein said substituents are selected from methyl, methoxy, methylthio, halogen, hydroxy and amino.

30. The compound of claim 29 wherein: Z is $SO_2$.

31. The compound of claim 30 wherein:

X is

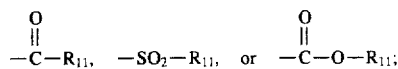

$R_1$ is straight or branched chain alkyl of 1 to 7 carbons;

$R_2$ is hydrogen;

$R_3$, $R_4$, $R_5$, and $R_6$ are independently selected from the group consisting of hydrogen and straight or branched chain alkyl of 1 to 7 carbons;

$R_7$ is —$(CH_2)_m$-cycloalkyl; and $R_{11}$ is straight or branched chain alkyl of 1 to 7 carbons, hydroxy substituted straight or branched chain alkyl of 1 to 7 carbons, aryl or

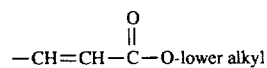

wherein lower alkyl is straight or branched chain of 1 to 4 carbons.

32. A compound of claim 31 wherein:

$R_1$ is n-butyl;

$R_3$, $R_4$, $R_5$ and $R_6$ are all hydrogen;

$R_7$ is

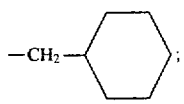

and

X is

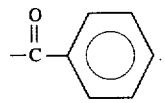

33. A compound of claim 31 wherein:

$R_1$ is n-butyl;

$R_3$, $R_4$, $R_5$ and $R_6$ are all hydrogen;

$R_7$ is

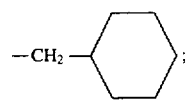

and

X is

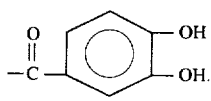

34. A compound of claim 31 wherein:

$R_1$ is n-butyl;

$R_3$, $R_4$, $R_5$ and $R_6$ are all hydrogen;

$R_7$ is

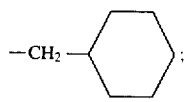

and

X is

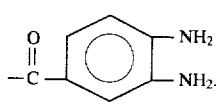

35. A compound of claim 31 wherein:

$R_1$ is n-butyl;

$R_3$, $R_4$, $R_5$ and $R_6$ are all hydrogen;

$R_7$ is

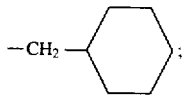

and

X is

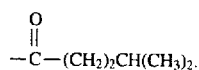

36. A compound of claim 31 wherein:

$R_1$ is n-butyl;

$R_3$, $R_4$, $R_5$ and $R_6$ are all hydrogen;

$R_7$ is

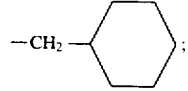

and

X is

37. A compound of claim 31 wherein:

$R_1$ is n-butyl;

$R_3$, $R_4$, $R_5$ and $R_6$ are all hydrogen;

$R_7$ is

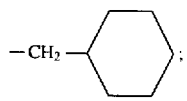

and

X is

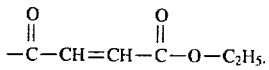

38. A compound of claim 31 wherein:

$R_1$ is n-butyl;

$R_3$, $R_4$, $R_5$ and $R_6$ are all hydrogen;

$R_7$ is

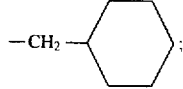

and

X is —$SO_2$—$CH_3$.

39. A compound of claim 31 wherein:

$R_1$ is n-butyl;

$R_3$, $R_4$, $R_5$ and $R_6$ are all hydrogen;

$R_7$ is

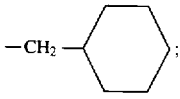

and

X is

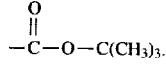

40. A compound of claim 31 wherein:

$R_1$ is n-butyl;

$R_3$, $R_4$, $R_5$ and $R_6$ are all hydrogen;

$R_7$ is

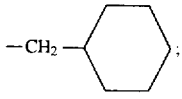

and

X is

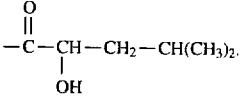

41. The compound of claim 31 wherein:

$R_1$ is n-butyl;

$R_3$ is methyl;

$R_4$, $R_5$ and $R_6$ are all hydrogen;

R$_7$ is

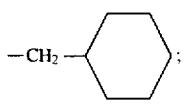

and

X is

42. The compound of claim 30 wherein:

X is

R$_1$ is straight or branched chain alkyl of 1 to 7 carbons;
R$_2$, R$_3$, R$_4$, R$_5$, and R$_6$ are all hydrogen;
R$_7$ is —(CH$_2$)$_m$-cycloalkyl;
R$_{11}$ is heterocyclo or alkylene-heterocyclo wherein heterocyclo is 2-, 3-, or 4-pyridinyl, substituted 2-, 3-, or 4-pyridinyl wherein said substituent is attached at an available carbon atom and is methyl, methoxy or hydroxy, 4-pyridazinyl, 2-pyrazinyl, or imidazolyl.

43. The compound of claim 42 wherein:

R$_1$ is n-butyl;

R$_7$ is

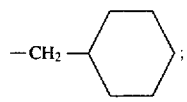

and

X is

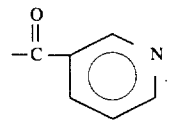

44. The compound of claim 42 wherein:

R$_1$ is n-butyl;

R$_7$ is

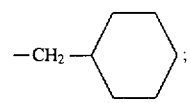

and

X is

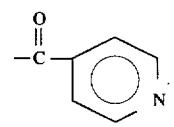

45. The compound of claim 42 wherein:

R$_1$ is butyl;

R$_7$ is

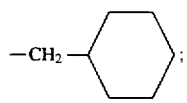

and

X is

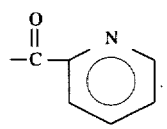

46. The compound of claim 42 wherein:

R$_1$ is n-butyl;

R$_7$ is

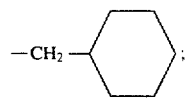

and

X is

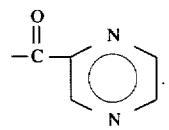

47. The compound of claim 42 wherein:

R$_1$ is n-butyl;

R$_7$ is

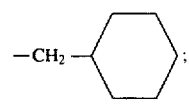

and

X is

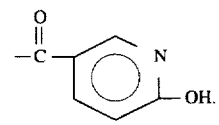

48. The compound of claim 42 wherein:

R$_1$ is n-butyl;

R$_7$ is

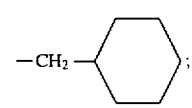

and

X is
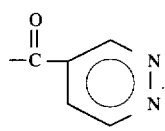
49. The compound of claim 42 wherein:
$R_1$ is n-butyl;
$R_7$ is
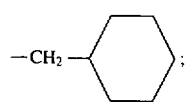
and
X is
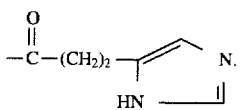
50. The compound of claim 42 wherein:
X is
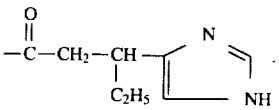
* * * * *